United States Patent [19]
Arnold et al.

[11] Patent Number: 6,063,637
[45] Date of Patent: *May 16, 2000

[54] SENSORS FOR SUGARS AND OTHER METAL BINDING ANALYTES

[75] Inventors: Frances H. Arnold, Pasadena, Calif.; Zhibin Guan, Hockessin, Del.; Chao-Tsen Chen, New York, N.Y.; Guohua Chen, Pasadena, Calif.

[73] Assignee: California Institute of Technology, Pasadena, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/875,047

[22] PCT Filed: Mar. 3, 1997

[86] PCT No.: PCT/US97/03654

§ 371 Date: Jul. 7, 1997

§ 102(e) Date: Jul. 7, 1997

[87] PCT Pub. No.: WO97/33177

PCT Pub. Date: Sep. 12, 1997

Related U.S. Application Data

[63] Continuation-in-part of application No. 08/571,440, Dec. 13, 1995, abandoned.
[60] Provisional application No. 60/012,756, Mar. 4, 1996.

[51] Int. Cl.[7] .......................... G01N 21/00; G01N 33/00
[52] U.S. Cl. .................. 436/94; 422/82.01; 422/82.02; 422/82.03; 422/82.05; 422/82.06; 422/82.07; 422/82.08; 422/82.09; 436/93; 436/95; 436/127; 436/128; 436/131; 436/149; 436/150; 436/151; 436/164; 436/166; 436/169; 436/172
[58] Field of Search .......................... 422/82.01–82.03, 422/82.05–82.09; 436/93–95, 127, 128, 131, 149, 150, 151, 164, 166, 169, 172, 805, 800, 811, 815

[56] References Cited

U.S. PATENT DOCUMENTS

| | | | |
|---|---|---|---|
| 3,282,649 | 11/1966 | Bittner | 23/230 |
| 5,217,691 | 6/1993 | Greene et al. | 422/56 |
| 5,244,562 | 9/1993 | Russell | 204/418 |
| 5,310,648 | 5/1994 | Arnold et al. | 435/5 |

FOREIGN PATENT DOCUMENTS

| | | | |
|---|---|---|---|
| 141 844 | 5/1980 | Germany | 3/51 |

OTHER PUBLICATIONS

Hagedorn–Jensen et al., (II) EDTA, *Japan Analyst*, vol. 18, 1359–1364 (1969).

Plunkett et al., "Novel Metal–Affinity Adsorbents Prepared by Template Polymerization," *Am. Chem. Soc.*, 244–247 (1992).

(List continued on next page.)

*Primary Examiner*—Arlen Soderquist
*Attorney, Agent, or Firm*—Darby & Darby

[57] ABSTRACT

Sensors (20, 50, 70) for use in detecting the presence of sugars and other analytes (target molecules). The sensor is composed of a metal complex that binds to the target molecule and releases a proton or includes an exchangable ligand which is exchanged for the target molecule during the binding interaction between the metal complex and the target molecule. The result of the binding interaction is the release of a proton, hydroxide ion or ligand species generated during the ligand exchange. Measurement of the release of proton, hydroxide ion or other ligand species from the sensor (20, 50, 70) provides an indirect indication of target molecule concentration. The metal complexes may be attached to support structures (10, 12) to provide both anchoring and positioning of the metal ions to increase selectivity of sugar/metal complex interactions. Detection systems in which pH is used as an indication of proton or hydroxide release are disclosed, as are detection systems in which Cl[−] release is used. Methods for monitoring the concentrations of sugars and related molecules using the metal based sensors (20, 50, 70) are also disclosed.

32 Claims, 24 Drawing Sheets

OTHER PUBLICATIONS

Reeves et al., "Cuprammonium–Glycoside Complexes. VIII. The Copper to Diol Combining Ratio," *Cuprammonium–Glycoside Complexes. VIII*, vol. 26, 3487–3489 (1961).

Hedborg et al., "Some studies of molecularly–imprinted polymer membranes in combination with field–effect devices," *Sensors and Actuators A*, 37–38 (1993) 796–799.

Starodub et al., "Template sensors for low weight organic molecules base on $SiO_2$ surfaces," *Sensors and Actuators B*, 13–14 (1993) 708–710.

Burstyn et al., "Selective Catalytic Hydrolysis of a Simple Phosphodiester by a Macrocylic Copper(II) Complex," *Inorg. Chem.* 32 (1993) 3585–3586.

Morrow et al., "Hydrolysis of Phosphate Diesters with Copper(II) Catalysts," *Inorg. Chem.* 27 (1988) 3387–3394.

Deal et al., "Mechanistic Studies of Dichloro(1,4,7–triazacyclononane)copper(II)–Catalyzed Phosphate Diester Hydrolysis," *Inorg. Chem.* 35 (1996) 2792–2798.

Schwindinger etal. "Molecular Structure of Dichloro(1,4,7–triazacyclononane)copper(II), a Macrocyclic Triamine Complex with an Unusually Small Formation Constant," *Inorg. Chem.* 19 (1980) 1379–1381.

Vidyasankar et al., "Molecular imprinting: selective materials for separations, sensors and catalysis," *Biotechnology*, 6 (1995) 218–224.

Khorasani et al., "Spectral Data for Copper(II)–Sucrose Species in Aqueous Alkali Solutions," *Pakistan J. Sci. Ind. Res.*, vol. 15, Nos. 1–2, Feb.–Apr. 1972.

Piletsky et al., "Sensors for low–weight organic molecules based on molecular imprinting technique," *Sensors and Actuators B*, 18–19 (1994) 629–631.

Davydova et al., "Application of a Copper–Selective Electrode to the Determination and Investigation of Monomeric and Polymeric Amino Sugars," Translated from *Zhurnal Analiticheskoi Khimii*, vol. 47, No. 6, pp. 1076–1082, Jun., 1992.

Shalaby et al., "Indirect potentiometric titration of reducing carbohydrates," *Acta Pharmaceutica Hungarica* 59, 257–262 (1989).

Chaudhuri et al., "Preparation, Magnetism, and Crystal Structures of the Tautomers $[LCu(\mu_2–OH)_2CuL](ClO_4)_2$ (Blue) and $[LCu(\mu_2–OH_2)(\mu_2–o)CuL](ClO_4)_2$ (Green): $\mu$–Aqua–$\mu$–oxo vs. Di–$\mu$–hydroxo Linkage," *Agnew. Chem. Int. Ed. Engl.* 24 (1985) No. 1, 57–59.

Reeves et al., "The Amminehydroxocopper(II)–diolate Chelation Reaction," *JACI* (1992) 2491–2495.

Wulff, "Molecular Recognition in Polymers Prepared by Imprinting with Templates," *Am. Chem. Soc. Symp.* Ser. 308, 186–230 (1986).

Wulff, "Biorecognition in Molecularly Imprinted Polymers," *Molecular Interactions in Bioseparations*, 23 (1993) 363–381.

Nilsson et al., "Molecular imprinting of acetylated carbohydrate derivatives into methacrylic polymers," *J. Chromatog. A.*, 707 (1995) 199–203.

Ekberg et al., "Molecular imprinting: a technique for producing specific separation materials," *TIBTECH* 7 (1989) (92–96).

Porath et al., "Metal chelate affinity chromatography, a new approach to protein fractionation," *Nature*, vol. 258 (1975) 598–599.

Mayes et al., "Sugar Binding Polymers Showing High Anomeric and Epimeric Discrimination Obtained by Non-covalent Molecular Imprinting," *Analytical Biochemistry* 222, 483–488 (1994).

Wulff et al., "Racemic Resolution of Free Sugars with Macroporous Polymers Prepared by Molecular Imprinting. Selectivity Dependence on the Arrangement of Functional Groups versus Spatial Requirements," *J. Org. Chem.* (1991) 56, 395–400.

Wilkins et al., "Implantable Glucose Sensor," *J. Biomed. Eng.* (1983), vol. 5, 309–315.

Pickup, "Developing glucose sensors for in vivo use," *TIBTECH* (1993), vol. 11. 285–291.

FIG. 1b
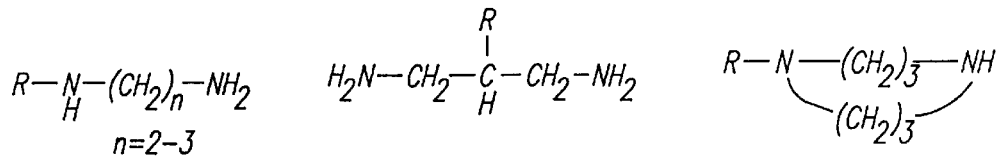
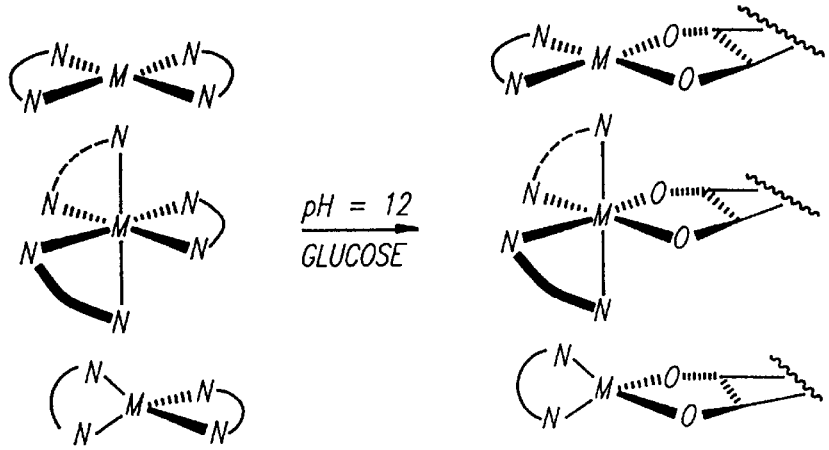
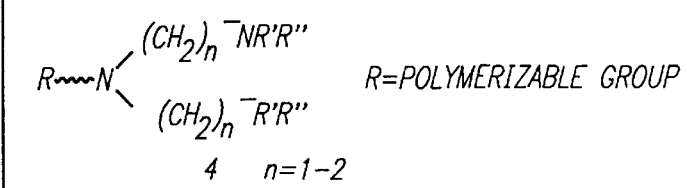
FIG. 1c
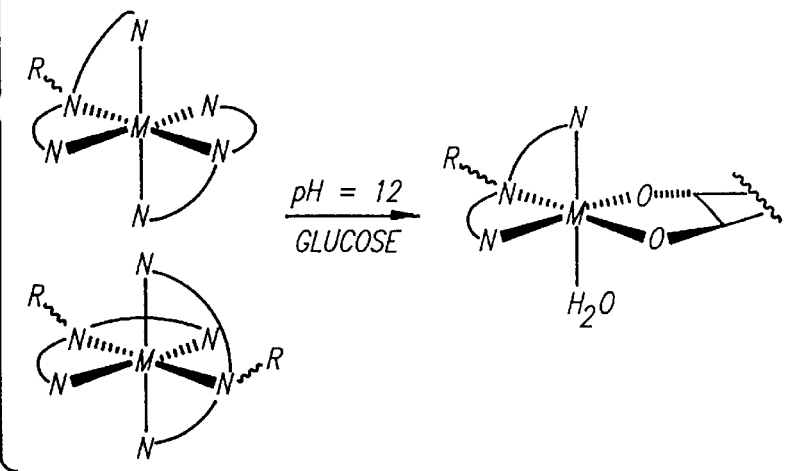

$i = j = k = 2$ OR $3$
$i = j = 2, k = 3$
$i = j = 3, k = 2$ $i = j = k = 2$ OR $3$
$i = j = 2, k = 3$
$i = j = 3, k = 2$

HYDROGEN BONDING $i = j = k = 1 = 2$
$i = K = 2, j = k = 3$
$i = j = k = 1 = 3$

FIG. 6
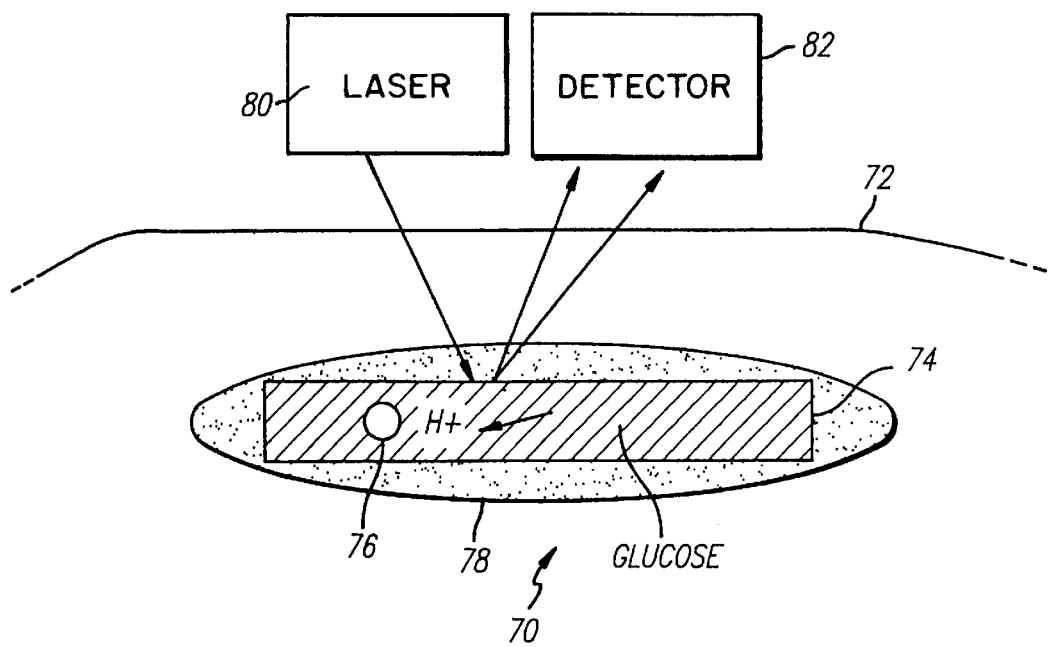
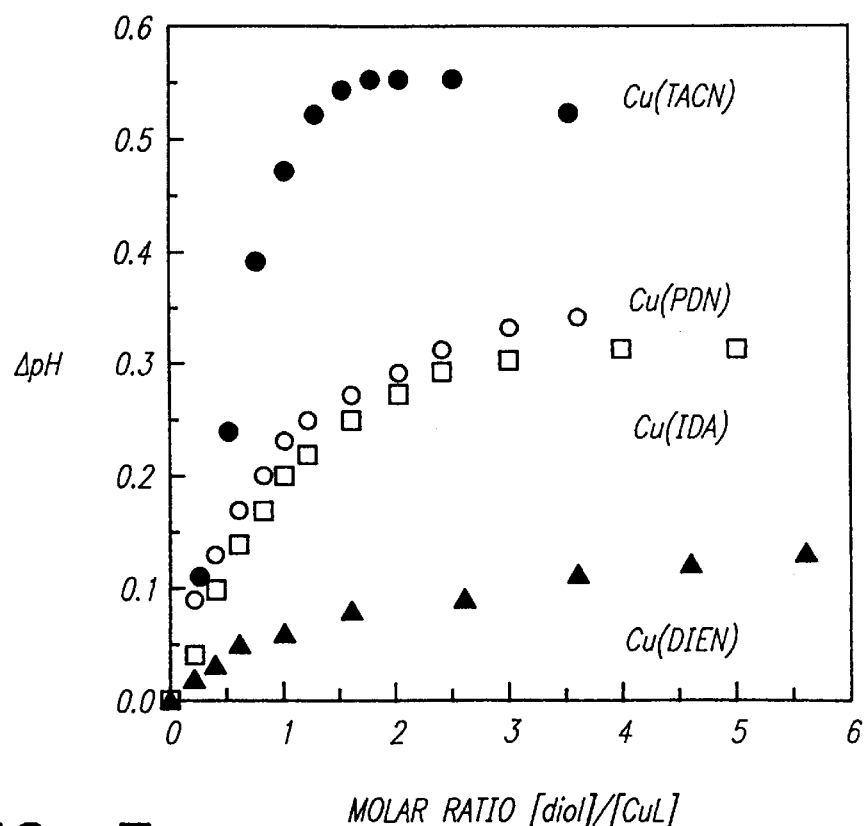
FIG. 7

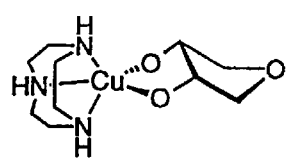 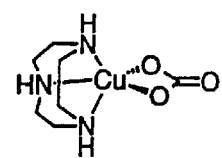
1                            2
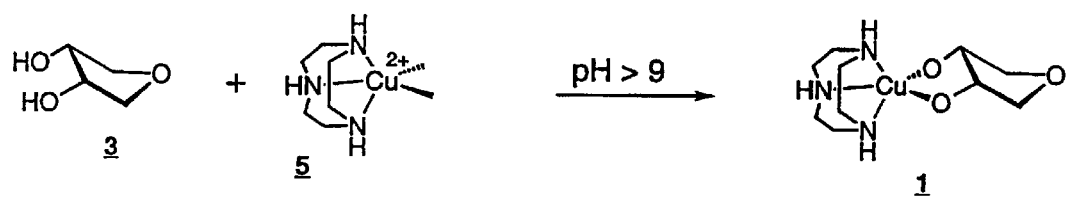
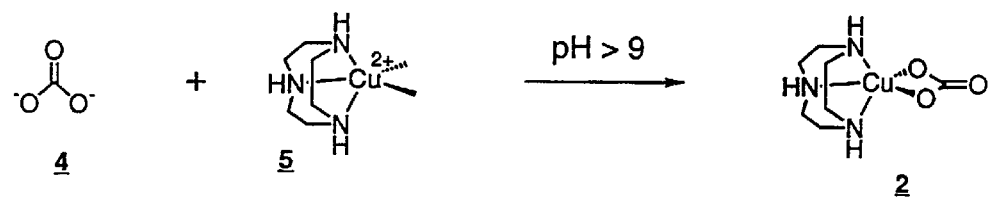
FIG. 18a

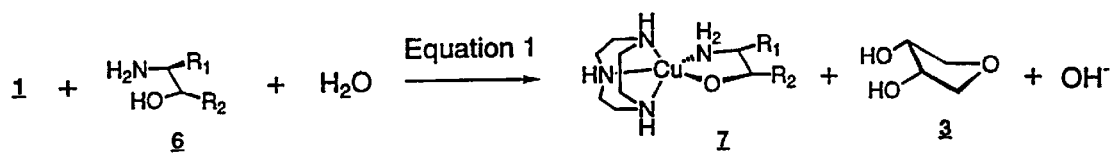
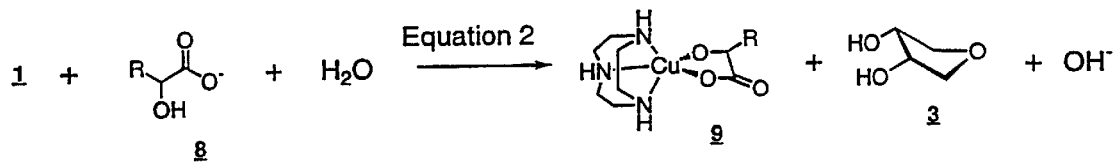
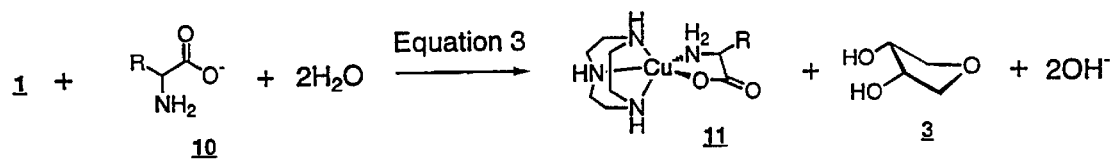
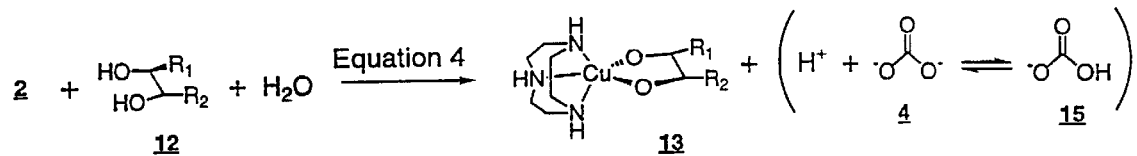
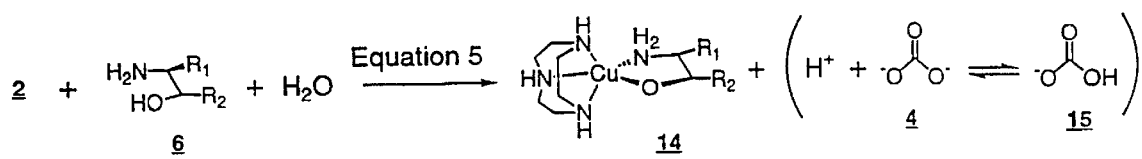
FIG. 19

| | |
|---|---|
| Nitrogen-based bidentate ligands | 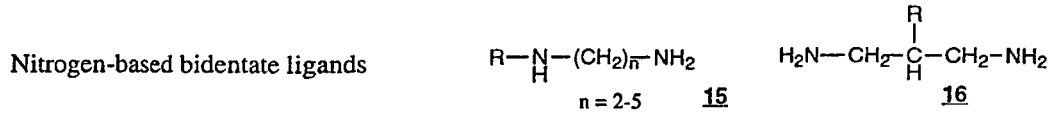 |
| | 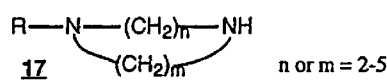 |
| Nitrogen-based linear tridentate ligands | 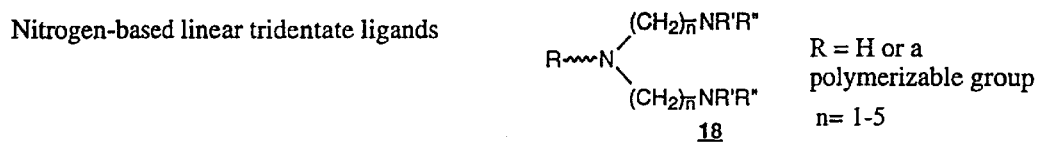  R = H or a polymerizable group  n = 1-5 |
| Nitrogen-based linear tetradentate ligands | 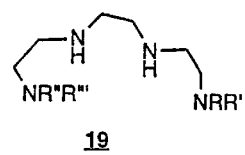 |
| Nitrogen-based tridentate macrocycles | 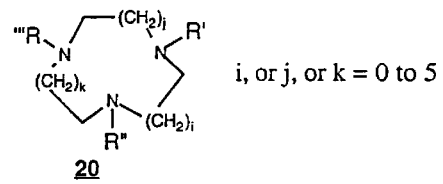  i, or j, or k = 0 to 5 |
| Nitrogen-based tetradentate macrocyclic ring | 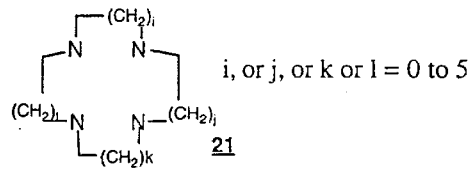  i, or j, or k or l = 0 to 5 |

Tridentate ring ligands consisting of pyridine, pyrazole and imidazole rings

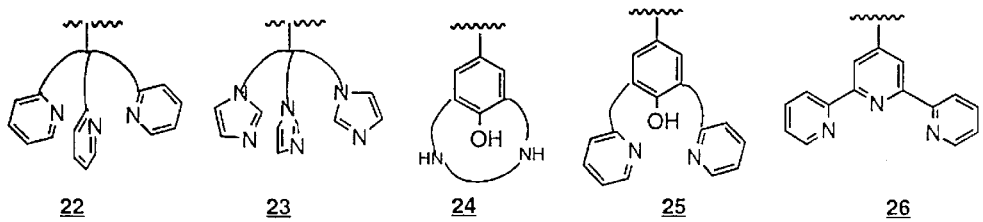

∽|∽ : polymerizable functional groups

FIG. 20

Linear heteronuclear ligands
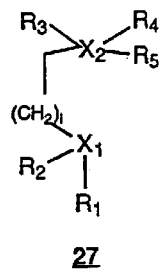
27
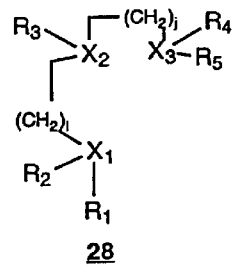
28
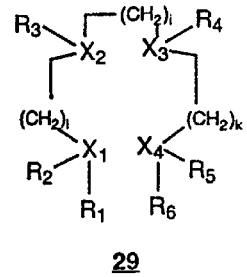
29
Cyclic heteronuclear ligands
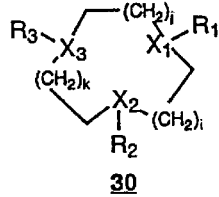
30
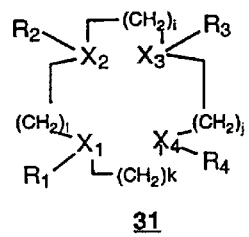
31
$0 \leq i$ or $j$ or $k$ or $l \leq 5$
$X_1$ or $X_2$ or $X_3$ or $X_4 =$ O, or S, or N
When $X_1$ or $X_2$ or $X_3$ or $X_4 =$ N,
$R_n =$ H, or $CF_3$, or $C_5F_5$ or any other electron withdrawing group, or polymerizable group (n =1-6)
1,10-phenanthroline and analogs
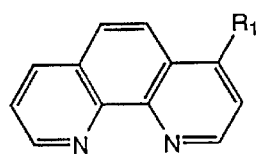
32
Diaminophenanthrene and analogs
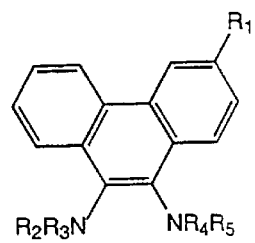
33
FIG. 21

Equation 1
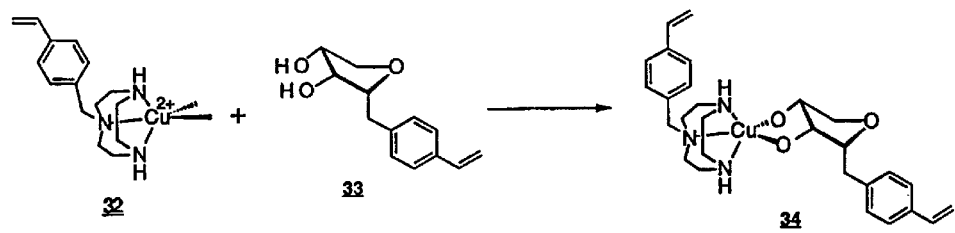
Equation 2
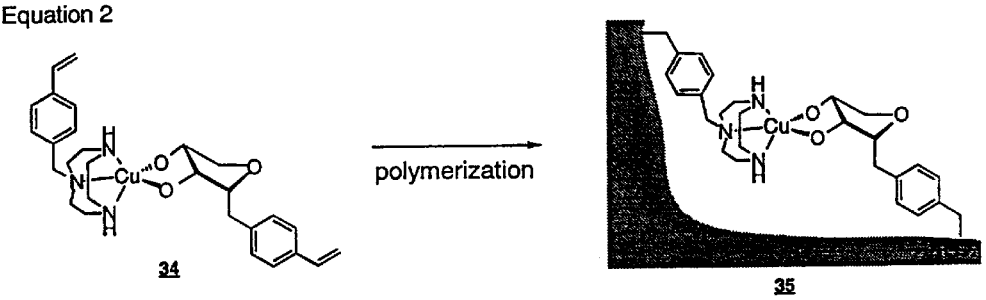
Equation 3
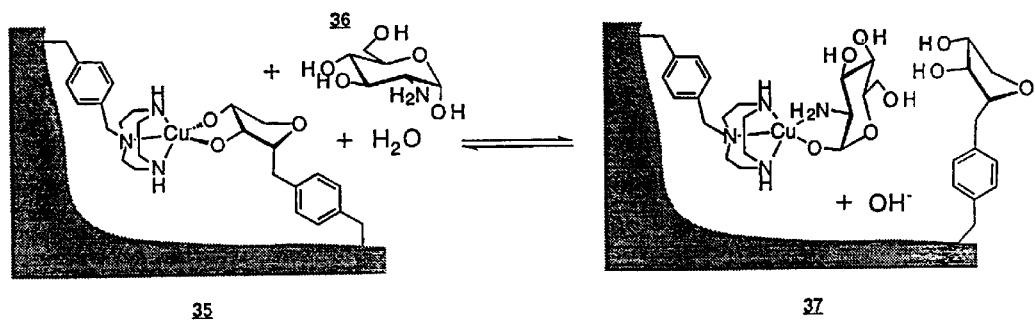
FIG. 22

SENSORS FOR SUGARS AND OTHER METAL BINDING ANALYTES

This application is the National Stage of International Application No. PCT/US97/03654 filed on Mar. 3, 1997, which is a continuation-in-part of application Ser. No. 08/571,440 filed on Dec. 13, 1995, now abandoned. This application claims the benefit of provisional application Ser. No. 60/012,756 which was filed on Mar. 4, 1996.

The U.S. Government has certain rights in this invention pursuant to Grant No. N00014-92-J-1178 awarded by the Navy, and Grant No. BES-9416915 awarded by the National Science Foundation.

BACKGROUND OF THE INVENTION

1. Field of the Invention

This invention relates generally to devices and methods used to test for and monitor the concentrations in solutions of sugars, amino acids and other compounds capable of complexing metal ions. More particularly, the present invention is directed to sensors which rely on metal coordination/chelation interactions between nucleophilic groups on targeted compounds and the release of protons, hydroxide ions or detectable ligands from metal ion complexes to provide detection and/or measurement of analyte compounds in aqueous, mixed aqueous-organic or organic solutions.

2. Description of Related Art

Many different devices and methods are presently being used to measure the concentration of various sugars and amino acids in a wide variety of solutions. Many industrial manufacturing and food processing systems require that the level of one or more sugars and/or amino acids be carefully monitored at various stages to insure desired quality of final products. For example, the varying glucose concentrations during fermentation processes are important process control parameters, and their continuous monitoring can improve the yield and quality of the fermentation product. In addition, there are a large number of situations where the amount of sugar in finished food stuffs and other sugar containing products must be determined. On line, continuous measurement is important to reduce the risk of contamination, labor costs and delays associated with off-line measurements. To be able to perform on-line measurements, there is a need for sterilizable sensors with rapid response times and high sensitivity, yet which also require minimum maintenance and calibration.

One of the most important uses for sugar analysis techniques is in the medical field where monitoring of sugar levels in biological fluids is critical to proper diagnosis and treatment of diabetes and other diseases. With respect to medical applications, glucose is by far the most important sugar, and diabetes is the most common disease for which glucose determinations are routinely conducted. Diabetes is a disease of the metabolic system that affects more than 14 million people in the United States and over 100 million people worldwide. It is characterized by an elevated blood-glucose concentration which is caused by a lack of the hormone insulin. Sugars are the primary source of metabolic energy, and the inability to self-regulate the levels of sugar metabolized by the body leads to many other medical problems, including but not limited to blindness, heart disease and kidney failure.

Treatment of diabetes involves monitoring of the patient's blood-glucose levels, with insulin injections being given when the glucose concentration rises above normal levels. A simple and accurate method for measuring blood-glucose concentrations is an essential cornerstone of any diabetes treatment protocol, since excessively high blood-glucose levels in diabetes patients can result in coma and even death. Frequent testing and insulin administration can significantly reduce long-term complications of diabetes. The vast majority of sensors which are used currently for glucose monitoring are based on enzymes such as glucose oxidase or glucose dehydrogenase. These enzyme-based sensors are simple to use and have relatively high sensing selectivity. They are widely used for one-time measurement of blood-glucose concentrations ex vivo. However, among the many drawbacks of enzyme-based sensors are that they are costly and have a short life time. The inherently unstable enzyme must be protected from extreme conditions during manufacturing and storage in order to preserve its catalytic activity. In addition, there have been a number of problems associated with the use of enzymes in implantable sensors used in systems for continuously monitoring blood-glucose levels in vivo, among them the fact that enzymes can elicit an immune response and are not stable to most sterilization methods.

The one-time or 'spot' measurement of blood-glucose concentration ex vivo is also not optimal, as it requires collection of a blood sample, usually obtained by pricking the finger, which must be done at least several times each day. To avoid the need to subject the patient to this painful process for glucose monitoring, much effort has gone into identifying alternative sources for samples, such as subcutaneous tissue fluid, urine or saliva instead of blood, and for identifying less-painful and more efficient ways to obtain these samples, such as by transdermal extraction or using very thin needles. The development of new, highly sensitive and miniaturizable glucose monitoring technology will make some of these alternative methods more feasible for use at home by patients.

Continuous real time measurement of glucose concentrations is most desirable because it can be used for close monitoring and treatment. Studies indicate that medical outcomes are improved by more frequent, smaller insulin pulses. Continuous monitoring of glucose can also form part of a fully automatic insulin delivery system. A number of different sensor configurations have been proposed for use in either ex vivo or in vivo monitoring systems. Continuous glucose monitoring systems are described in a number of publications, for example by E. Wilkins and M. G. Wilkins (*J. Biomed. Eng.* 1983, Vol. 5, October, pp. 309–315) and J. Pickup (*TIBTECH*, July, 1993, Vol. 11, pp. 285–291).

Existing glucose sensing technologies exploit the ability of certain enzymes to selectively recognize glucose and catalyze a chemical reaction (Pickup, *J. Trends in Biotechnology*, 11, 285–291, (1993)). Many, for example, recruit glucose oxidase to catalyze the oxidation of glucose to gluconic acid and hydrogen peroxide, with electrochemical measurement of the latter. Potentiometric monitoring of gluconic acid production using a pH electrode or a field effect transistor (FET) is also possible. The enzyme-based sensors are simple to use and have relatively high sensing selectivity. They are widely used for one-time measurement of blood-glucose concentrations ex vivo. However, the enzyme system also has numerous disadvantages. These problems include high cost, difficulty in manufacturing, stability, both in ex vivo and in in vivo implantable devices (Alva et al. "Glucose-Oxidase Immobilized Electrode for Potentiometric Estimation of Glucose," *Biosensors and Bioelectronics* 6, 663–668, (1991); Shulga et al. "An Alternative Microbiosensor for Hydrogen-Peroxide Based on an Enzyme Field-Effect Transistor with a Fast-Response,"*Ana-* lytica Chimica ACTA 296, 163–170, (1994)). Also, the enzymes cause immunological responses and are difficult to sterilize for long term, continuous, real time measurement of glucose concentrations in vivo (Kerner et al. W., Kiwit, M., Linke, B., Keck, F. S., Zier, H. and Pfeiffer, E. F. "The Function of a Hydrogen Peroxide-Detecting Electroenzymatic Glucose Electrode is Markedly Impaired in Human Sub-cutaneous Tissue and Plasma," *Biosensors and Bioelectronics* 8, 473–482, (1993)). There is a need to develop sensitive and miniaturizable glucose monitoring devices which will make alternative methods of sample collection, such as from subcutaneous tissue fluid, more feasible for use at home by patients. The development of non-enzymatic approaches to glucose sensing is necessary in order to provide more effective management of diabetes, both for spot monitoring of glucose concentrations as well as for in vivo continuous monitoring.

A few nonenzymatic methods for measuring glucose have been proposed as alternatives to the above-described enzyme-based devices. U.S. Pat. No. 5,217,691 describes the use of boronic acids for the semiquantitative colorimetric determination of glucose. U.S. Pat. No. 4,371,374 discloses separating and quantitating glycosylated amino acids, peptides or mixtures thereof by treating a urine sample with a suitable boronic acid to complex the glycosylated compounds, separating them and analyzing the separated complexed material. U.S. Pat. No. 5,503,770 discloses a fluorescent boronic acid conjugate which emits fluorescence upon binding to saccharides. U.S. Pat. No. 5,244,562 discloses switching devices coated with a polymer imprinted with glucose and boronic acid.

Although some of the above-described sensors have shown promise, none have been found to be entirely satisfactory. In particular, the formation of covalent boronic acid-sugar complexes require several minutes to reach equilibrium, making their use in glucose sensors less attractive. There is a continuing need to develop robust sensor systems which can be used to accurately, simply and rapidly measure the amount of a particular sugar, amino acid or related compound which is present in solutions and other environments. The need is particularly apparent with respect to ex vivo and in vivo glucose determinations which are critical in medical diagnosis and treatment of various metabolic disorders, including diabetes. There is also a strong need to develop robust sensor technology for real-time monitoring of sugars, amino acids and other metabolites in manufacturing process environments.

SUMMARY OF THE INVENTION

In accordance with the present invention, sensors and systems are presented which are well-suited for use in measuring the presence of a variety of sugars, amino acids and other metal-complexing compounds (target molecule) in solutions. One aspect of the invention is based in part on the discovery that certain metal complexes will chelate sugars and other molecules in alkaline media and can either be used alone, in solution, attached to a suitable support surface, or embedded in a polymer to provide a selective sensing material which releases a proton when the target molecule binds to the metal complex. The release of protons in the sensing material provides a simple, accurate and easily detected indirect measurement of target molecule concentration in the solution.

Another aspect of the present invention is based on the discovery that certain metal complexes which contain substitutable or exchangeable ligands may be used in a method for making soluble and polymeric metal complexing materials suitable for measuring the concentrations of various analytes in solution. These materials are capable of generating protons, hydroxide ions and/or releasing detectable ligands when ligands in the metal complexes are exchanged with targeted analytes. By monitoring the pH changes of the solution or release of detectable ligands, the concentration of the analytes can be determined. Metal complexes with exchangeable ligands can be tailored so that only certain compounds, with both the right metal binding groups and the right binding strength, can cause the release of protons, hydroxide ions or other ligands upon binding to the metals. The analytes that can be targeted by this approach include sugars, aminosugars, polyols, amino acids, amino alcohols, $\alpha$-hydroxyl carboxylic acids, ions such as carbonate, phosphate and sulfate, and gaseous species, such as CO and NO, that have the ability to undergo ligand substitution on the metal complexes. In combination with various methods for measuring pH changes or the detectable ligand concentrations, these metal complexing materials can be used for chemical sensing and monitoring applications.

As a feature of the present invention, the metal complexes are preferably attached or embedded in a solid support to provide both anchoring of the complexes and positioning of the metal ions to increase selectivity of the target binding interactions. Attachment or incorporation of the metal complexes in a porous solid support can also reduce fouling of the sensor from other components in the biological sample (e.g. proteins) and provide selectivity in terms of molecular size. The sensor is especially well-suited for use in measuring the concentration of glucose in blood or serum and other bodily fluids. However, the sensor, when appropriately configured, is suitable for measuring the concentration of a wide variety of other sugars and chemically-related compounds that also bind the metal complexes.

As another feature of the present invention, the metal complex contains a polymerizable functionality, which allows it to be copolymerized with other monomers and crosslinking agents to provide incorporation of the metal complex into a polymer support matrix. The copolymerization may further be conducted with the target molecule or another molecule (referred to as the template) bound to the polymerizable metal complex to improve the polymerization process and to provide imprinting of the resulting polymer matrix. If the template binds only to one metal complex, polymerization in the presence of the template and subsequent removal of the bound template molecules can result in a polymer with greater shape and size selectivity for that molecule or its structural analogs. Alternatively, if the template binds more than one metal complex, the resulting imprinted polymer matrix holds and positions the metal complexes in a spatial orientation which increases the selectivity of the sensor for the template molecule or its structural analogs. In both these cases, the template serves to direct the formation of a selective polymer. It has also been discovered that the template can serve to improve the extent of polymerization, providing more rigid polymeric materials that can be obtained in the absence of the target molecule or other templates which bind the metal ions.

As a further feature of the present invention, a target molecule detection system is provided in which a signal transduction system is used to detect the protons, hydroxide ions or other easily detected ligand species which are released from the sensor metal complexes as a result of ligand exchange with the target molecule. Although any number of detection devices may be used to transduce the signal from the released ligand into an electrical or optical signal, it was found that detection systems based on changes in the solution pH caused by the proton or hydroxide ion release provided many advantages. Proton or hydroxide ion release can be detected simply and accurately by measuring changes in the pH of the solution exposed to the sensor material or other pH-sensitive properties. Alternatively, the solution may be titrated with acid base or after exposure to the sensor to maintain a constant pH. The concentration of target molecule can be determined from the pH change or the amount of acid or base required to maintain the pH.

As another feature of the present invention, specific metal ion complexes are provided which are designed for interaction with sugars and related molecules. Modification of the complexes allows them to be copolymerized with suitable monomers to form imprinted polymer sensors. The metal ion complexes are designed to 1) hold the metal ion tightly, 2) allow at least two coordination sites to be or become available for binding to the target molecule or ligand which exchanges with the target molecule. Further design features are that the chelating ligand (i.e. non-exchanging ligand) from which the metal complexes are formed can be chemically modified to 1) have a polymerizable functionality for copolymerization, or 2) have functional groups appropriate for covalent attachment to a solid surface, and 3) provide additional favorable interactions (electrostatic, hydrogen bonding, hydrophobic, etc.) which assist binding or provide selectivity towards the target molecule. The metal ion for a particular metal ion complex is chosen such that the target molecule binds the complex formed by the metal ion and chelating ligand rapidly and reversibly in the presence of the sample solution and that a proton, hydroxide ion or detectable ligand is released upon binding.

The sensors in accordance with the present invention may be used in both the ex vivo and in vivo environments. The sensors can be used in spot monitoring of target molecule concentrations, for example, as in monitoring glucose concentration in the blood, serum or subcutaneous tissue fluid sample of a diabetic patient. Alternatively, the sensor can be formulated into a continuous monitoring device for continuous measurement of target molecule levels ex vivo or in vivo, for example, as a subcutaneous implant or as part of an ex vivo continuous monitoring system for glucose using subcutaneous tissue fluid, serum or blood. The continuous sensors may be used as part of a feedback device for providing automatic dosing of insulin and other drugs which affect biood-sugar levels. The sensors in accordance with the present invention may also be used to monitor (on a spot or continuous basis) levels of sugars in manufacturing processes such as fermentations, purifications, and for product quality control, where it is desirable to know specific carbohydrate concentrations levels. Sensors in accordance with the present invention can be formulated for additional clinical and manufacturing applications, such as diagnosis of diseases or pathogens characterized by specific carbohydrates or other molecules that will bind the metal complexes and produce proton, hydroxide ion or other ligand signals. Additionally, such sensors can be formulated for monitoring important sugar or other chemical concentrations in other applications in clinical medicine, forensic science, drug testing, and manufacturing where it is important to rapidly obtain accurate measures of such concentrations.

As another feature of the second aspect of the present invention, specific metal ion complexes are provided which are designed for interaction with sugars and related molecules at, near or slightly above physiological pH. This feature is desirable for monitoring glucose concentrations in biological samples. The high buffer capacity of biological samples at physiological pH reduces the sensitivity of potentiometric sensors. The buffer capacity of human interstitial fluid reaches a minimum near pH 8. Sensor materials in accordance with the present invention function well at pH's of around 8 so that the minimum buffer capacity of interstitial fluid may be exploited analytically.

The above described features and attendant advantages of the present invention will become better understood by reference to the following detailed description when taken in conjunction with the accompanying drawings.

BRIEF DESCRIPTION OF THE DRAWINGS

FIGS. 1–15 relate to the first aspect of the present invention wherein metal complexes bind to target molecules with the resultant release of a proton. FIGS. 16–29 relate to the second aspect of the present invention wherein a ligand bound to the metal complex is exchanged with the target molecule resulting in the release of hydroxide ion or other ligand species.

FIGS. 1$a$–$h$ are diagrammatic representations showing exemplary ligands in their free state or in the form of metal complexes and possible structures as bound to glucose.

FIG. 2 is a diagrammatic representation of an exemplary synthesis of a preferred sugar binding sensor polymer wherein the polymer is a macroporous solid which is formed by co-polymerization of a polymerizable copper complex and crosslinking agent.

FIG. 3 is a diagrammatic representation of an exemplary synthesis of a preferred sugar binding sensor polymer wherein the selectivity of the sensor is increased by imprinting the polymer with the sugar that is to be detected or its analog.

FIG. 4 is a schematic representation of an exemplary sugar sensor system in accordance with the present invention.

FIG. 5 is a schematic representation of a sensor comprising a field effect transistor (FET) detector and utilizing an imprinted matrix in accordance with the present invention.

FIG. 6 is a schematic representation of an exemplary implantable (subdermal) continuous glucose monitoring system utilizing fluorescence detection and a microporous sensor material incorporating pH-sensitive fluorescent probe molecules.

FIG. 7. is a graph showing change in pH resulting from sequential addition of cis-diol (1,4-anhydroerythritol) to solutions of four different metal complexes at initial pH=12.0. In accordance with the present invention, the concentration of an unknown sample of the cis-diol can be determined by adding a known quantity (sample volume) to one of the metal complexes, measuring the resulting depression in pH and comparing that value to these calibration curves prepared using known quantities.

FIG. 8 is a graph showing change in pH resulting from sequential addition of Me-β-D-Glc to solutions of four different metal complexes at initial pH=12.0. In accordance with the present invention, the concentration of an unknown sample of Me-β-D-Glc can be determined by adding a known quantity to one of the metal complexes, measuring the resulting depression in pH and comparing that value to these calibration curves prepared with known quantities.

FIG. 9 is a graph depicting the results of a pH static titration with cis-diol (1,4-anhydroerythritol). The graph shows the amount of NaOH required to maintain the pH of the Cu(TACN) metal complex solution at four initial pH values. In accordance with the present invention, the concentration of an unknown sample of cis-diol can be determined by adding a known quantity to Cu(TACN), measuring the amount of NaOH required to maintain constant pH and comparison to these calibration curves prepared using known quantities.

FIG. 10 is a graph depicting the results of a pH static titration with Me-β-D-Glc, showing amount of NaOH required to maintain the pH of the Cu(TACN) metal complex solution at four initial pH values. The concentration of an unknown sample of Me-β-D-Glc can be determined by adding a known quantity to Cu(TACN), measuring the amount of NaOH required to maintain constant pH and comparison to these calibration curves prepared using known quantities.

FIG. 11 is a graph showing the results of a titration of an exemplary sensor polymer (Polymer I) with glucose at pH 11.50, 10.50 and 10.25. The graph shows total released proton concentration vs total glucose concentration.

FIG. 12 is a graph showing the results of static titration of exemplary sensor polymers (Polymers II, III and IV) at a pH of 10.25. The graph shows total released proton concentration vs total glucose concentration.

FIG. 13 is a graph showing a comparison of protons released from exemplary sensor polymers II and IIe. The graph shows total released proton concentration vs total glucose concentration.

FIG. 14 is a graph showing a comparison of protons released from exemplary sensor polymers IV and IVe. The graph shows total released proton concentration vs total glucose concentration.

FIG. 15 is a graph showing a comparison of glucose and glucosamine binding to polymer IV at pH 10.25.

FIG. 16 shows pH changes measured upon addition of a pH 8.5 solution of D-glucose to a 1 mL solution of 2 mM [Cu(1,10-phenanthroline)(NO$_3$)$_2$], starting at pH 8.5, 25° C.

FIG. 17 shows the results of pH static titrations of D-glucose added to [Cu(N$_2$O-9-ane)Cl$_2$], [Cu(N$_2$S-9-ane)Cl$_2$] and [Cu(TACN)Cl$_2$] at 25° C. and at pH 8.5. A 2.0 mL solution of 10 mM Cu(II) complex and 150 mM NaCl was placed a titration vessel (719 S Titrino, Brinkman Instruments, Westbury, N.Y.), and the pH was adjusted to 8.50 using concentrated NaOH solution. The glucose solution (0.500 M, pH 8.5, NaCl concentration was 150 mM) was added to the stirred suspension in 2.5 μL or larger increments, and the amount of 0.010 N NaOH required to maintain the pH constant was noted.

FIG. 18(a) depicts compounds 1 and 2 which are representative metal complexes that have exchangeable ligands. They are prepared by combining Cu(TACN) with ligands 3 and 4, respectively, under appropriate conditions.

FIG. 19 shows ligand exchange reactions of sensor complexes 1 and 2 with representative metal binding analytes: amino alcohol (6), α-hydroxyl carboxylic acid (8), amino acid (10) and diol (12). Protons or hydroxides are generated in these reactions (equation 1 to equation 5). Only the forward reaction is indicated.

FIG. 20 depicts exemplary nitrogen-based multidentate ligands. R is H or a polymerizable functional group.

FIG. 21 depicts exemplary ligands for metal complexes suitable for glucose binding under slightly alkaline conditions.

FIG. 22 shows an exemplary preparation of ligand-co-immobilized metal complexing polymer. A polymerizable analog of cis-diol (33) is allowed to form a complex (34) with Cu-Styryl-TACN (32) (Equation 1). This complex is then incorporated into polymers (35) (Equation 2). A substrate such as glucosamine (36) can displace the cis-diol portion of the polymer and generate hydroxide (Equation 3). However, the cis-diol will remain close to the metal ion after it is displaced. It can therefore rebind the Cu(II) complex (and consuming a hydroxide) when the glucosamine concentration decreases.

FIG. 23 shows the results of static titration of pH 10.25 D-glucose solution to the carbonate pre-treated Cu(TACN)-containing polymer suspension (0.100 g polymer, 0.034 mmol Cu$^{2+}$; pH=10.25) in a titration vessel (719 S Titrino, Brinkman Instruments, Westbury, N.Y.) at 25° C. The glucose solution was added to the stirred suspension in 2.5 μL or larger increments, and the amount of 0.100 N NaOH required to maintain the pH constant was recorded.

FIG. 24 shows the results of pH static titration of pH 10.25 D-glucosamine solution to the carbonate pre-treated Cu(TACN) containing polymer suspension (0.100 g polymer, 0.034 mmol Cu$^{2+}$; pH=10.25) in a titration vessel (719 S Titrino, Brinkman Instruments, Westbury, N.Y.) at 25° C. The glucosamine solution was added to the stirred suspension in 2.5 μL or larger increments, and the amount of 0.100 N NaOH required to maintain the pH constant was recorded.

FIG. 25 shows pH changes measured upon addition of porcine plasma to carbonate-saturated Cu(TACN) polymer suspension at pH 11.25, 25° C. Three porcine plasma samples with glucose concentrations of 6.88 mM, 22.6 mM and 44.8 mM were prepared and adjusted to pH 11.25. Each sample (250 μL) was then added to a 1 mL pH 11.25 polymer-carbonate (80 mM) suspension (50 mg polymer, ~0.01 7 mmol Cu(II) sites). pH changes of the mixed suspensions were noted.

FIG. 26 shows the results of pH static titrations of pH 10.25 lactic acid solution to the cis-diol pre-treated Cu(TACN)-containing polymer suspension (0.100 g polymer, 0.034 mmol Cu$^{2+}$; pH=10.25) in a titration vessel (719 S Titrino, Brinkman Instruments, Westbury, N.Y.) at 25° C. The lactic acid solution was added to the stirred suspension in 2.5 μL or larger increments, and the amount of 0.100 N HCl required to maintain the pH constant was recorded. The total concentration of hydroxide released is proportional to the lactic acid added, from a concentration of 0 mM to 20 mM.

FIG. 27 shows the results of pH Static titrations of pH 10.25 D-glucosamine solution to the cis-diol pre-treated Cu(TACN)-containing polymer suspension (0.100 g polymer, 0.034 mmol Cu$^{2+}$; pH=10.25) in a titration vessel (719 S Titrino, Brinkman Instruments, Westbury, N.Y.) at 25° C. The glucosamine solution was added to the stirred suspension in 2.5 μL or larger increments, and the amount of 0.100 N HCl required to maintain the pH constant was recorded.

FIG. 28 shows pH changes measured upon addition of pH 10.25 L-alanine solution to the pH 10.25 suspension of polymer (100 mg, ~0.034 mmol Cu$^{2+}$ sites) in 1 mL of 1.0 M or 0.25 M 1,4-anhydroerythritol (cis-diol) solution at 25° C. After each addition of L-alanine, pH changes of the mixed suspensions were noted.

FIG. 29 shows the titration of D-glucose into Cu(TACN) Cl$_2$ solution (0.200 mmol+0.400 mmol NaCl in 2 mL) in a titration vessel (719 S Titrino, Brinkman Instruments, Westbury, N.Y.) at 25° C. and at pH 10.00. A 0.50 M glucose solution was added to the stirred solution in 10 μL or larger increments, and the chloride electrode potential of the Cu(TACN)Cl$_2$ solution was recorded after each titration.

DETAILED DESCRIPTION OF THE INVENTION

Figure 1A:
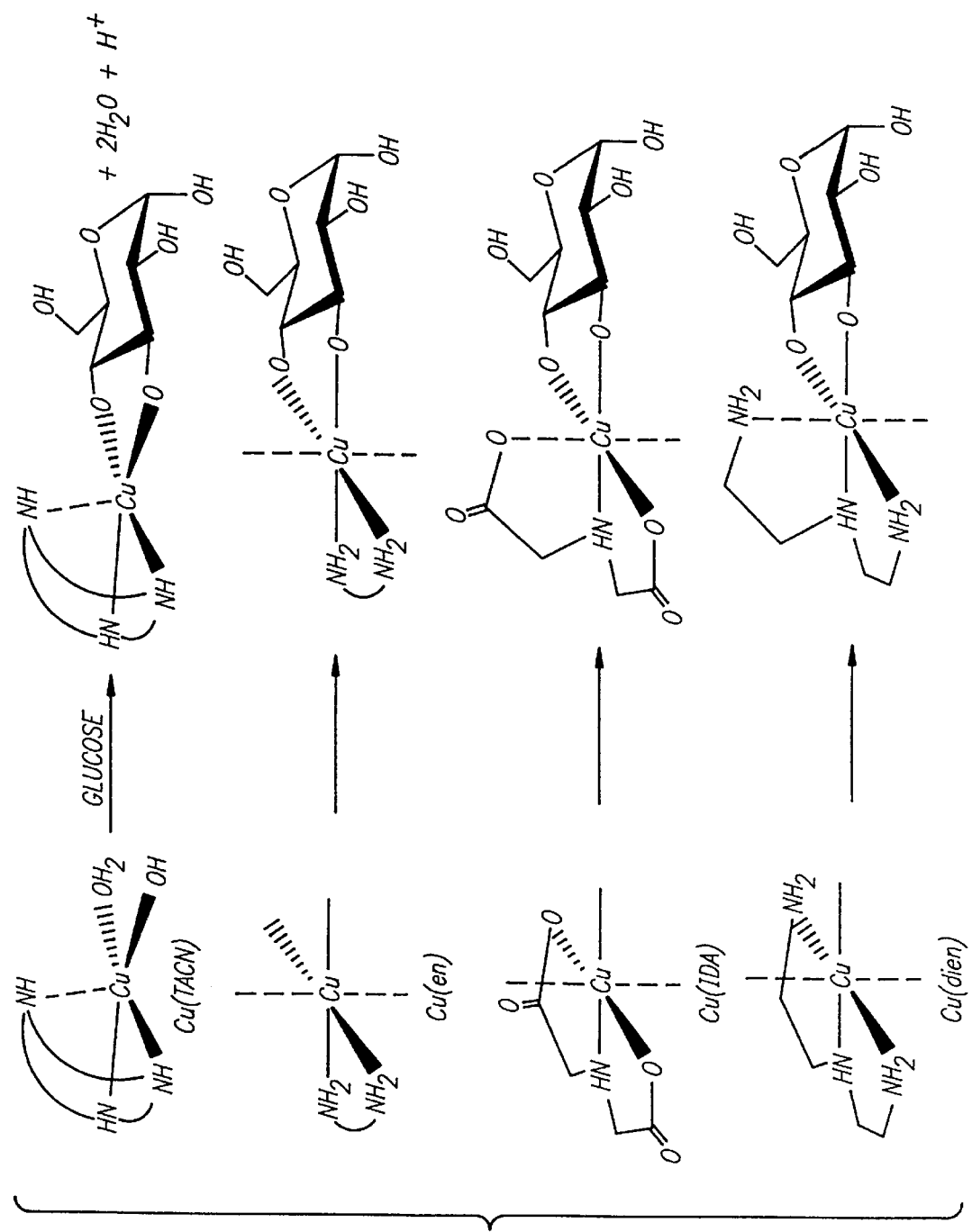

The following description is divided into two parts. The first part is directed to a description of metal complexes wherein the target molecule binds to the metal complex with the resultant release of a proton. The second part is directed to the same or similar metal complexes which further include an exchangeable ligand releasably bound thereto. Protons, hydroxide ion or other species are released when the target molecule binds to the metal complex and displaces the ligand.

Metal Complex/Target Molecule Binding

The sensors in accordance with the present invention may be used to detect and measure the presence of a wide variety of target molecules (e.g. sugars and related compounds) in solution. The sensors are suitable for detecting sugars such as glucose, mannose and other monosaccharides, sialic acid, lactic acids, aminosugars such as glucosamine, disaccharides, trisaccharides, oligosaccharides, sugar-amino acids, sugar-peptides and glycoproteins. Other target molecules can also be measured using this sensor. Exemplary target molecules include glycerol, dopamine, catechols, ascorbic acid, polyols, diols such as 1,4-anhydroerythritol, and ethyleneglycol. The general characteristics of or requirement for a suitable target molecule is that it must be able to bind the metal complex and release a proton when used at an appropriate pH. Sensors which are capable of measuring the concentration of glucose in biological samples are preferred because of the importance of glucose in the diagnosis and treatment of diabetes and other disorders. The concentration range which is typically of interest in biological samples is 0–25 mM.

The sensors may be used to detect the presence of target molecules in a wide variety of different aqueous and aqueous-organic solutions. The only requirement is that the immediate environment of the metal complexes be at a pH that will provide adequate binding between the metal complexes in the sensor and the target molecule of interest and will release a proton(s). The pH of the environment can be tailored either by adjusting the sample pH or through the choice of polymer support, co-monomers or crosslinking agents for copolymerization, or by the addition of appropriate counterions. Alkaline solutions are those having a pH of above 7.0. The upper limit for solution pH is not particularly critical provided that the solution is not so alkaline that the target molecules or sensor components are adversely affected. In general, it is preferred that the immediate environment around the metal complex have a pH of between 8 and 13. The optimum values of pH will depend on the buffer capacity of the sample and the sensor's response at that pH, among other factors. Changes in the local pH resulting from binding to the target molecule are easier to measure at pH values where the sample has little buffering capacity. Similarly, the sensor will be more sensitive to target molecule concentration at pH values where the metal complex binds the target molecule most tightly. The optimal pH will also depend on the particular metal complex and target molecule.

The ability of sugars and other molecules with multiple hydroxyl groups to form chelate complexes with metal ions in aqueous solution is well known (general review by: Whitfield, D. M. et al., "Metal coordination to carbohydrates. Structures and Function," *Coord. Chem. Reviews* 122, 171–225 (1993) and Angya, S. J. Complexes of Metal Cations with Carbohydrates in Solution, in "*Advances in Carbohydrate Chemistry and Biochemistry*", Academic Press, Inc. 1989, pp. 1–4.). The complexation of Cu(II) with various sugar α-amino acids is described by (M. Angeles Diaz-Diez et al., *Transition Met. Chem.* 20, 402–405 (1995)). Sugar-α-amino acid will also form complexes with Co(II), Ni(II), Zn(II) and Cd(II) (M. Angeles Diaz-Diez et al., *J. Inorg. Biochem.* 56, 243–247 (1994)). Klufers and Schuhmacher describe complex formation between sugar alcohols and Cu(II) (Klufers, P. and J. Schuhmacher, *Angew. Chem. Intl. Ed. Engl.* 33, 1742–1744 (1994)). Cu(II) complexes with various amino sugars are described by Kozlowski, H. et al., *Carbohydrate Res.* 197,109–117 (1990). Weaker complexes are formed with Ni(II) and Co(III). Cuprammonium-glycoside complexes are described by Reeves and Bragg, *J. of Org. Chem.* 26, 3487–3489 (1961).

Vanadium complexes of various sugars are described by (Sreedhara, A. et al., *Carbohydrate Res.* 264,227–235 (1994)). Complex formation between D-xylo 5-hexulosonic acid and molybdate and tungstate is described by (Caldeira, M. M. et al., *Inorg. Chim. Acta* 221, 69–77 (1994)). The ability of Al(III) to form complexes with glucose and glucuronic acid is reported by (Tonkovic, M. and Bilinski, H., *Polyhedron* 14, 1025–1030(1995)). Fe(III) complexes with eighteen different sugar-type molecules are reported by (Nagy, L. et al., *Inorg. Chim. Acta* 124, 55–59 (1986). D-Glucuronic acid forms complexes with uranium (Tajmir-Riahi, H. A., *Inorg. Chim. Acta* 119, 227–232 (1986)), Ba(II), Mg(II) and Sr(II) (Tajmir-Riahi, H. A., *J. Inorg. Biochem.*, 24, 127–136 (1985)).

Glucose complexation to a variety of metals has been described: Cu(II), Ba(III) (Sharareh, S. and E. Wilkins, *J. Environ. Sci. Health* A26(7), 1021–1032 (1991), Mg(II), Ca(II) (Tajmir-Riahi, H.-A., *Carbohydrate Res.* 183, 35–46 (1988), Fe(III) (Geetha, K. et al., *Carbohydrate Res.* 271, 163–175 (1995)).

Furthermore, it is known that carbohydrates will bind reversibly to metal complexes immobilized on surfaces during ligand-exchange chromatographic separations. For example, carbohydrates form complexes with electrostatically immobilized rare earth (Tb(III)) and uranyl ions at alkaline pH (Stefannson, M., D. Westerlund, "Ligand exchange chromatography of carbohydrates at alkaline pH: effects of mobile phase additives and temperature," *J. Chromatogr. Sci.* 32,46–49 (1994)). Chromatographic separation of hexoses, pentoses and corresponding polyols has been reported on adsorbents containing $Ca^{2+}$, $Sr^{2+}$, $Ba^{2+}$, $Pb^{2+}$, $Y^{3+}$, $La^{3+}$ and $Pr^{3+}$(Caruel, H. et al., Carbohydrate separation by ligand-exchange liquid chromatography, *J. Chromatogr.* 558,89–104(1991)).

The sensor includes specific types of metal ion complexes that bind to sugars and other molecules in alkaline aqueous solution. Metal ion complexes which may be used in accordance with the present invention should: 1) hold the metal ion tightly; and 2) allow at least two coordination sites to be or become available for binding to the target sugar or other molecule. Further useful features are that the chelating ligand from which the metal complexes are formed may be chemically modified to 1) have a polymerizable functionality for copolymerization, or 2) have functional groups appropriate for covalent attachment to a solid surface, and 3) provide additional favorable interactions (e.g. electrostatic, hydrogen bonding and hydrophobic) with the target molecule. The metal ion for a particular metal ion complex is chosen such that the target molecule binds the complex formed by the metal ion and chelating ligand rapidly and reversibly in the presence of the sample solution and that a proton is released upon binding.

Six exemplary metal complexes are shown in FIG. 1a. On the left side of FIG. 1a, the metal complexes are shown in an unbound state in alkaline aqueous solution. On the right side of FIG. 1a, the configurations of the metal complexes when they are bound to glucose are shown. Exemplary metal complexes include copper(II)-triazacyclononane (Cu (TACN)), copper(II)-1,4-dimethyl triazacyclononane (Cu(1, 4-dimethyl-TACN)) (not shown in FIG. 1a), copper(II)-ethylenediamine (Cu(En)), copper(II)-propylenediamine (Cu(II)-PDN)), copper(II)-iminodiacetate (Cu(IDA)), copper(II)-diethylenetriamine (Cu(Dien)), copper(II)-1-oxa-4,7-diazacyclononane (Cu(II)(N$_2$O-9-ane)) and copper(II)-1-thia-4,7-diazacyclononane (Cu(II)(N$_2$S-9-ane)). Derivatives of the above compounds may also be used including the alkylated derivatives.

Preferred exemplary metal complexes are those which have the formula

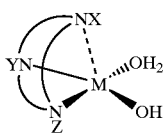

wherein M is copper or iron; X is H or a functional group selected from styrene, methacrylate, acrylate, vinyl ether, vinyl acetate, trialkoxysilane, dialkylchlorosilane, epoxy and alkylhydroxyl or alkylamine groups having from 1 to 3 carbon atoms. Y is H or a functional group selected from styrene, methacrylate, acrylate, vinyl ether, vinyl, vinyl acetate, trialkoxysilane, dialkylchlorosilane, epoxy and alkyl, alkylhydroxyl or alkylamine groups having from 1 to 3 carbon atoms. Z is H or a functional group selected from styrene, methacrylate, acrylate, vinyl ether, vinyl acetate, trialkoxysilane, dialkylchlorosilane, epoxy and alkyl, alkyihydroxyl or alkylamine groups having from 1 to 3 carbon atoms. One of the nitrogens in the formula can be replaced by an oxygen or sulfur atom to make additional preferred metal complexes. Examples are the Cu(II)(N$_2$O-9-ane) and Cu(II)(N$_2$S-9-ane) shown in FIG. 1a (where X,Y,Z=H).

Additional exemplary metal complexes are listed below and classified by their coordination number and the donor atoms. Polymerizable functional groups for these complexes are also selected from styrene, methacrylate, acrylate, vinyl, vinyl ether, vinyl acetate, trialkoxysilane, dialkylchlorosilane and epoxy.

Class I (Nitrogen-based bidentate ligands)

Ethylenediamine (En), which can form a five-membered ring with metal ions by chelation, shows relatively strong complexation with metal ions (M) such as Cu$^+$, Cu$^{2+}$, Co$^{3+}$, Ni$^{2+}$, Fe$^{3+}$ and Hg$^{2+}$. The geometry of the complexes is either square planar, tetrahedral or octahedral. Even when there is no vacant coordination site left in the complex, the deprotonated sugar is able to replace one of ethylene ligands at the equatorial positions under strongly basic conditions. The coordinating amine can be either primary or secondary or even tertiary, as long as steric strain is minimized. Polymerizable functional groups can be attached either through nitrogen or carbon atoms. Other diamines including linear and macrocyclic forms can serve the same purpose, as long as they can bind the metal ion to form stable metal complexes with the features listed above. Exemplary chemical formulas for this class of complexes are set forth in FIG. 1b where R is the polymerizable functional group. The binding of the complexes to glucose is also shown wherein "〰〰" represents glucose.

Class II (Nitrogen-based linear tridentate ligands)

Linear triamines bind metal ions more tightly than the bidentate open chain diamines. The ligands which are able to form either five-membered ring or six-membered rings are suitable. Facial and meridional coordination stereoisomers are commonly observed for the octahedral complexes for most metal complexes. The negatively-charged oxygens from sugar molecules are able to displace one of the ligands to a bind metal ion at its equatorial positions. Again, polymerizable functional groups can be incorporated at the nitrogen or carbon atoms. In the following example, only derivatization on the nitrogen is shown.

Exemplary metal complexes belonging to this class are shown in FIG. 1c. The chemical formula for the ligand alone is shown along with exemplary formulas for the ligand bound to a metal ion to form the metal complex. An exemplary binding of the metal complex to glucose is also shown. Derivatization on the nitrogen atom only is shown. As mentioned above, derivatization on the carbon atom is also possible. In FIG. 1c, M includes the same metal ions as the Class I complexes and R', R" is H, CH$_3$ or another other functional group that confers greater stability to the complex. For a polymerizable complex, one or more of the R groups is selected from styrene, methacrylate, acrylate, vinyl, vinyl ether, vinyl acetate, trialkoxysilane, dialkylchlorosilane or epoxy.

Class III (Nitrogen-based linear tetradentate ligands)

Figure 1D:
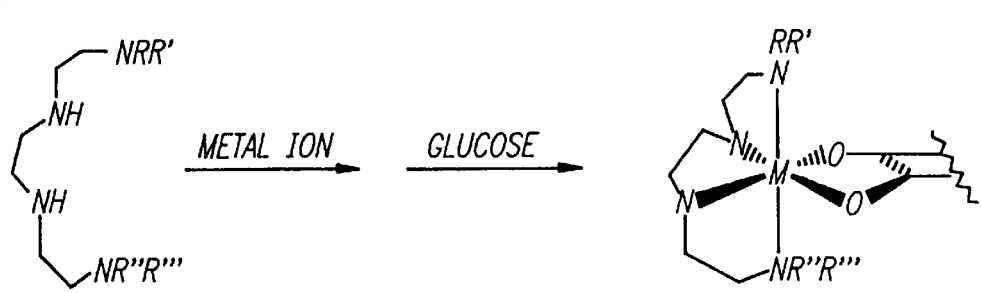

The structure of exemplary ligand from this class is shown in FIG. 1d. The ligand structure is shown as well as the structure of the ligand after binding to a metal ion (M) and subsequent binding to glucose (〰〰). The four nitrogen atoms can be either primary or secondary or tertiary amines. Ethylene units or propyl units between coordinating nitrogens are suitable. R, R', R", R'" is H, CH$_3$ or another other functional group that confers greater stability to the complex. For a polymerizable complex, one or more of the R groups is selected from styrene, methacrylate, acrylate, vinyl, vinyl ether, vinyl acetate, trialkoxysilane, dialkylchlorosilane or epoxy.

Class IV (Nitrogen-based tridentate macrocycles)

Ligands used in the metal complexes can be improved by making them more rigid, with the coordinating groups correctly preoriented for coordination to the metal ions. Macrocyclic rings provide this advantageous feature. The tridentate macrocyclic ligands display strong complexation with most transition metal ions, chelating in a facial arrangement with two equatorial sites open for sugar binding. As before, structural variations on the ring can be made through the carbon or nitrogen atoms.

A preferred ligand for the metal complex is triazacyclononane. This ligand tightly complexes metal ions such as copper(II), leaving coordination sites appropriately positioned for sugar chelation. The binding of this type of ligand to a metal ion is shown in FIG. 1a and in more detail in FIG. 1e. The stability of triazacyclononane under alkaline conditions can be improved by alkylating the nitrogens. A preferred metal ion complex is therefore a polymerizable derivative of di-alkylated triazacyclononane. The triazacyclononane can be methylated, for example, at the 1 and 4 nitrogens (synthesis shown in Example 2), while a polymerizable group can be added at the remaining unalkylated nitrogen (using the procedures of Example 3).

Figure 1E:
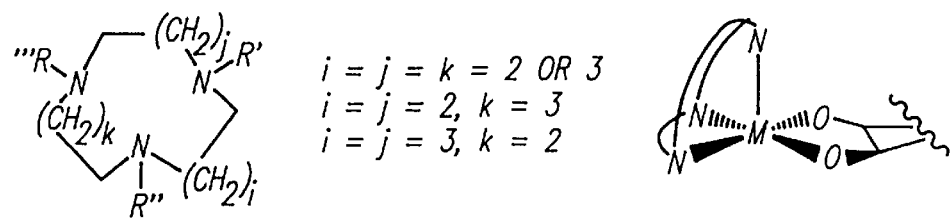

Referring to FIG. 1e, M is a metal ion as described above and R, R', R" is H, CH$_3$ or another other functional group that confers greater stability to the complex. For a polymerizable complex, one or more of the R groups is selected from styrene, methacrylate, acrylate, vinyl, vinyl ether, vinyl acetate, trialkoxysilane, dialkylchlorosilane or epoxy.

Class V (Nitrogen-based tridentate with pendant arm(s) able to form additional interactions with sugar molecules)

This class of ligands is very similar to the ligands in Class III. The only difference is that the functional groups with hydrogen bonding capability, such as hydroxyl, phosphinic, amide and carboxylic acid groups, are introduced to the nitrogen atoms. When the sugar molecule binds to the metal complex, the close proximity of hydrogen donors (acceptors) on the pendant arms can provide additional hydrogen bonding interactions besides metal-hydroxyl interactions. The chemical structure of this type of ligand and the resulting metal complex as bound to glucose is shown is FIG. 1f.

Figure 1F:
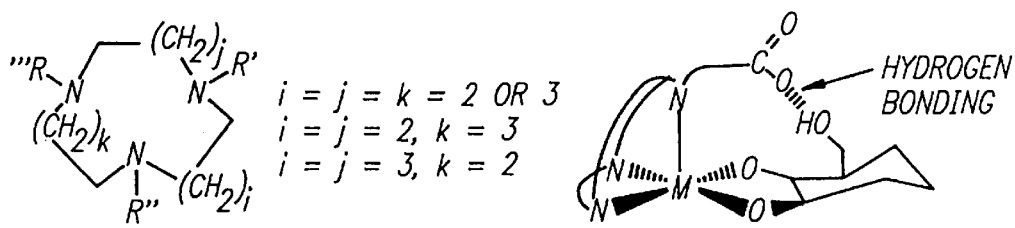

In FIG. 1f, one of the R groups can be hydroxyl, phosphinic, amide or carboxylic acid group. Alternatively, aromatic moieties or alkyl chains are incorporated on the ligands to provide hydrophobic interactions with sugar molecules. Other favorable interactions (e.g. electrostatic, etc.) can be envisioned, based on the target molecule to be recognized. For a polymerizable complex, one or more of the R groups is selected from styrene, methacrylate, acrylate, vinyl ether, vinyl acetate, trialkoxysilane, dialkylchlorosilane or epoxy.

Class VI (Nitrogen-based tetradentate macrocyclic ring)

Figure 1G:
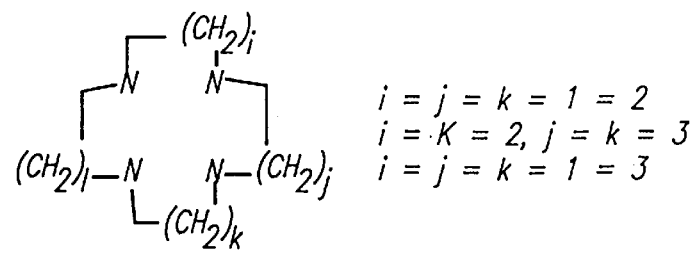

The macrocyclic ring is bigger than the tridentate macrocyclic rings. Most metals can sit in the plane consisting of four nitrogens atoms, and the conformation of these macrocyclic rings is important for the binding geometry. If four nitrogens adopt square planar geometry around the metal ion, this metal complex cannot interact with a sugar molecule effectively. If two nitrogen atoms occupy two equatorial sites and the other two atoms coordinate to metal from axial positions and leave two equatorial coordination sites available, the resulting metal complex can bind sugar molecules more efficiently. The chemical structure of this class of ligand is shown in FIG. 1g. Noncoordinating functional groups can be introduced on the rings to provide additional interactions similar to class V discussed earlier.

Class VII (Tridentate ring ligands)

Figure 1H:
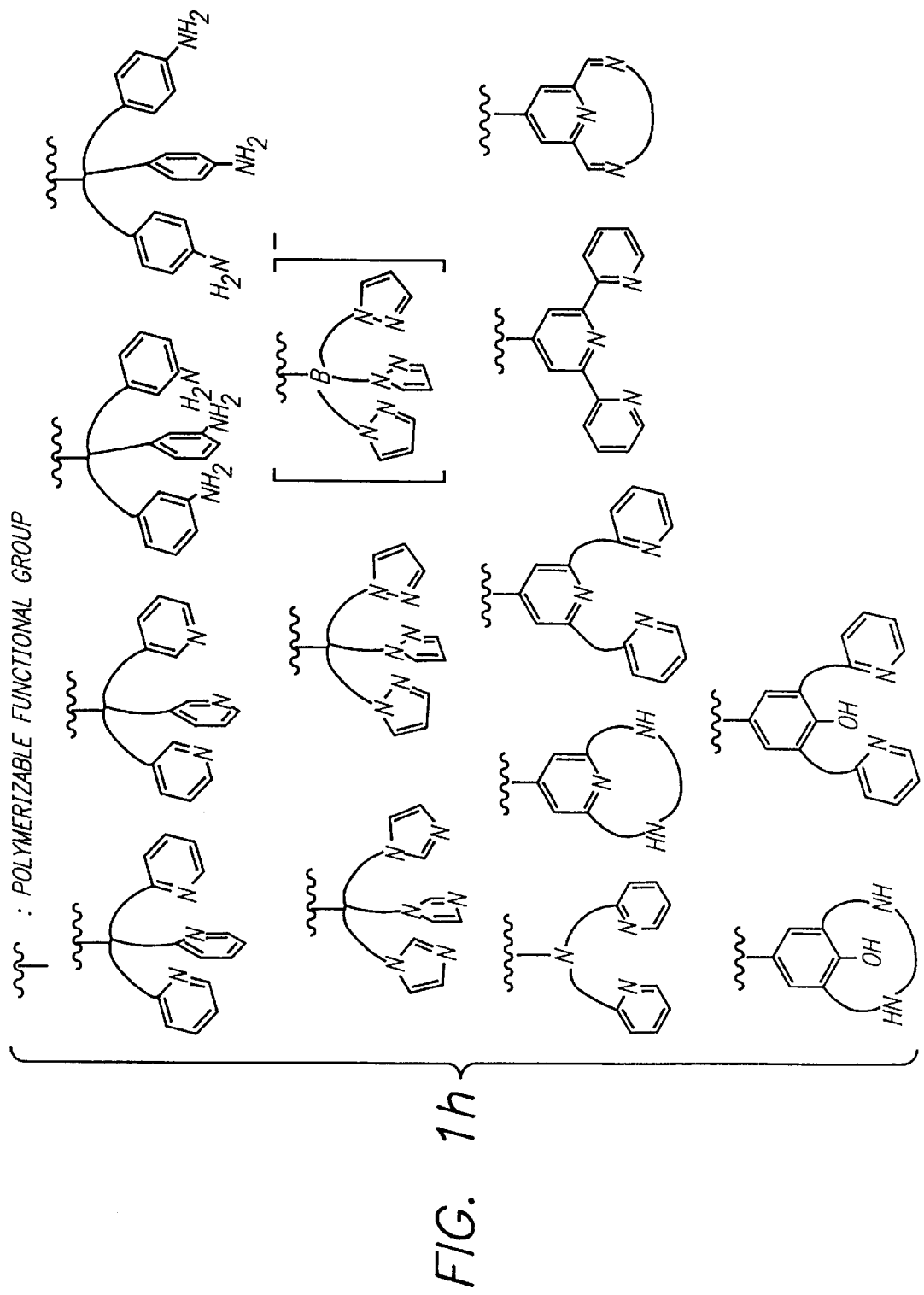

The tridentate ligands consisting of pyridine or pyrazole or imidazole rings are also suitable for forming metal complexes which may be used in detector systems in accordance with the present invention and are illustrated in FIG. 1h. The coordination geometry is similar to the saturated nitrogen donors set forth above. Other functional groups which can provide additional interactions with the target molecules can be introduced, as described previously. In FIG. 1h, "∽" is a polymerizable functional group which can be the same as the other classes. B is boron.

Complexes which utilize copper as the metal ion are preferred. However, other metal ions which may be used in certain metal complexes include lead, vanadium, iron, mercury, nickel, cobalt, aluminum, uranium, calcium, barium, yttrium and lanthanum ions.

Referring to FIGS. 1a–h, upon binding of glucose to the metal complex, a proton is released into solution. The release of protons provides an indication of the amount of sugar which is available to bind to the metal complexes. The released protons may be measured directly using proton detection equipment. It is preferred that the released protons be measured by monitoring their effect on solution pH. As is well known, release of protons into solution results in lowering of the solution pH. Accordingly, measurement of pH provides a relatively simple and straightforward method for qualitatively observing the binding reaction between sugar or other target molecule and the metal complex. This can be done, for example, using a pH electrode, field effect transistor (FET), light-addressable potentiometric sensor (LAPS), or other device which provides an electrical signal or, alternatively, using an chemical probe whose optical (fluorescence, absorption, etc.) are sensitive to solution pH. The probe then provides an optical signal which can be read to determine the sugar concentration. Other solution or material properties that are sensitive to the solution pH such as conductivity can also be measured and used to determine the target molecule concentration.

When relatively large concentrations of sugar are being measured, care must be taken to ensure that the pH does not drop significantly. Significant drops in pH may cause the binding constant between the metal complex and sugar to decrease beyond measurement. Dilution or a smaller sample size may be appropriate for very high glucose concentrations. Alternatively, static pH titration techniques can be employed, but they introduce additional complexity. Static titration involves addition of a suitable base, such as sodium hydroxide or in situ generation of base (e.g. electrochemically) to maintain a constant pH level. The amount of base which must be added to the solution to maintain a constant pH provides a direct indication of the amount of protons which are released due to sugar binding. The advantage of static titration is that the pH level remains the same so that the apparent binding constant between the target molecule and metal complex will also remain unchanged.

It is preferred that the metal complexes of the present invention be anchored to a support surface. However, the present invention does cover the use of metal complexes which are in solution and not anchored to a support. The free metal complexes may be used in solution to detect the presence of sugar in those situations where solid sensing materials are either undesirable or not practical. As will be discussed in detail below, attachment of the metal complex to ligand support structures is preferred since the support can provide the sensor with additional selectivity for the target molecule and can be used to connect the metal complexes with the appropriate proton detection system (e.g. field effect transistor (FET), light addressable potentiometric sensor (LAPS), pH-sensitive chromophore with optical wave guide pH electrode).

It is preferred that the metal complex be attached to a ligand support structure. Any number of methods may be used to attach the metal complexes, and any number of different support materials and physical forms may be utilized. Exemplary ligand support materials include silicon, glass, quartz, ceramics, organic or inorganic polymers, and zeolites and other inorganic materials. The ligand support structure can be almost any solid form which provides a surface to which the metal complex may be attached. Exemplary forms include beads, porous polymer beads, particles or membranes, plates, threads, fibers and solid-state electronic devices such as FETs or LAPS devices and the like. The metal complexes may be attached to these materials and forms covalently or noncovalently, using methods well known to those practiced in the art.

In a preferred embodiment, the metal complexes include a polymerizable moiety which allows the complex to be copolymerized with monomers and crosslinking agents to form porous polymeric materials. Polymerizable metal complexes are preferred since they can be incorporated via co-polymerization directly into the support structure. The polymer can be formulated into appropriate forms or configurations (membrane, beads, etc.) using methods well known to those practiced in the art. In addition, appropriate pH-sensitive chromophores or fluorophores can be incorporated during polymerization for optical detection of target molecule binding. The resulting polymer, whether it be in the form of a powder, micro beads or a larger structure, can be used in conjunction with a pH monitoring system as a sensor. Exemplary functional groups which are attached to the metal complex to form polymerizable metal complexes are set forth in detail above.

Exemplary monomers and cross-linkers which may be co-polymerized with the polymerizable metal complex include styrene, methyl methacrylate, 2-hydroxyethyl methacrylate, 2-hydroxyethyl acrylate, methyl acrylate, acrylamide, vinyl ether, vinyl acetate, divinylbenzene, ethylene glycol dimethacrylate, ethylene glycol diacrylate, pentaerythritol dimethacrylate, pentaerythritol diacrylate, N,N'-methylenebisacrylamide, N,N'-ethylenebisacrylamide, N,N'-(1,2-dihydroxyethy-lene)bis-acrylamide, trimethylolpropane trimethacrylate, etc. The choice of co-monomer and cross-linker will be dictated by the chemical (hydrophilicity, local pH, chemical stability, degree of crosslinking, ability to graft to other surfaces, interactions with other molecules, etc.) and physical (porosity, morphology, mechanical stability, etc.) properties desired for the polymeric sensor material.

Figure 2:
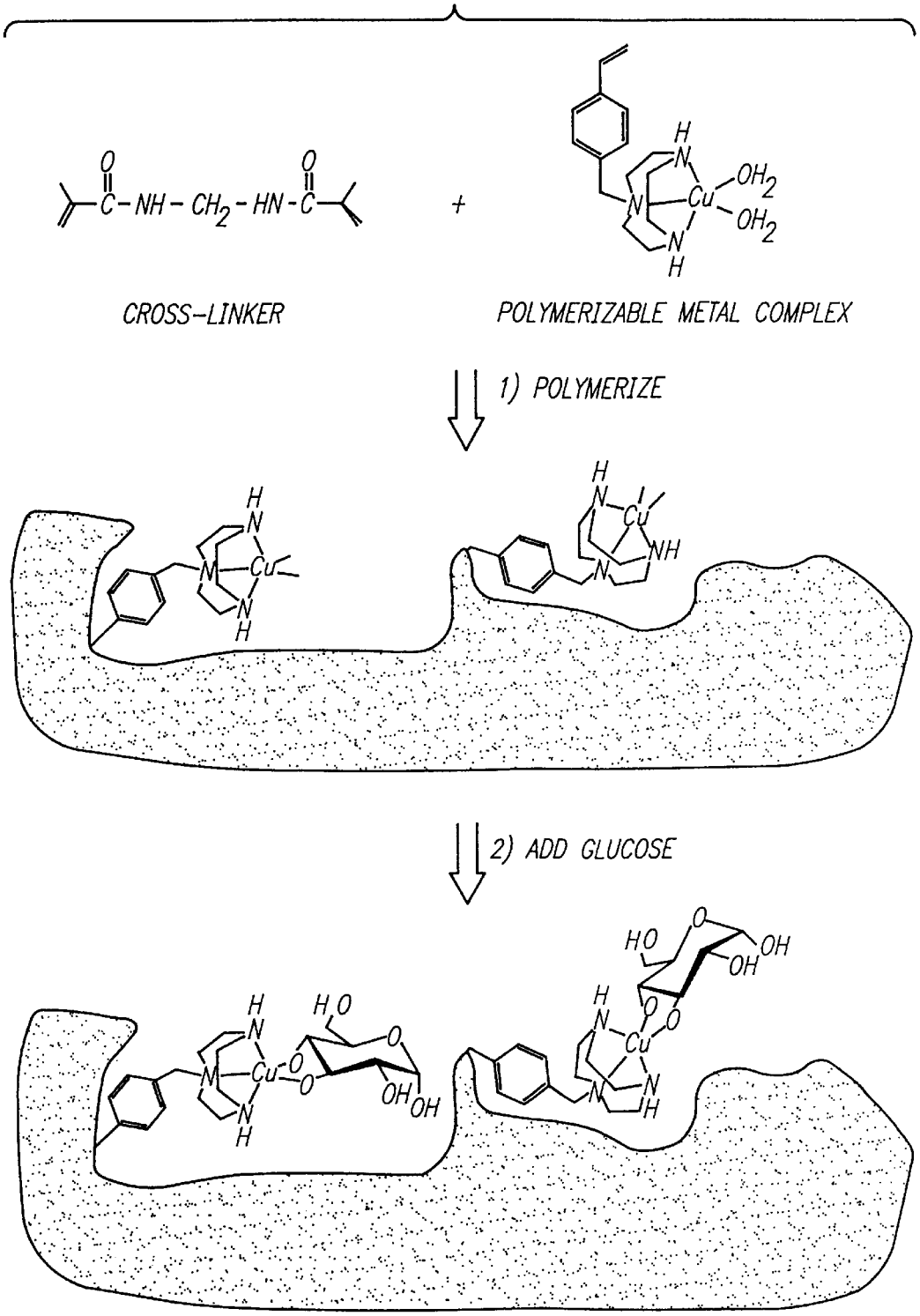

An exemplary synthesis is shown in FIG. 2 for forming a sugar sensing polymer by co-polymerization of a polymerizable copper(II) complex with a crosslinking agent to form a macroporous polymer solid. The cross-linker and polymerizable metal complex are initially polymerized (step 1) to form the macroporous polymer sensor wherein the metal complexes are exposed for interaction with glucose molecules in solution. When the polymer sensor is exposed to glucose in the sample solution (step 2), the glucose binds to the metal complex which is in turn bound by polymerization to the polymer support structure which is represented by the shaded region in FIG. 2.

The procedures and conditions which are use to copolymerize the polymerizable metal complex and cross-linking agent are conventional. The relative amounts of each monomer can be varied to achieve desired concentrations of metal complexes in the polymer support structure. Typically, the amount of chelating monomer will be on the order of 5–10% weight percent of the cross-linking monomer. The solvent, temperature and means of polymerization (e.g. free radical initiation, γ-radiation) can be varied in order to obtain polymeric materials of optimal physical or chemical features, for example, porosity, stability, and hydrophilicity. The solvent will also be chosen based on its ability to solubilize all the various components of the reaction mixture. In addition, pH-sensitive indicators such as fluorescent probes, other optical probes, or other pH-sensitive probes can be incorporated into these polymers for detection of glucose binding by optical or other methods.

Polymerizations are generally conducted in bulk solution of a polymerizable metal complex, a template molecule (if used), and a cross-linker by the free radical method. Similar methodology can be applied to surface grafting and particle coating with the polymer, as described in "Surface Grafting of Functional Polymers to Macroporous Poly (Trimethylolpropane Trimethacrylate," P. K. Dhal, S. Vidyasankar and F. H. Arnold, *Chemistry of Materials* 7, 154–162 (1995) and "Molecularly-imprinted Polymers on Silica: Selective Supports for High Performance Ligand-Exchange Chromatography," S. D. Plunkett and F. H. Arnold, *J. Chromatogr.* A 708, 19–29 (1995)).

For bulk polymerization, usually, about 5–10 weight percent of the polymerizable metal complex, 95–90 weight percent cross-linker, and 1% of a free radical initiator such as azo-bis(isobutyronitrile) (AIBN) are dissolved in an aqueous/organic mixed solvent which serves as a porogen to create a porous structure. The solution is heated at 60–70° C. for 24 hours. The resulting cross-linked polymer is cut into pieces or ground into a powder and washed thoroughly with the same solvent used for the polymerization.

Polymerizations can be carried out by a sol-gel process when an alkoxy-silane type of polymerizable metal complex is used. In this case, the alkoxysilane metal chelating monomer is mixed with tetramethoxysilane or tetraethoxysilane in aqueous solution. The sol-gel condensation can be conducted in acidic or basic conditions using procedures well known to those practiced in the art.

Figure 3A:
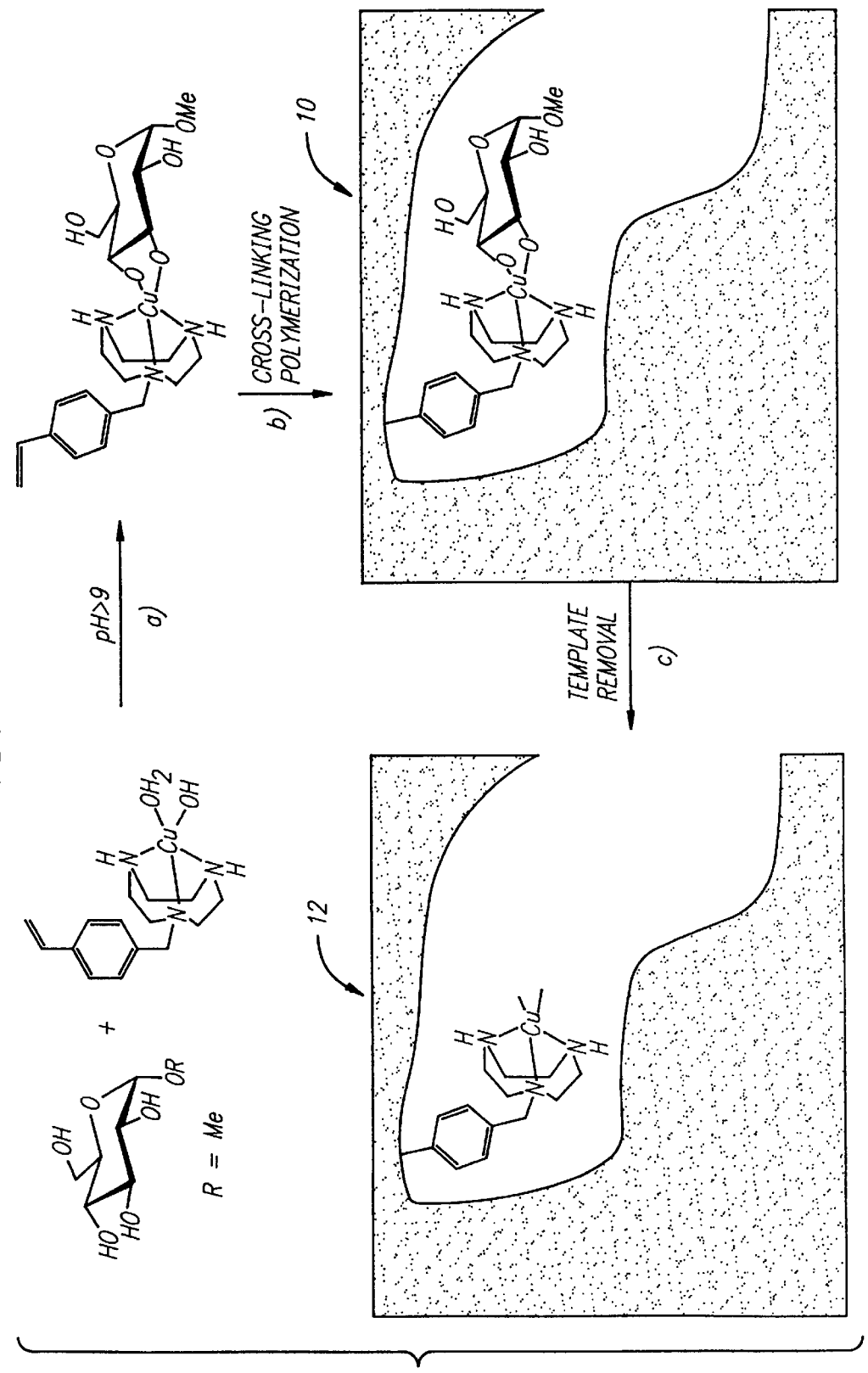

In a further preferred embodiment, the selectivity of the resulting metal complexing sensor polymer is enhanced by utilizing a polymerizable metal complex which is initially bound to the target molecule (or an analog of the target molecule) to form an imprinted polymer matrix. The target molecule (or its analog) serves as a template to assist in the formation of selective binding cavities in the polymer. Imprinting of polymers using metal complexes is a well-known technique which is described in detail in U.S. Pat. No. 5,310,648. The imprinting process is shown schematically in FIGS. 3*a* and *b*. Referring to FIG. 3*a*, initially, the polymerizable copper metal complex is allowed to bind a sugar (methyl-β-D-glucopyranoside) to form an imprinting polymerizable monomer/template complex which is composed of the metal complex and the glucose analog. This imprinting monomer/template complex is then co-polymerized with a suitable crosslinking agent to form a porous polymer structure which is schematically shown at 10 in FIG. 3*a*. The polymer 10 includes the sugar analog and metal complex which is fixed in a cavity formed by the surrounding polymer support structure. The polymer support structure is shown as the shaded region in FIG. 3*a*. In the final step of sensor formation, the template molecule, i.e. the glucose analog, is removed. Removal of the template molecule leaves a macroporous polymer with complementary molecular cavities which include metal complexes that have metal ions which are positioned for specific binding with the template sugar.

Figure 3B:
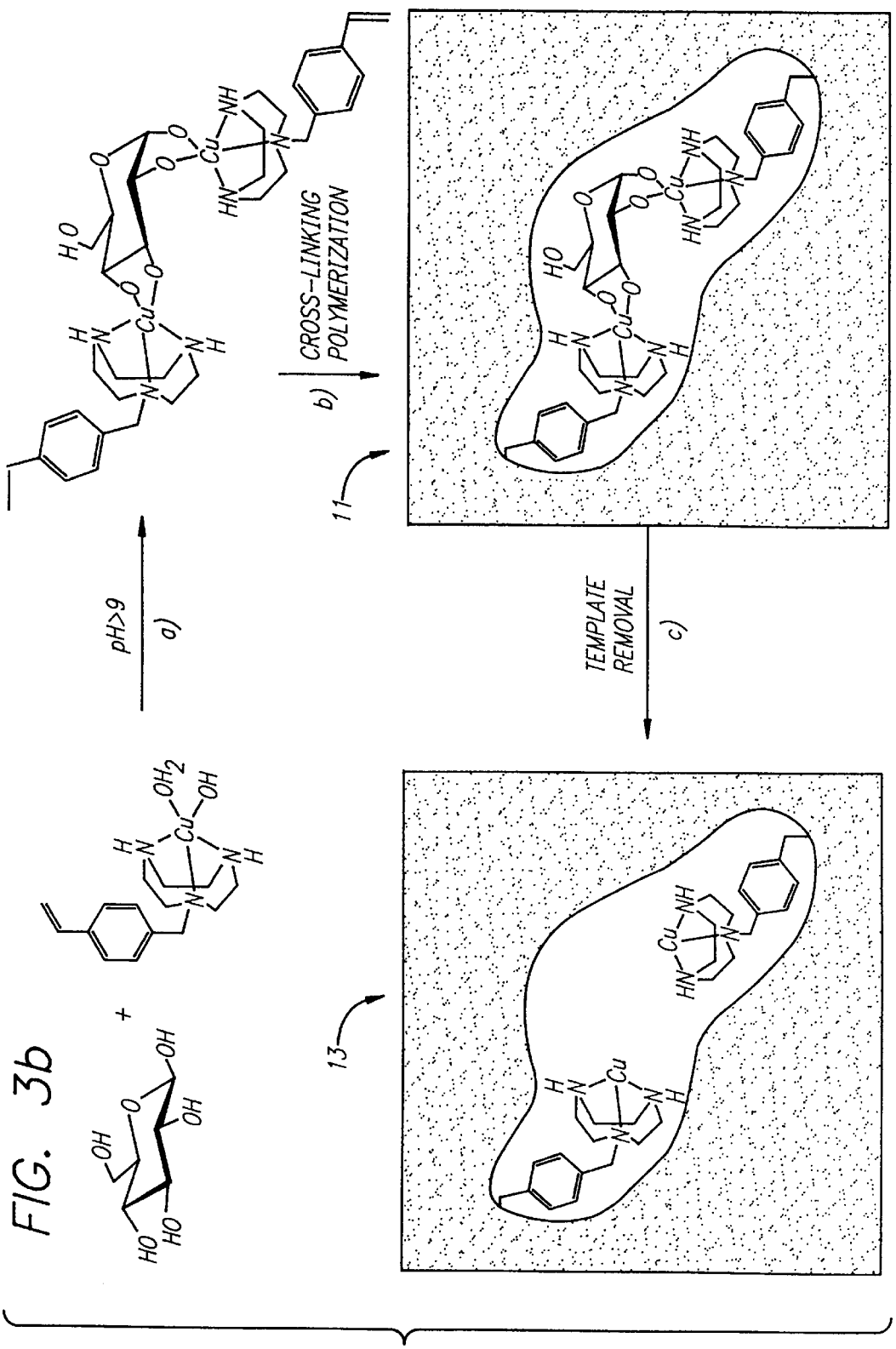

Referring to FIG. 3*b*, the polymerizable copper metal complex is allowed to bind a sugar (glucose) to form an imprinting polymerizable monomer/template complex which is composed this time of two metal complexes attached to the glucose. This imprinting complex is then co-polymerized with a suitable crosslinking agent to form the polymer structure which is schematically shown at 11 in FIG. 3*b*. The polymer 11 includes the sugar and the polymerizable metal complexes which are fixed in a three-dimensional spatial distribution within the surrounding polymer support structure. The polymer support structure is shown as the shaded region in FIG. 3*b*. As before, the glucose template is removed in the final step of sensor polymer formation. Removal of the template molecule leaves a macroporous polymer (13) with complementary molecular cavities which include metal complexes which are positioned for binding with the template sugar or its analogs.

The imprinted polymers (12 and 13) can be prepared in a wide variety of forms ranging from powders to beads to macro structures such as plates, rods, membranes or coatings on other materials. As before, pH-sensitive indicators such as fluorescent probes, optical probes or other pH-sensitive probes can be incorporated into these polymers for detection of glucose binding by optical or other methods. The same polymerizable metal complexes and cross-linking monomers described previously may be used.

As examples of other imprinting polymerizations, the same polymerization conditions described above can be used, except a sugar template molecule such as methyl-α-D-glucopyranoside, α-D-glucose, a disaccharide or oligosaccharide, is first equilibrated with the polymerizable metal complex in aqueous solution at pH >9 to form the polymerizable template complex. Alternatively, other non-sugar template molecules, such as a diol or dopamine, can be used.

The morphology and selectivity of the polymer for binding the target molecule may be improved by altering the solvent, polymerization temperature, choice of crosslinking agent, as described by Sellergren, B., Shea, K. J., "Influence of polymer morphology on the ability of imprinted network polymers to resolve enantiomers," *J. Chromatogr.* A 1993, 635:31–49). In particular, photoinitiation at low temperature should promote high selectivity and strong binding by materials that rely on temperature sensitive interactions for recognition.

Figure 4:
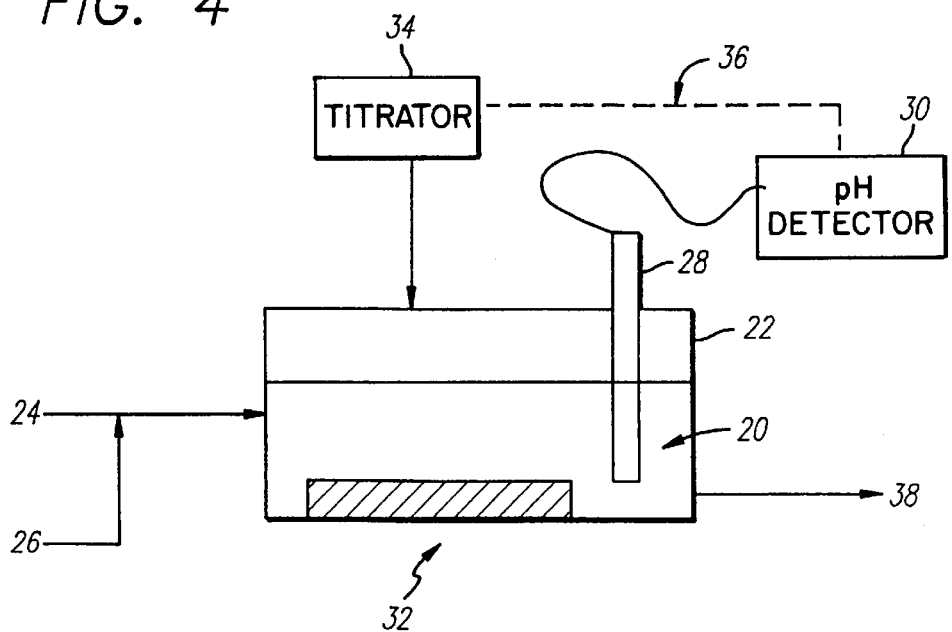

An exemplary sensor system for measuring the presence of sugar in an alkaline aqueous solution is shown in FIG. 4. The solution which is being measured for sugar content is shown at 20. The solution is introduced into the sample chamber 22 via sample introduction line 24. The sample may be blood, urine or other biological fluid. In non-medical applications, the sample solution introduced through inlet 24 can be any aqueous solution such as a fermentation broth or process stream. As mentioned previously, an important aspect of the present invention is that either the test solution 20 be alkaline or that the sensor material 32 be able to provide a local alkaline environment. If necessary, an inlet 26 is provided for allowing input of either acid or basic solutions into the sample solution 24 in order to pre-adjust it to desired pH levels. PH levels of 8 to 13 are preferred. The pH in the test solution 20 is monitored by way of pH measuring probe 28 which is connected to pH meter 30. The probe (field effect transistor, electrode) and metering equipment utilized to measure and monitor pH are well known. The sugar sensor material shown in 32 can be in the form of a plate, block, beads or other macro structure. A preferred type is a macroporous polymer which has been formed by the polymer imprinting process shown in FIGS. 3a or b. The pH of the test solution 20 is continuously monitored while it is present in the test cell 22. This system can be miniaturized to allow sensing with samples as small as one microliter or even less, depending on the sensitivity of the probe.

One way to measure the glucose concentration is to monitor the drop in pH which occurs as the test solution 20 is allowed to interact with sensor material 32. The drop in pH provides an accurate measurement of sugar concentration in the solution when compared to a calibration curve, provided the levels are below saturation in the pH response. In a preferred system, a titrator shown schematically at 34 is provided which adds or generates known amounts of base to the sample chamber 22 in order to maintain the reaction solution 20 a constant pH. This type of static-titration is well known wherein the amount of known base which must be added in order to maintain a constant pH is directly related to the sugar concentration. Feedback loop 36 is provided between the pH detector 30 and titrator 34 to provide automated operation of the system by providing constant pH level input into the titrator to allow control of the amount of base being added.

A similar device can be used for continuous monitoring of sugar levels in a continuous sample stream 24. In this case, an effluent stream 38 removes sample continuously at a rate equal to streams 24 plus 26, such that a constant sample level is maintained in sample chamber 22. As before, the pH, or amount of base required to maintain constant pH, can be monitored continuously in order to obtain a measure of the glucose concentration in the inflowing stream 24.

Figure 5:
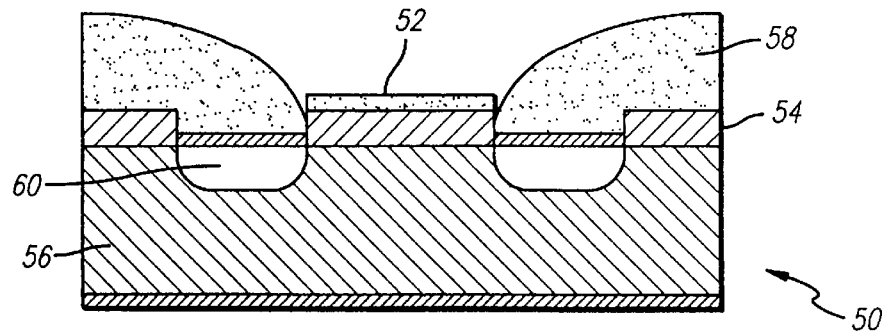

Another exemplary sensor device utilizing a field effect transistor (FET) is shown generally at 50 in FIG. 5. Chemical sensors based on pH detection by FETs are well known (Saito, A. et al., "An ISFET glucose sensor with a silicone rubber membrane for undiluted serum monitoring," *Sensors and Actuators*, B 20, 125–129 (1994); Reinhoudt, D. and E. J. R. Sudholter, "The transduction of Host-Guest interactions into electronic signals by molecular systems," *Advanced Materials*, 2,23–32 (1990)). As shown in FIG. 5, the imprinted polymer membrane 52 is attached to the gate oxide surface 54 of the semiconductor chip 56. The semiconductor chip 56 is preferably p-type silicon. The FET 50 also includes an encapsulant 58 and n-type source/drain 60 as is well-known in the art. An appropriate reference device can be made without the imprinted polymer membrane.

Alternatively, the protons released upon glucose binding to the sensor material could be measured using a light addressable potentiometric sensor (LAPS), as described by McConnell, H. M. et al., "The cytosensor microphysiometer: biological applications of silicon technology," *Science*, 257, 1906–1912 (1992). The sensor material would be applied such that it would be in diffusive contact with the pH-sensitive surface of the LAPS chip.

The simplified schematic systems set forth in FIG. 4 and FIG. 5 will be understood by those of ordinary skill in the art as being merely representative of the type of detection system for which the metal complex sensors are well suited. A wide range of devices may be prepared, and the type of device will depend on the conditions of use (e.g. spot monitoring, continuous monitoring, implantable sensor, process monitoring, whether used in a hospital or at home, disposable, etc.) Another type of device appropriate for spot monitoring of glucose concentrations in clinical or process samples would be a simple calorimetric stick device or paper, in which the protons released by glucose binding would result in a color change of a pH-sensitive dye incorporated into the sensor material. When contacted with the biological sample, an estimate of the glucose concentration can be obtained from the resulting color of the indicator.

Additional exemplary systems include micro detection devices which can be implanted into a patient to provide continual in vivo glucose monitoring. An example of such a system is shown in FIG. 6 in which a biocompatible sugar sensor 70 is implanted under the skin 72. The sugar sensor material 74 is made or treated such that the local environment of the metal complexes embedded in the material is alkaline. Variations in the local glucose concentration in the tissue will result in the release or uptake of protons in the immediate vicinity of the sugar sensor device. The material can be made so that it provides an electrical or optical signal (e.g. by incorporating pH-sensitive fluorophores 76 inside the sensor material) that varies with pH. The sensing material (i.e. metal complex) is preferably embedded in a biocompatible membrane 78. An optical signal can be detected through the skin by interrogation with red light (which readily penetrates skin) and using an appropriate detector to measure either the steady state fluorescence or fluorescence lifetimes, as has been described previously (Bambot, S. B. et al. "Potential applications of lifetime-based phase-modulation fluorimetry in bioprocess and clinical monitoring," *TIBTECH* 13, 106–115 (1995)). The light source is shown in FIG. 6 as laser 80 and the detector is shown at 82. With the use of long-lived fluorophores covalently embedded in the sensor material, subdermal sensing can be carried out with simple and inexpensive instrumentation.

Alternatively, a device can be used ex vivo, connected to a continuous method for drawing a glucose sample from the patient, for example by microdialysis of subcutaneous tissue fluid (Meyerhoff, C. et al. "Use of the microdialysis technique in the monitoring of subcutaneous tissue glucose concentration," *Int'l J. of Art. Organs* 16, 268–275 (1993)), by using a needle to continuously draw subcutaneous tissue fluid, or by transdermal extraction (Tamada et al., Measurement of glucose in diabetic subjects using noninvasive transdermal extraction, *Nature Medicine* 1, 11, 1198–1201 (1995)).

These continuous monitors may be connected to insulin delivery devices by appropriate feed back systems to provide automatic insulin delivery to maintain desired blood glucose levels.

Examples of practice are as follows:

EXAMPLE 1

Use Of Soluble Metal Complexes In Measuring The Concentration Of Sugars And Other Molecules In Aqueous Solution This example shows the use of several metal complexes in accordance with the present invention in measuring the concentration of sugars and other related molecules in aqueous solution. This example demonstrates that a cis-diol (1,4-anhydroerythritol) and a sugar molecule (methyl-β-D-glucopyranoside, Me-β-D-Glc) will bind several complexes of the general formula Cu(II)L (where L=propylenediamine (PDN), iminodiacetate (IDA), diethylenetriamine (DIEN), or triazacyclononane (TACN)) in alkaline aqueous solution. Binding of the target molecule to the metal complex to form a ternary complex results in the release of protons, which can be used to measure the concentration of the bound molecule either through the change in solution pH or by titration and comparison to a calibration curve. The corresponding trans-diol does not bind strongly and therefore does not result in a change in solution pH, demonstrating the selectivity of these complexes. This example also demonstrates how a metal complex is evaluated for its suitability to recognize a particular target molecule in the current invention.

Figure 8:
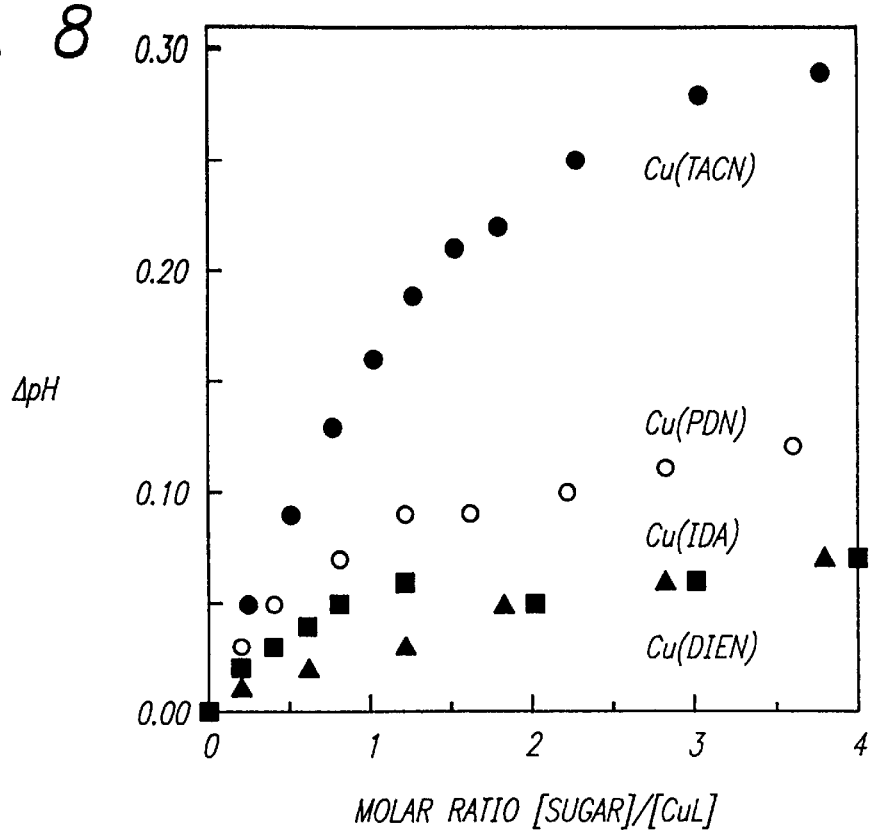

Measurement by pH Depression. 0.10 M solutions of target molecule (cis-diol or Me-β-D-Glc) were prepared at pH=11.0 or 12.0. 10.0 mM solutions of Cu(II)L (where L is either PDN, DIEN, IDA, or TACN) at pH=11.0 or 12.0 were also prepared. The target molecule solution was titrated slowly into 5.0 mL of the CuL solution, and the pH was monitored until saturation was nearly reached (as indicated by a very small changes in pH). FIG. 7 shows the pH curves for titration of the various metal complexes CuL by the cis-diol. The change in pH is most dramatic for Cu(TACN), and the relative order in pH change is in agreement with the order of binding affinities obtained by isothermal titration calorimetry. In contrast, the corresponding trans-diol does not result in a pH change, because its diol geometry differs from that of the cis compound, such that it is not capable of chelating the Cu(II) complex. Thus Cu(TACN) is specific for the cis-diol. FIG. 8 shows the pH titration of the various metal complexes CuL using Me-β-D-Glc. Again, the pH change is most dramatic for the Cu(TACN), indicating that Cu(TACN) is the best of the four Cu(II) complexes for chelating sugars or the related cis-diol compounds.

The concentration of an unknown sample of cis-diol or Me-β-D-Glc can be determined by adding a known quantity to one of the metal complex solutions, measuring the resulting depression in pH and comparing that value to these calibration curves prepared using known quantities.

Measurement by Solution pH Titration. A solution of Cu(TACN) with concentration around 10.0 mM was prepared without adjusting the pH. Since TACN is very hygroscopic and weighing errors are unavoidable, the concentration of the solution was calibrated to be 8.9 mM by its UV/vis absorption at 656 nm ($\lambda_{max}$=656 nm, $\epsilon$=47 M$^{-1}$ cm$^{-1}$). Target molecule solutions (cis-diol and Me-β-D-Glc) of concentration 0.10 M and pH of 9.0, 10.0, 11.0, or 12.0 were prepared. 5.00 mL of the Cu(TACN) solution was introduced into the titration vessel of a Brinkman pH titrator. The vessel was sealed, purged thoroughly with $N_2$, and equilibrated to 25° C. by a constant temperature water bath. The pH of the Cu(TACN) solution was adjusted to a desired value (9.0, 10.0, 11.0, or 12.0) with the addition of 0.10 N sodium hydroxide solution. Then a target molecule solution of the same pH as the Cu(TACN) solution in the titration vessel was titrated into the Cu(TACN) solution. After each injection of target molecule solution (cis-diol or Me-β-D-Glc), the pH of the solution decreased, and the automatic pH titrator automatically added 0.10 N sodium hydroxide to bring the solution pH back to the original value. The volumes of the solution injected and the volumes of the 0.10 N sodium hydroxide added to maintain constant pH were recorded.

Figure 9:
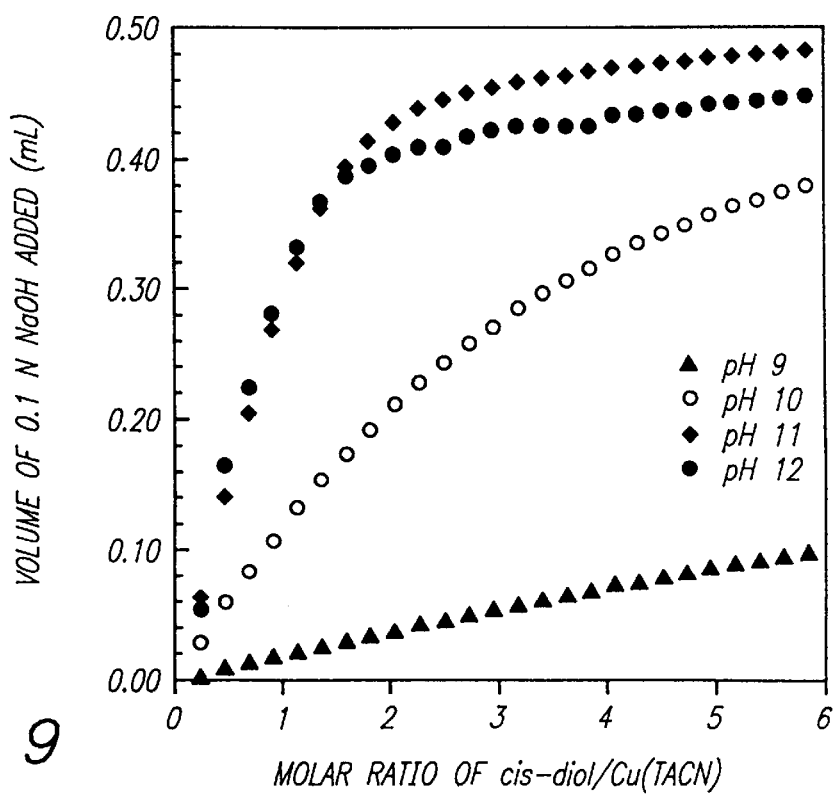
Figure 10:
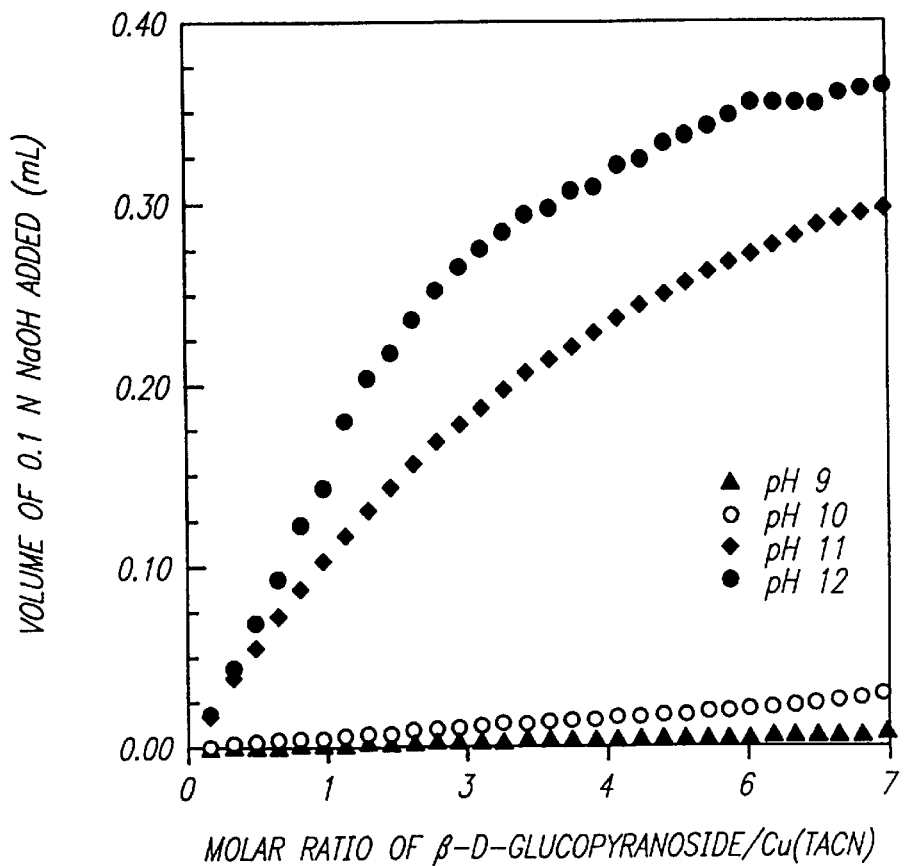

The amount of sodium hydroxide added during the titration is theoretically equal to the amount of protons released during the sugar binding reaction. FIG. 9 shows the titration data for the Cu(TACN)/cis-diol system at various values of pH. The apparent binding strength greatly depends on the pH of the solution. At pH 9, the binding is very weak and saturation conditions are approached only at higher target molecule concentrations. However, at pH 11 or 12, saturation occurs at lower concentrations of target molecule, corresponding to a molar ratio of target molecule to Cu(TACN) of approximately 2. Thus there is a trade-off between the range of easily measurable concentrations and sensitivity of the sensor. At lower pH, the concentration range is greatest, but the sensitivity in terms of protons released is lowest. FIG. 10 shows the pH static titration data for Cu(TACN)/Me-β-D-Glc system at various values of pH. Again, the apparent binding strength increases at higher pH.

The concentration of an unknown sample of cis-diol or Me-β-D-Glc can be determined by adding a known quantity to one of the metal complex solutions, measuring the resulting depression in pH and comparing that value to these calibration curves prepared with known quantities.

EXAMPLE 2

Synthesis Of A Novel Soluble Metal Complexing Agent, 1,4-dimethyl-1,4,7-triazacyclononane, For Sugar Sensing 1,4,7-Triazacyclononane-N, N', N"-tritosylate (100 g) was suspended in a mixture of 200 mL of glacial acetic acid (100%) and 300 mL of HBr (48%) and the reaction mixture was refluxed under vigorous stirring for 15–18 hours. After cooling, the reaction mixture was filtered. To the filtrate were added 1 L of ethanol and 1 L of diethylether. 1,4,7-

Triazacyclononane-N-monotosylated-dihydrobromide (ca 45.4 g) was crystallized and the crystals were washed with acetone and diethylether and dried in the air. For further purification, the product can be stirred in refluxing acetone for 30 minutes.

1,4,7-Triazacyclononane-N-monotosylated-dihydrobromide (42.0 g) was dissolved in minimum amount of $H_2O$ (ca. 50 mL) and to this solution was added NaOH carefully to pH 7. 75 mL of an aqueous solution of formaldehyde (37% $CH_2O$) and 75 mL of concentrated formic acid (HCOOH) were added to the solution and the resultant mixture was brought to reflux for 15 hours. The reaction was cooled to room temperature and 30 mL of concentration. HCl added and the excess solvent was removed on a rotovapor to yield a solid. This solid was suspended in minimum of water, neutralized with NaOH and the resultant solution was stood for 12 hours at room temperature. 1,4-Dimethyl-1,4,7-triazacyclononane-7-tosylate was crystallized slowly as a white solid, which was collected by filtration (ca. 17 g) and was dried over CaO in a desiccator. This intermediate was then suspended in 300 mL of HBr (48%) and brought to reflux with stirring for 48 hours. The solution was concentrated to dryness under vacuum. The residue was then washed with dry acetone and about 54 g of 1,4-dimethyl-1,4,7-triazacyclononanetribromide was isolated. This salt was dissolved in 200 mL of water and to this solution was added 20 g of NaOH and 500 mL of toluene. The mixture was then refluxed with dean stark apparatus to remove all the water. The resultant solution was then filtered and the filtrate was concentrated on a rotovap to yield a yellow oil which can be stored under Ar at 0° C. indefinitely.

The complex is made polymerizable and loaded with copper(II) by the procedures outlined in Example 3.

EXAMPLE 3

Synthesis Of Polymerizable Metal Complexes For Use In The Preparation Of Selective Sensors This example shows the synthesis of polymerizable metal complexes containing triazacyclononane in accordance with the present invention. Three polymerizable metal-chelating ligands, Msty-TACN (1-(4'-vinylbenzyl)-1,4,7-triazacyclononane), Dsty-TACN (1,4-bis(4'-vinylbenzyl)-1,4,7-triazacyclononane), andTsty-TACN(1,4,7-tris(4'-vinylbenzyl)-1,4,7-triazacyclononane), were prepared and loaded with copper ions according to the following procedures. The resulting polymerizable metal complexes were used to prepare imprinted polymeric sensors, as described in further examples.

1-(4'-vinylbenzyl)-1,4,7-triazacyclononane (Msty-TACN)

Triazacyclononane (2 g, 15.5 mmol), powdered NaOH (0.62 g, 15.5 mmol) and dry acetonitrile (35 mL) were placed in a 100 mL 2-neck round-bottomed flask charged with a reflux condenser. The reaction mixture was brought to reflux under argon for an hour. To this suspension was added dropwise a solution of chloromethyl styrene (1.84 g, 12.4 mmol) in 10 mL of acetonitrile over a period of 8 hours, during which the consumption of the starting material was closely monitored by thin layer chromatography on a neutral alumina oxide gel plate with 20% $MeOH/CHCl_3$ as eluent. White solid was then removed by filtration and washed with acetonitrile (20 mL×2). The filtrate was concentrated on a rotovap to yield a yellowish oil which was taken up in $CHCl_3$ (100 mL) and washed with water (30 mL×2) and brine (30 mL×2). The organic layer was dried over $Na_2SO_4$, filtered and concentrated in vacuo to obtain a blondish oil, which was chromatographed on neutral alumina oxide gel with 10% $MeOH/CHCl_3$ as eluent ($R_f$ of the product, 0.25). The product obtained was a yellowish solid, which weighed 1.68 g (44%): mp 56–59° C.; $^1HNMR$ ($CDCl_3$) δ 2.72 (t, 4H, J=4.8 Hz), 2.876 (t, 4 H, J=4.8 Hz), 3.085 (s, 4H), 3.769 (s, 2H), 5.239 (d, 1H, J=10.8 Hz), 5.741 (d, 1H, J=17.4 Hz), 6.202 (s, 2H), 6.692 (dd, 1H, J=10.8 Hz, 17.4 Hz), 7.259 (d, 2H, J=7.8 Hz), 7.376 (d, 2H, J=7.8 Hz); $^{13}C\{^1H\}$ NMR ($CDCl_3$, 75 MHz) 6 44.07, 45.07, 50.68, 60.76, 113.83, 126.30, 129.18, 136.30, 136.77, 137.75; HRMS (FAB$^+$) cacid for $C_{15}H_{23}N_3$ 245.1892, found 246.1970(MH$^+$); IR (KBr): υ 3453,3050,2907,1633,1517,1455, 1291,1105, 904.

1,4-bis(4'-vinylbenzyl)-1,4,7-triazacyclononane (Dsty-TACN)

Dsty-TACN was obtained as another product from the same reaction and chromatography ($R_f$ of the product, 0.54) as described above. Yellowish solid product was obtained, which weighed 1.51 g (27%): mp 162–164° C.; $^1H$ NMR ($CDCl_3$) δ 2.5 21 (s, 4H), 2.913 (t, 4H, J=5.7 Hz), 3.01 0 (s, 1 H), 3.104 (t, 4H, J=5.7 Hz), 3.734(s, 4H), 5.319 (d, 2H, J=10.8 Hz), 5.817 (d, 2H, J=17.4 Hz), 6.764 (dd, 2H, J=10.8 Hz, 17.4 Hz), 7.267 (d, 4H, J=8 Hz), 7.432 (d, 4H, J=8 Hz); $^{13}C\{^1H\}$ NMR ($CDCl_3$, 75 MHz) δ 43.92, 47.50, 50.33, 60.66, 114.21, 126.47, 129.35, 136.15, 136.66, 137.17 HRMS (FAB$^+$) cacid for $C_{24}H_{31}N$ 362.2596, found 362.2591; IR (KBr) υ 3472, 3450, 2920, 2741, 1627, 1560,1394,1207, 923, 860,736 cm$^{-1}$.

1,4,7-tris(4'-vinylbenzyl)-1,4,7-triazacyclononane (Tsty-TACN),

Tsty-TACN was obtained as the third product from the same reaction and chromatography ($R_f$ of the product, 0.73) as described above. Yellowish solid product was obtained, which weighed 1.33 g (18%): mp 71–73° C.; $^1H$ NMR ($CDCl_3$) δ 2.963 (s, 12H), 3.739 (s, 6H), 5.353 (d, 3H, J=10.8 Hz), 5.861 (d 3H, J=17.4 Hz), 6.828 (dd, 4H, J=10.8 Hz, 17.4 Hz), 7.381 (d, 6H, J=7.8 Hz), 7.475 (d, 6H, J=7.8 Hz); $^{13}C\{^1H\}$ NMR ($CDCl_3$, 75 MHz) δ 55.36, 62.73, 113.17, 125.94, 129.19, 136.04, 136.66, 140.09; HRMS (FAB$^+$) cacid for $C_{33}H_{39}N_3$ 477.3144, found 477.3139; IR (KBr) υ 3049, 2904, 1627, 1508, 1451, 1295,909.7,828 cm$^{-1}$.

[Cu(Msty-TACN)]$^{2+}$ $SO_4^{2-}$

To a solution of Msty-TACN (1.71g, 6.98 mmol) in methanol (100 mL) was added $CuSO_4·5H_2O$ (1.7 g, 0.98 mmol) portionwise at room temperature. The solution turned turbid when about half amount of $CuSO_4·5H_2O$ was added. After vigorous stirring for a few minutes, the solution turned clear sky blue. The solution was kept stirring for an additional hour after the remaining $CuSO_4·5H_2O$ was added. Solvent was then removed on a rotavap to yield a blue solid, which was recrystallized from methanol/acetonitrile to give 1.35 g (48%) of a blue crystalline solid: mp 177–181 ° C.; Anal. Calcd for $C_{15}H_{23}N_3O_4SCu$: C, 44.55; H, 5.74; N, 10.40; Cu, 15.57. Found: C, 44.90; H, 5.86; N, 10.13; Cu, 15.80; IR (KBr): υ 3260,2924,1627, 1458, 1097 cm$^{-1}$; UV-vis (in $CH_3OH$) ε: 75 at 657 nm.

[Cu(Dsty-TACN)]$^{2+}$ $SO_4^{2-}$

To a solution of Dsty-TACN (0.56 g, 1.55 mmol) in methanol (50 mL) was added $CuSO_4·5H_2O$ (0.387 g, 1.55 mmol) as a solid portion wise at room temperature. The solution turned green first and then cloudy. Blue precipitate started forming after a few more minutes' vigorous stirring. The resulting mixture was kept stirring for an additional hour. The precipitate was collected by filtration, and was further purified by recrystallization with methanol/water to give 0.45 g (53%/) of a blue crystalline solid: mp 276–280 (decomp.); Anal. Calcd for $C_{25}H_{35}N_3O_5SCu$ (M+$CH_3OH$): C, 54.33; H, 6.39; N, 7.61; Cu, 11.40. Found: C, 53.99; H, 5.99; N, 7.78; Cu, 11.78; IR (KBr): υ 3500–3100, 2977, 1629, 1055, 830, 746 cm$^{-1}$.

[Cu(Tsty-TACN)]$^{2+}$ SO$_4^{2-}$

To a solution of Dsty-TACN (1.33 g, 2.79 mmol) in CH$_3$OH/CH$_3$Cl (50 mL/30 mL) was slowly added a solution of CUSO$_4$·5H$_2$O (0.692 g, 2.79 mmol) in 20 mL of methanol at room temperature. The solution turned blue and cloudy. The resulting mixture was kept stirring for an additional hour. The precipitate was collected by filtration, and was further purified by recrystallization with DMF/H$_2$O to give 1.34 g (75%) of a blue crystalline solid: mp 280–284 (decomp.); Anal. Calcd for C$_{33}$H$_{39}$N$_3$O$_4$SCu: C, 62.24; H, 6.18; N, 6.60; Cu, 9.89. Found: C, 60.16; H, 6.20; N, 6.33; Cu, 9.89; IR (KBr): υ 3000 (br), 1508, 1458, 12228, 1143 858, 830 cm$^{-1}$.

EXAMPLE 4

Preparation Of A Sensor Polymer For Methyl-α-D-glucopyranoside

This example shows the preparation of a sensor in accordance with the present invention which includes a polymer support structure imprinted with a glucopyranoside. The example also demonstrates the ability of the sensor to rebind with the template molecule and produce protons upon rebinding. This example uses Cu(II)-[1,4-bis(4'-vinylbenzyl)-1,4,7-triazacyclononane] (Dsty-TACN-Cu$^{2+}$) as the polymerizable metal complex.

Imprinted Polymer Preparation:

30 mg (0.058 mmol) of [Dsty-TACN-Cu$^{2+}$]SO$_4^{2-}$, 33.58 mg (0.165 mmol) of Me-α-D-Glc were dissolved in a mixed solvent composed of 1.11 mL water and 2.22 mL methanol. The pH of the solution was adjusted to 11.50 with addition of 1 N sodium hydroxide. After equilibrating at room temperature for half an hour, 1.0 g (6.49 mmol) of N,N'-methylene bisacrylamide and 10 mg of 2,2'-azobisisobutyronitrile (AIBN) were added into the solution. After purging the solution with argon, the flask was sealed and heated at 60° C. The solution was polymerized at 60° C. for 7 hours. After polymerization was complete, the polymer was ground into a fine powder using a mortar and washed three times with 50/50 water/methanol. The resin was equilibrated with 100 mM EDTA solution at 60° C. for several hours to strip off most of the Cu(II) ion and the template sugar molecule. The polymer resin was then washed with water to remove extra EDTA, reloaded Cu(II) with 20 mM CuSO$_4$ solution, washed again with water to remove free Cu(III), and finally frozen and lyophilized.

Rebinding of methyl-α-D-glucopyranoside to the imprinted polymer:

1 of the imprinted polymer resin and 20 mL of water were placed into the pH titration vessel. The vessel was equilibrated to 60° C. The pH of the suspension was adjusted to 11.00 by addition of 0.1 N sodium hydroxide. A solution of methyl-α-D-glucopyranoside with a concentration of 0.10 M and pH of 11.00 was prepared. The sugar solution was titrated into the polymer suspension sequentially. After each addition, 0.10 N sodium hydroxide solution was added to maintain pH of the system at 11.00. The system was kept stirring for a few minutes until equilibrium was reached. The volumes of the sugar solution injected and of the 0.10 N sodium hydroxide solution added were recorded for data analysis. The data from this static titration are set forth in Table 1.

TABLE 1

Titration of sensor with methyl-α-D-glucopyranoside (pH 11.00)

| titration No.# | V$_{glucose}$(mL) | V$_{NaOH}$(mL) |
| --- | --- | --- |
| 0 | 0.00 | 0.000 |
| 1 | 0.50 | 0.027 |
| 2 | 1.00 | 0.073 |
| 3 | 1.50 | 0.100 |
| 4 | 2.00 | 0.137 |
| 5 | 2.50 | 0.144 |
| 6 | 3.00 | 0.144 |
| 7 | 3.50 | 0.144 |
| 8 | 4.00 | 0.144 |

As can be seen from Table 1, the amount of sugar added to the solution is directly related to the amount of NaOH which must be added in order to maintain a constant pH. Accordingly, the sensor provided an indirect measure of the amount of sugar added to the solution.

EXAMPLE 5

Preparation Of A Sensor For Methyl-α-D-glucopyranoside Which Includes A Non-imprinted Ligand Support Polymer This example shows the preparation of a sensor which includes a polymer that is not imprinted with a template molecule. This example also demonstrates the sensor material's ability to bind methyl-α-D-glucopyranoside and produce protons.

Polymer Preparation:

30 mg (0.058 mmol) of [Dsty-TACN-Cu$^{2+}$]SO$_4^{2-}$ was dissolved in a mixed solvent composed of 1.11 mL water and 2.22 mL methanol. The pH of the solution was adjusted to 11.50 with addition of 1 N sodium hydroxide. After equilibrating at room temperature for half an hour, 1.0 g (6.49 mmol) of N,N'-methylene bisacrylamide and 10 mg of 2,2'-azobisisobutyronitrile (AIBN) were added into the solution. After purging the solution with argon, the flask was sealed and heated at 60° C. The solution was polymerized at 60° C. for 7 hours. After polymerization was complete, the polymer was ground into a fine powder using a mortar and washed three times with 50/50 water/methanol. The resin was equilibrated with 100 mM EDTA solution at 60° C. for several hours to strip off most Cu(II) ion. The polymer resin was then washed with water to remove extra EDTA, reloaded Cu(II) with 20 mM CuSO$_4$ solution, washed again with water to remove free Cu(II), and finally frozen and lyophilized.

Binding of methyl-α-D-glucopyranoside to the polymer:

1 g of the polymer resin and 20 mL of water were placed into the pH titration vessel. The vessel was equilibrated to 60° C. The pH of the suspension was adjusted to 11.00 by addition of 0.1 N sodium hydroxide. A solution of methyl-α-D-glucopyranoside with a concentration of 0.10 M and pH of 11.00 was prepared. The sugar solution was titrated into the polymer suspension sequentially. After each addition, 0.10 N sodium hydroxide solution was added to maintain pH of the system at 11.00. The system was kept stirring for a few minutes until equilibrium was reached. The volumes of the sugar solution injected and of the 0.10 N sodium hydroxide solution added were recorded for data analysis. The data from this static titration are set forth in Table 2.

TABLE 2

Titration of sensor with methyl-α-D-glucopyranoside at pH 11.00 and 60° C.

| titration No.# | $V_{glucose}$ (mL) | $V_{NaOH}$ (mL) |
|---|---|---|
| 0 | 0.00 | 0.000 |
| 1 | 0.50 | 0.031 |
| 2 | 1.00 | 0.068 |
| 3 | 1.50 | 0.093 |
| 4 | 2.00 | 0.134 |
| 5 | 3.00 | 0.202 |
| 6 | 4.00 | 0.303 |
| 7 | 5.00 | 0.321 |
| 8 | 6.00 | 0.321 |

As can be seen from Table 2, the amount of sugar added to the solution is directly related to the amount of NaOH which must be added in order to maintain a constant pH. Accordingly, as in Example 4, the sensor provided an indirect measure of the amount of sugar added to the solution.

EXAMPLE 6

Preparation Of An Imprinted Sensor Polymer Which Includes Methyl-β-D-glucopyranoside As The Template Molecule And Cu(II)-[N-(4-vinyl) imino)diacetic acid] (Sty-IDA-$Cu^{2+}$ As The Polymerizable Metal Complex This example demonstrates the ability of the imprinted metal-complexing polymer to bind glucose and produce protons. This example also shows that the system can be configured such that the proton release is linearly proportional to the glucose concentration. Finally, this example demonstrates the use of styrene-IDA-$Cu^{2+}$ as the polymerizable metal complex.

Imprinted Polymer Preparation:

0.75 g (2.29 mmol) of styrene-IDA-$Cu^{2+}$ (prepared according to the procedures outlined in U.S. Pat. No. 5,310, 648) and 0.465 g (2.29 mmol) of Me-β-D-Glc were dissolved in a mixed solvent composed of 16.67 mL water and 33.33 mL methanol. The pH of the solution was adjusted to 11.50 with addition of 1 N sodium hydroxide. After equilibrating at room temperature for half an hour, 14.25 g (92.4 mmol) of N,N'-methylenebisacrylamide and 150 mg of 2,2'-azobisisobutyronitrile (AIBN) were added into the solution. After purging the solution with argon, the flask was sealed and heated at 60° C. The solution was polymerized at 55° C. for 21 hours and at 70° C. for additional 4 hours. After polymerization was complete, the polymer was ground into a fine powder using a mortar and washed three times with 50/50 water/methanol. The resin was equilibrated with 100 mM EDTA solution at 60° C. for several hours to strip off most of the Cu(II) ion and the template sugar molecule. The polymer resin was then washed with water to remove extra EDTA, reloaded Cu(II) with 20 mM $CuSO_4$ solution, washed again with water to remove free Cu(II), and finally frozen and lyophilized.

Rebinding of Glucose to the Polymer:

3.0 g of the imprinted polymer resin and 30 mL of pH 11.50 NaOH solution were placed into the pH titration vessel. The vessel was equilibrated to 60° C. The pH of the suspension was adjusted to 11.52 by addition of 0.1 N sodium hydroxide. A solution of D-(+)-glucose with a concentration of 0.50 M and pH of 11.52 was titrated into the polymer suspension. After each addition, 0.10 N sodium hydroxide solution was added to maintain pH of the system at 11.52. The system was kept stirring for a few minutes until equilibrium was reached. The volumes of the sugar solution injected and of the 0.10 N sodium hydroxide solution added were recorded for data analysis. The data for the static titration are tabulated in Table 3. As can be seen from Table 3, the amount of base required to maintain the pH of the solution is linearly proportional to the concentration of glucose in the solution.

TABLE 3

Titration of sensor with glucose at pH 11.52 and 60° C.

| $V_{glucose}$(mL) | $C_{glucose}$(mM) | $V_{NaOH}$(mL) |
|---|---|---|
| 0.100 | 0.133 | 1.56 |
| 0.200 | 0.188 | 3.12 |
| 0.300 | 0.231 | 4.69 |
| 0.400 | 0.262 | 6.24 |
| 0.500 | 0.301 | 7.81 |
| 0.600 | 0.336 | 9.37 |
| 0.700 | 0.373 | 10.9 |
| 0.800 | 0.412 | 12.4 |
| 0.900 | 0.442 | 14.1 |
| 1.00 | 0.475 | 15.6 |
| 1.10 | 0.508 | 17.2 |
| 1.20 | 0.543 | 18.7 |

EXAMPLE 7

Preparation Of An Imprinted Glucose Sensor Polymer Which Includes Methyl-β-D-glucopyranoside As The Template And Msty-TACN-$Cu^{2+}$ As The Polymerizable Metal Complex This example demonstrates the ability of the metal-complexing polymer to bind glucose and produce protons. This example also shows that the system can be configured such that the proton release is proportional to glucose concentration. This example further demonstrates the use of Cu(II)-[1-(4'-vinylbenzyl)-1,4,7-triazacyclononane] (Msty-TACN-$Cu^{2+}$) as the polymerizable metal complex.

Imprinted Polymer Preparation:

0.4045 g (1.0 mmol) of [Msty-TACN-$Cu^{2+}$]$SO_4^2$ and 0.2032g (1.0 mmol) of Me-β-D-Glc were dissolved in a mixed solvent composed of 4.0 mL water and 8 mL methanol. The pH of the solution was adjusted to 11.70 with addition of 1 N sodium hydroxide. After equilibrating at room temperature for half an hour, 3.13 g (20 mmol) of N,N'-methylene bisacrylamide was added into the solution. After freeze-thawing for 4 cycles to degas the solution, the flask was sealed and heated at 65° C. As all solid became completely dissolved, 35 mg AIBN dissolved in 0.5 mL degassed methanol was syringed into the solution. The solution was polymerized at 65° C. overnight and at 70° C. for 12 hours. After polymerization was complete, the polymer was ground into a fine powder using a mortar and washed three times with 50/50 water/methanol. The resin was loaded into a glass column and was washed with 100 mM EDTA solution continuously overnight to strip off all the Cu(II) ion and the template sugar molecule. The polymer resin was then washed with water to remove extra EDTA, reloaded Cu(II) with 20 mM $CuSO_4$ solution, washed again with water to remove free Cu(II), and finally frozen and lyophilized.

Rebinding of Glucose to the Imprinted Polymer:

0.5 g of polymer resin was suspended in 5.0 mL pH 11.50 NaOH solution in the pH titration vessel, which was kept at 25° C. by a constant temperature water bath. The pH of the suspension was adjusted to 11.50 by addition of 6N sodium hydroxide solution. A solution of D-(+)-glucose with concentration of 0.208 M and pH of 11.50 was prepared. The glucose solution was titrated into the polymer suspension sequentially. After each addition, 0.10 N sodium hydroxide solution was added to maintain pH of the system at 11.50. The system was kept stirring for a few minutes until equilibrium was reached. The volumes of the glucose solution injected and of the 0.10 N sodium hydroxide solution added were recorded for data analysis. The data for the static titration are given in Table 4.

TABLE 4

Titration of sensor polymer with glucose at pH 11.52

| $V_{glucose}$(mL) | $C_{glucose}$(mM) | $V_{NaOH}$(mL) |
|---|---|---|
| 0.020 | 0.743 | 0.028 |
| 0.040 | 1.49 | 0.056 |
| 0.060 | 2.23 | 0.077 |
| 0.080 | 2.97 | 0.096 |
| 0.100 | 3.71 | 0.114 |
| 0.120 | 4.46 | 0.128 |
| 0.140 | 5.20 | 0.141 |
| 0.160 | 5.94 | 0.158 |
| 0.180 | 6.69 | 0.170 |
| 0.200 | 7.43 | 0.180 |
| 0.220 | 8.17 | 0.189 |
| 0.240 | 8.91 | 0.202 |
| 0.260 | 9.66 | 0.210 |
| 0.280 | 10.4 | 0.217 |
| 0.300 | 11.1 | 0.224 |
| 0.305 | 13.0 | 0.239 |
| 0.400 | 14.9 | 0.249 |
| 0.450 | 16.7 | 0.259 |
| 0.500 | 18.6 | 0.269 |
| 0.550 | 20.4 | 0.275 |
| 0.600 | 22.3 | 0.281 |

As can be seen from Table 4, the proton release from the sensor polymer (the volume of NaOH added to maintain constant pH) is proportional to the glucose concentration.

EXAMPLE 8

Preparation Of Polymers Using Methyl-β-D-glucopyranoside As The Template And Msty-TACN-$Cu^{2+}$ As The Polymerizable Metal Complex And Glucose Rebinding To The Polymers This example demonstratesthat polymers containing various concentrations of functional monomer ($Cu^{2+}$ sites) can be prepared. It also shows that glucose rebinding to the materials depends on the solution pH.

Polymers I to IV are rigid polymers prepared using four different ratios of functional monomer Msty-TACN-$Cu^{2+}$ (Cu(II)-[1-(4'-vinylbenzyl)-1,4,7-triaza-cyclononane]) to crosslinker MBA (N,N'-methylenebisacrylamide), as listed in Table 5. The synthesis of each polymer is described below, as is their behavior in glucose rebinding studies. Polymer IV, with the highest $Cu^{2+}$ density, gives the most linear response over the widest range of solution glucose concentration.

Synthesis of Polymers I–IV

Four polymers of varying molar ratio Msty-TACN-$Cu^{2+}$ monomer to crosslinker MBA (ratios shown in Table 5) were prepared as described below. Following polymerization, the material was ground into a fine powder using a mortar and washed with 50/50 water/methanol. The powder was loaded into a glass column and washed extensively with 100 mM EDTA solution to strip off all the Cu(II) ion and the template sugar molecules. The polymer resin was then washed with water to remove residual EDTA, reloaded with 20 mM $CuSO_4$ solution, washed again with water to remove free Cu(II), frozen and lyophilized.

TABLE 5

Molar ratios of Msty-TACN-$Cu^{2+}$ to crosslinker MBA in Polymers I–IV

| | Polymer I | Polymer II | Polymer III | Polymer IV |
|---|---|---|---|---|
| Mole ratio of Msty-TACN-$Cu^{2+}$ to MBA | 1:20.32 | 1:16.14 | 1:13 | 1:10 |

Polymer I. [Msty-TACN-$Cu^{2+}$]$SO_4^{2-}$ (0.4045 g, 1.0 mmol) and Me-β-D-Glc (0.2032 g, 1.0 mmol) were dissolved in a mixture of 4.0 mL pH 11.50 aqueous NaOH solution and 8 mL methanol. The pH of the solution was adjusted to 11.50 with addition of 1 N sodium hydroxide. After equilibrating at room temperature for half an hour, 3.13 g (20.30 mmol) of MBA was added into the solution. After freeze-thawing for 4 cycles to degas the solution, the flask was sealed and heated at 65° C. As all solid became completely dissolved, 35 mg AIBN dissolved in 0.5 mL degassed methanol was syringed into the solution. The solution was polymerized at 65° C. overnight and at 70° C. for 12 hours.

Polymer II. [Msty-TACN-$Cu^{2+}$]$SO_4^{2-}$ (0.1011 g, 0.25 mmol) and Me-β-D-Glc (0.0508 g, 0.25 mmol) were dissolved in a mixture of 2.0 mL of methanol and 1 mL of pH 11.50 aqueous NaOH solution in a vial. The pH of the solution was further adjusted to 11.50 with addition of 1 N sodium hydroxide. After equilibrating at room temperature for half an hour, 0.621 g (4.028 mmol) of MBA and 9 mg of AIBN were added into the solution. After freeze-thawing for 4 cycles to degas the solution, the vial was sealed and heated at 65° C. The solution was polymerized at 65° C. overnight and at 70° C. for 12 hours.

Polymer III. [Msty-TACN-$Cu^{2+}$]$SO_4^{2-}$ (0.1011 g, 0.25 mmol) and Me-β-D-Glc (0.0508 g, 0.25 mmol) were dissolved in a mixture of 1.7 mL of methanol and 0.8 mL of pH 11.50 aqueous NaOH solution in a vial. The pH of the solution was further adjusted to 11.50 with addition of 1 N sodium hydroxide. After equilibrating at room temperature for half an hour, 0.501 g (3.25 mmol) of MBA and 9 mg of AIBN were added into the solution. After freeze-thawing for 4 cycles to degas the solution, the vial was sealed and heated at 65° C. The solution was polymerized at 65° C. overnight and at 70° C. for 36 hours.

Polymer IV. [Msty-TACN-$Cu^{2+}$]$SO_4^{2-}$ (0.1011 g, 0.25 mmol) and Me-β-D-Glc (0.0508g, 0.25 mmol) were dissolved in a mixture of 1.5 mL of methanol and 0.7 mL of pH 11.50 aqueous NaOH solution in a vial. The pH of the solution was further adjusted to 11.50 with addition of 1 N sodium hydroxide. After equilibrating at room temperature for half an hour, 0.385 g (2.50 mmol) of MBA and 9 mg of AIBN were added. After freeze-thawing for 4 cycles to degas the solution, the vial was sealed and heated at 65° C. The solution was polymerized at 65° C. overnight and at 70° C. for 36 hours.

Figure 11:
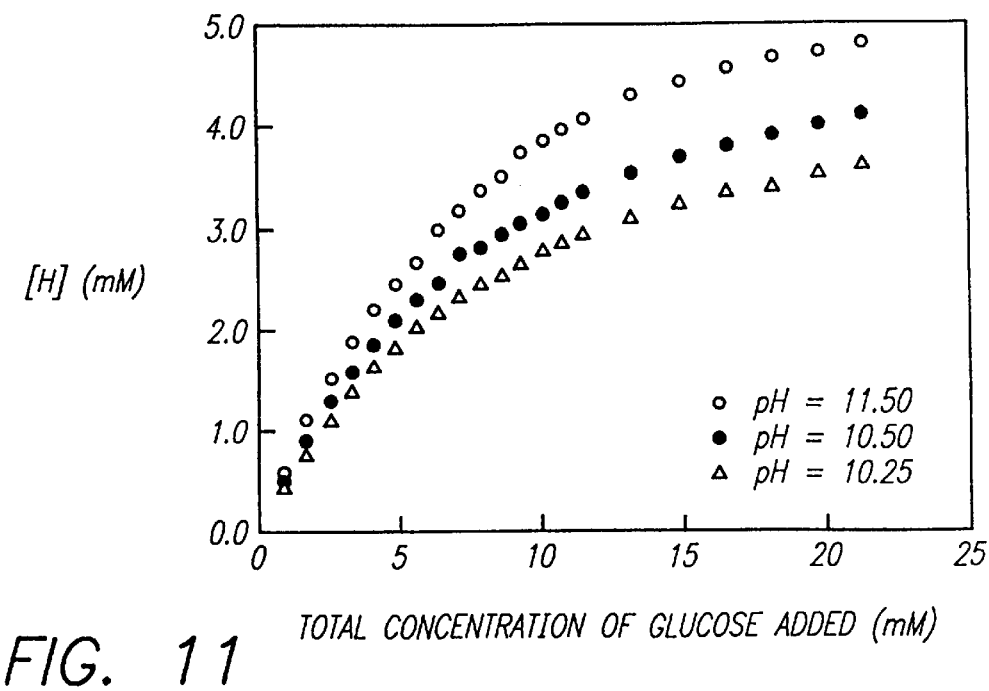

Glucose Rebinding Studies a) Glucose Rebinding to Polymer I at pH 11.50, 10.50 and 10.25 by pH Static Titration:

Polymer I (0.5 9) was suspended in 5 mL of pH 11.50, 10.50 or 10.25 NaOH solution in the pH titration vessel maintained at 25° C. by a constant temperature water bath. The pH of the suspension was adjusted as necessary by addition of 6N sodium hydroxide solution to maintain the starting pH. A solution of D-(+)-glucose with concentration of 0.208 M and pH of 11.50, 10.50 or 10.25 was titrated into the polymer suspension sequentially. After each addition, 0.10 N sodium hydroxide solution was added to maintain pH of the system constant. The system was kept stirring for a few minutes until equilibrium was reached. The volumes of the glucose solution injected and of the 0.10 N sodium hydroxide solution added were recorded for data analysis. The data in terms of the total concentration of released protons versus glucose concentration are plotted in FIG. 11 for examples performed at the three values of pH.

b) Glucose Rebinding to Polymer II at pH 10.25 by pH Static Titration:

Polymer II (0.100 g) was suspended in 0.980 mL of pH 10.25 NaOH solution in a pH titration vessel, which was kept at 25° C. by a constant temperature water bath. The pH of the suspension was adjusted to 10.25 by addition of 6N and 0.1 N sodium hydroxide solution and pH 10.25 NaOH solution (0.020 mL total). A solution of D-(+)-glucose with concentration of 0.500 M and pH of 10.25 was titrated into the polymer suspension sequentially. After each addition, 0.10 N sodium hydroxide solution was added to maintain pH of the system at 10.25. The system was kept stirring for a few minutes until equilibrium was reached. The volumes of the glucose solution injected and of the 0.10 N sodium hydroxide solution added were recorded for data analysis. The titration data are plotted in FIG. 12.

c) Glucose Rebinding to Polymer III at pH 10.25 by pH Static Titration:

Polymer III (0.100 g) was suspended in 0.980 mL of pH 10.25 NaOH solution in a pH titration vessel, which was kept at 25° C. by a constant temperature water bath. The pH of the suspension was adjusted to 10.25 by addition of 6N and 0.1 N sodium hydroxide solution and pH 10.24 NaOH solution (0.020 mL total). A solution of D-(+)-glucose with concentration of 0.500 M and pH of 10.25 was titrated into the polymer suspension sequentially. After each addition, 0.10 N sodium hydroxide solution was added to maintain pH of the system at 10.25. The system was kept stirring for a few minutes until equilibrium was reached. The volumes of the glucose solution injected and of the 0.10 N sodium hydroxide solution added were recorded for data analysis. The titration data are plotted in FIG. 12 d) Glucose Rebinding to Polymer IV at pH 10.25 by pH Static Titration:

Polymer IV (0.100 g) was suspended in 0.980 mL of pH 10.25 NaOH solution in a pH titration vessel, which was kept at 25° C. by a constant temperature water bath. The pH of the suspension was adjusted to 10.25 by addition of 6N and 0.1 N NaOH and pH 10.25 NaOH solution (0.020 mL total). A solution of D-(+)-glucose with concentration of 0.500 M and pH of 10.25 was titrated into the polymer suspension sequentially. After each addition, 0.10 N sodium hydroxide solution was added to maintain pH of the system at 10.25. The system was kept stirring for a few minutes until equilibrium was reached. The volumes of the glucose solution injected and of the 0.10 N sodium hydroxide solution added were recorded for data analysis. The titration data are plotted in FIG. 12.

Figure 12:
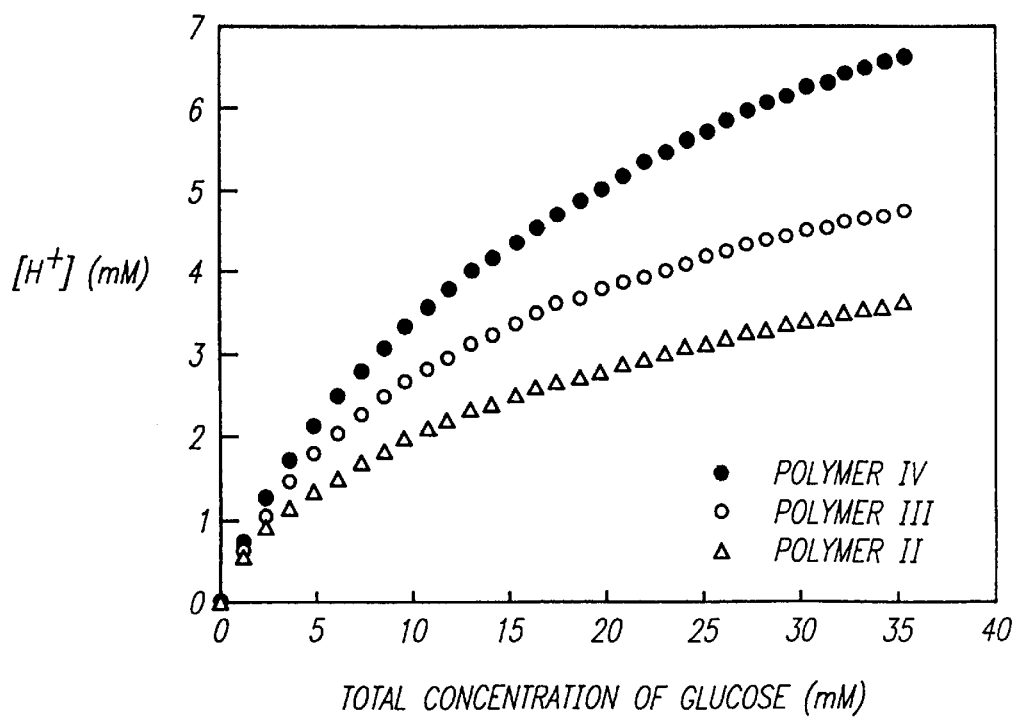

FIG. 12 compares the titration results for polymers II to IV at pH 10.25 in terms of protons released versus glucose concentration. The largest total signal per unit weight of polymer is provided by polymer IV, made with the largest amount of polymerizable metal complex. This polymer also gives the most linear response, with respect to protons released versus glucose concentration.

EXAMPLE 9

Preparation Of Polymers Using Ethylene Glycol As The Template And Msty-TACN-Cu$^{2+}$ As The Polymerizable Metal Complex And Glucose Rebinding To The Polymers This example demonstrates that polymers prepared using ethylene glycol as a template do not release as many protons in the presence of glucose as the analogous polymers prepared using the sugar analog methyl-β-D-glucopyranoside as the template (Example 8). Thus while different molecules can serve as a template during synthesis of these selective sensor materials, structural analogs of the target molecule (here, glucose) are likely to yield the best materials.

Polymers IIe and IVe are rigid polymers prepared using the same polymerization conditions and ratios of functional monomer Msty-TACN-Cu$^{2+}$ (Cu(II)-[1-(4'-vinylbenzyl)-1,4,7-triazacyclononane]) to crosslinker MBA (N,N'-methylenebisacrylamide) as for polymers II and IV listed in Table 5 of Example 8. Thus the performance of these materials can be compared directly to that of polymers II and IV of Example 8. The synthesis and behavior of the polymers in glucose rebinding studies is presented.

Synthesis of Polymers IIe and IVe.

Polymers of molar ratio Msty-TACN-Cu$^{2+}$ monomer to crosslinker MBA were prepared as described in Example 8 for polymers II and IV. The only difference was that ethylene glycol was used as the template instead of methyl-β-D-glucopyranoside. Polymer IIe was prepared using 0.1011 g of Msty-TACN-Cu$^{2+}$, 21.0 mL (0.375 mmol) of ethylene glycol, 0.621 g MBA and 9 mg AIBN. Polymer IVe was prepared using 0.1011 g Msty-TACN-Cu$^{2+}$, 21.0 mL (0.375 mmol) of ethylene glycol, 0.3854 g MBA and 9 mg AIBN.

Figure 13:
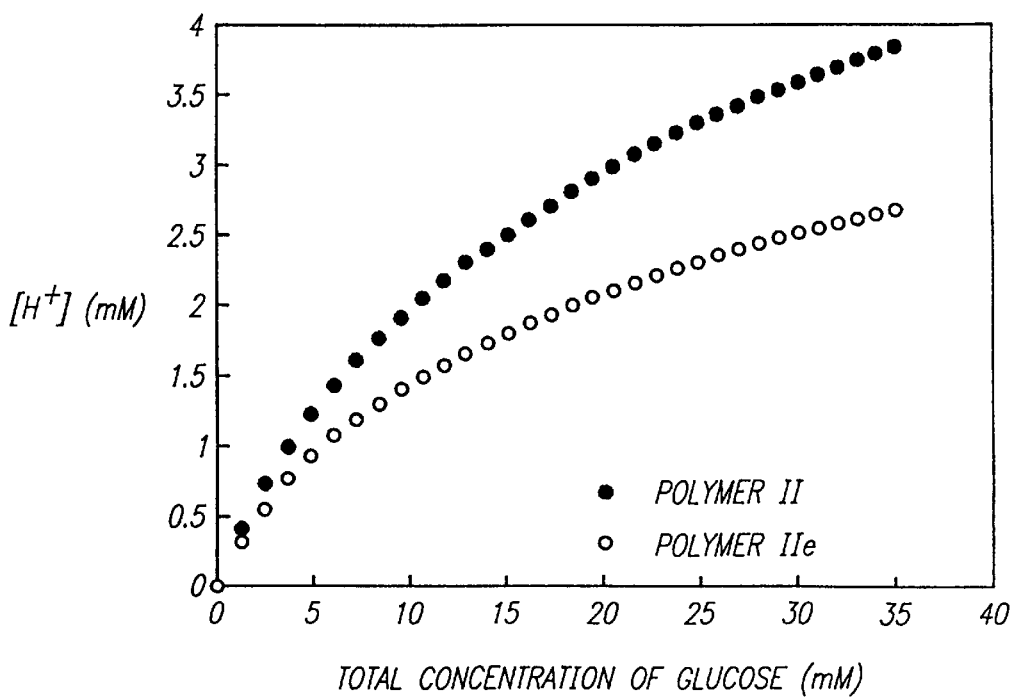
Figure 14:
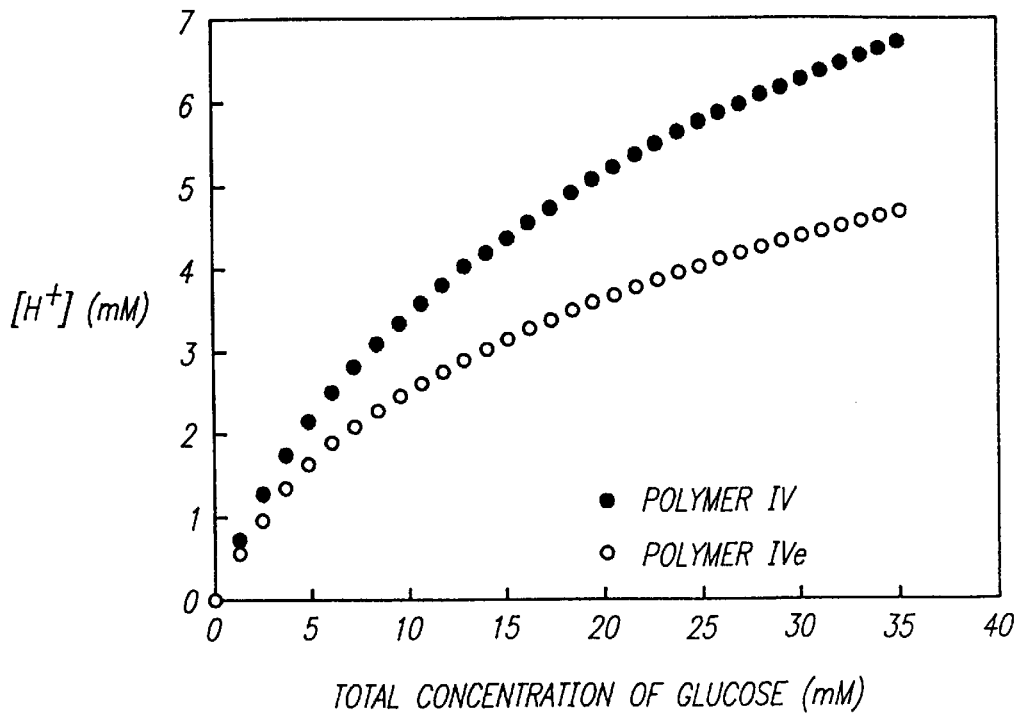

Glucose Rebinding Studies a) Glucose Rebinding to Polymer II at pH 10.25 by pH Static Titration:

Glucose rebinding was measured as described in Example 8. The titration data are plotted in FIGS. 13 and 14. Also plotted, for comparison, are the titration data for polymers II and IV, made using methyl-β-D-glucopyranoside as the template (Example 8).

EXAMPLE 10

Binding of Other Substrates to Polymer Prepared Using Methyl-β-D-glucopyranoside as the Template This example shows the binding of several substrates to glucopyranoside-imprinted polymer IV of Example 8 and the protons released upon binding. The substrates investigated are D-glucosamine, urea, lactic acid and the amino acid alanine. These are compounds commonly found in serum and other biological samples that might be monitored for glucose by the current invention. Thus this example illustrates a method by which potential competing signals from components in the sample other than glucose can be evaluated under different operating conditions and with different polymers. Furthermore, this example demonstrates the potential application of the current invention to the detection and measurement of different compounds.

D-Glucosamine Binding Studies on Polymer IV at pH 10.25 by pH Static Titration:

Polymer IV (0.100 g) from Example 8 was suspended in 0.980 mL of pH 10.25 NaOH solution in a pH titration vessel, which was kept at 25° C. by a constant temperature water bath. The pH of the suspension was adjusted to 10.25 by addition of 6N and 0.1 N sodium hydroxide solution, and pH 10.25 NaOH solution (0.020 mL total). A solution of D-glucosamine with concentration of 0.500 M and pH of 10.25 was titrated into the polymer suspension sequentially. After each addition, 0.10 N sodium hydroxide solution was added to maintain pH of the system at 10.25. The system was kept stirring for a few minutes until equilibrium was reached. The volumes of the glucose solution injected and of the 0.10 N sodium hydroxide solution added were recorded for data analysis. The titration data are plotted in FIG. 15, along with the data for glucose binding.

Figure 15:
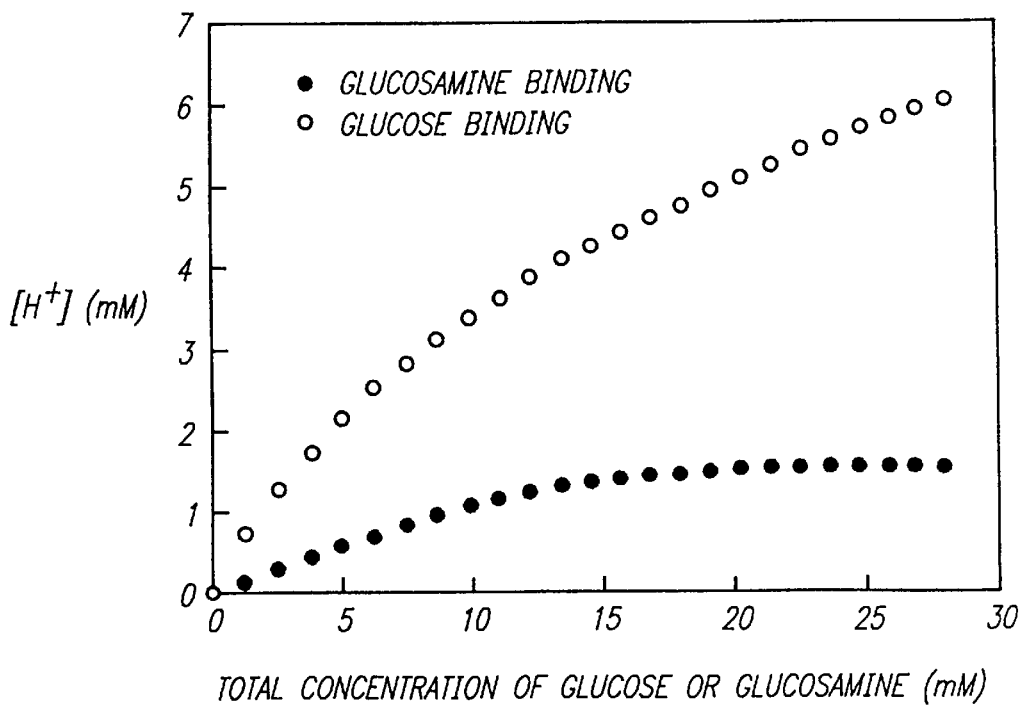
Figure 16:
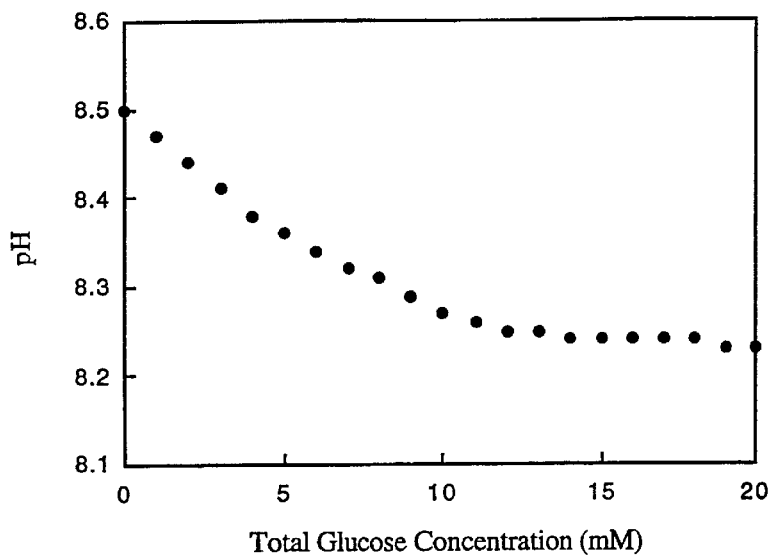

D-Glucosamine binds well to polymer IV (2) at pH 10.25. However, it releases fewer protons than glucose does at the same concentration (FIG. 15).

Since glucosamine can release protons upon binding to the polymer, this method is useful for monitoring its concentration in solution, provided large concentrations of other, competing compounds such as glucose are not present. Other conditions of pH or the use of other metal complexes selective for glucosamine can be investigated in order to enhance the proton release.

Urea Binding

Urea caused very little change in pH when titrated into a suspension of polymer IV under the same conditions as used for D-glucosamine titration.

Lactic Acid Binding

Lactic Acid (6) should be able to bind to polymer IV (2) well at pH 10.25. However, at high pH, its binding to Cu(TACN) is not expected to release proton (see Scheme 1 below). Titration of 0.5M, pH 10.25 lactic acid solution into a suspension of 100 mg of polymer IV in 1.00 mL water (pH=10.25) did not change the pH of the polymer mixture very much. At the beginning of the titration, the pH slightly increased (Table 6). As more lactic acid solution was added, the pH went down a small amount. Overall, the pH changes were very small. Thus lactic acid should not interfere with the signal generated by glucose during glucose monitoring of samples containing small amounts of lactic acid.

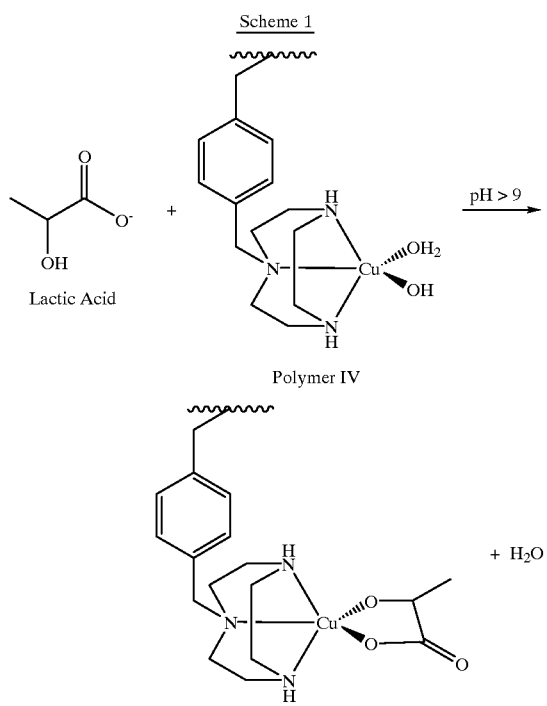

Scheme 1

TABLE 6 pH depression titration of polymer IV with lactic acid

| titration No.# | $V_{acid}$ (L) | pH |
|---|---|---|
| 0 | 0.0 | 10.25 |
| 1 | 2.5 | 10.28 |
| 2 | 5.0 | 10.28 |
| 3 | 10.0 | 10.27 |
| 4 | 20.0 | 10.27 |

TABLE 6-continued pH depression titration of polymer IV with lactic acid

| titration No.# | $V_{acid}$ (L) | pH |
|---|---|---|
| 5 | 25.0 | 10.26 |
| 6 | 30.0 | 10.26 |
| 7 | 32.5 | 10.25 |
| 8 | 35.0 | 10.24 |
| 9 | 40.0 | 10.24 |
| 10 | 60.0 | 10.22 |

EXAMPLE 11

A Sensor Using Soluble Metal Complex [Cu(1,10-phenanthroline)(NO$_3$)$_2$] To Measure The Concentration Of Sugars And Other Molecules In Aqueous Solution At pH 8.5 Or Lower.

This example shows the use of [Cu(1,10-phenanthroline)(NO$_3$)$_2$] in conjunction with a pH detector or pH static measurement in accordance with the present invention in measuring the concentration of sugars and other related molecules in aqueous solution. This example demonstrates the sensor material's ability to respond to D-glucose under slightly alkaline conditions (pH 8.5).

Figure 27:
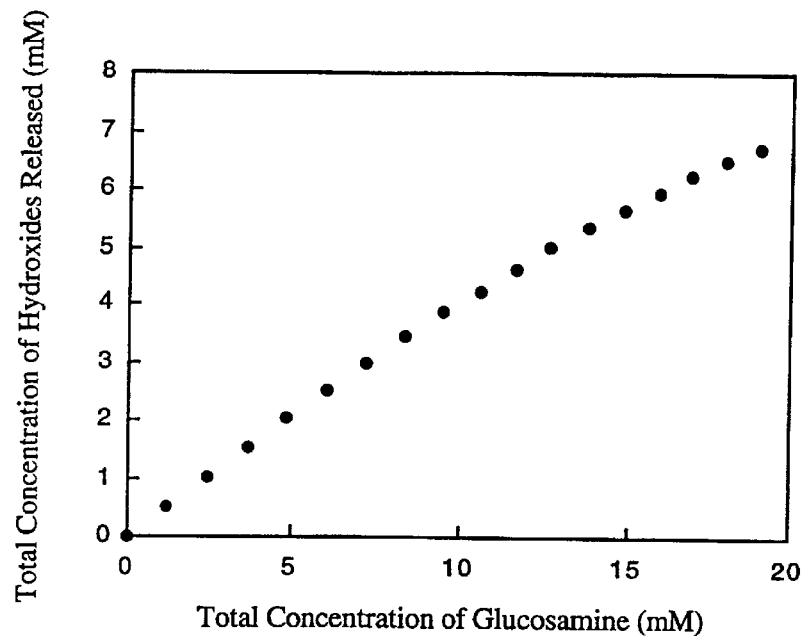

Measurement by pH Depression:

A 0.50 M aqueous solution of D-glucose was prepared at pH=8.5. A 2.00 mM solution of [Cu(1,10-phenanthroline)(NO$_3$)$_2$] at pH=8.5 was also prepared. The D-glucose solution was titrated slowly into 1.00 mL of the [Cu(1,10-phenanthroline)(NO$_3$)$_2$] solution, and the pH was monitored until saturation was nearly reached (as indicated by the very small changes in pH). FIG. 27 shows the pH response for this titration.

The concentration of an unknown sample of D-glucose can be determined by adding the sample to a solution containing the metal complex, measuring the resulting depression in pH and comparing that value to these calibration curves prepared with known quantities.

EXAMPLE 12

Synthesis Of Two Soluble Metal Complexing Compounds, [Cu(N$_2$O-9-ane)Cl$_2$] and [Cu(N$_2$S-9-ane)Cl$_2$]And Use For Sensing Of Sugars And Other Molecules In Aqueous Solution At Slightly Alkaline pH.

This example shows the preparation of two sensor materials, [Cu(N$_2$O-9-ane)Cl$_2$], and [Cu(N$_2$S-9-ane)Cl$_2$] in accordance with the present invention. These materials are useful for measuring the concentration of sugars and other molecules. This example demonstrates the sensor materials' ability to respond to D-glucose under slightly alkaline conditions (pH less than or equal to 8.5).

[Cu(N$_2$O-9-ane)Cl$_2$] Synthesis:

The free ligand N$_2$O-9-ane (N$_2$O-9-ane=1-oxa-4,7-diazacyclononane) was prepared according to literature procedures (Hancock, R. D. et al. "Macrocyclic Effect in Transition-Metal Ion Complexes of a Mixed (Nitrogen, Oxygen) Donor Macrocycle," *J. Am. Chem. Soc.* 104, 291–292, (1982)).

N$_2$O-9-ane (260 mg, 2 mmol) was dissolved in 2 ml of water at room temperature and was vigorously stirred with a magnetic stir bar. CuCl$_2$·2H$_2$O (340 mg, 2.00 mmol) was very slowly added to above solution. Water was then slowly evaporated, and [Cu(N$_2$O-9-ane)Cl$_2$] was obtained as blue plate crystals and was recrystallized from water.

[Cu(N$_2$O-9-ane)Cl$_2$] Synthesis:

The ligand N$_2$S-9-ane·2HBr (N$_2$O-9-ane=1-thia-4,7-diazacyclononane dihydrobromide) was prepared according to literature procedures (Hart, S. M. etal "Stability, Electronic Spectra, and Structure of Transition-metal Ion Complexes of a Novel Mixed-donor (Nitrogen-Sulphur) Macrocycle, 1,Thia-4,7-diazacyclononane," *J. Chem. Soc. Dalton Trans.*, 1601–1606, (1983)). The N$_2$S-9-ane·2HCl (N$_2$O-9-ane=1-thia-4,7-diazacyclononane dihydrochloride) was obtained by eluting N$_2$S-9-ane·2HBr through a column of Dowex 50WX2-400 ion-exchange resin with 1.5 N HCl. White solid of N$_2$O-9-ane·2HCl was obtained after water was removed. The solid was further purified by recrystallization in methanol. $^1$HNMR (CDCl$_3$) δ 3.0 (m, 4H, CH$_2$S), 3.4 (m, 4H, CH$_2$N), and 3.7 (s, 4H, NCH$_2$CH$_2$N).

N$_2$O-9-ane·2HCl (219 mg, 1 mmol) and NaOH (80 mg, 2 mmol) were dissolved in 2 ml of water, and was vigorously stirred with a magnetic stir bar. CuCl$_2$·2H$_2$O (170 mg, 1.00 mmol) was very slowly added to above solution. Water was then slowly evaporated, and [Cu(N$_2$O-9-ane)Cl$_2$] was obtained as blue crystals, and was recrystallized from water.

Measurement of D-glucose Concentrations by pH Titration.

Figure 17:
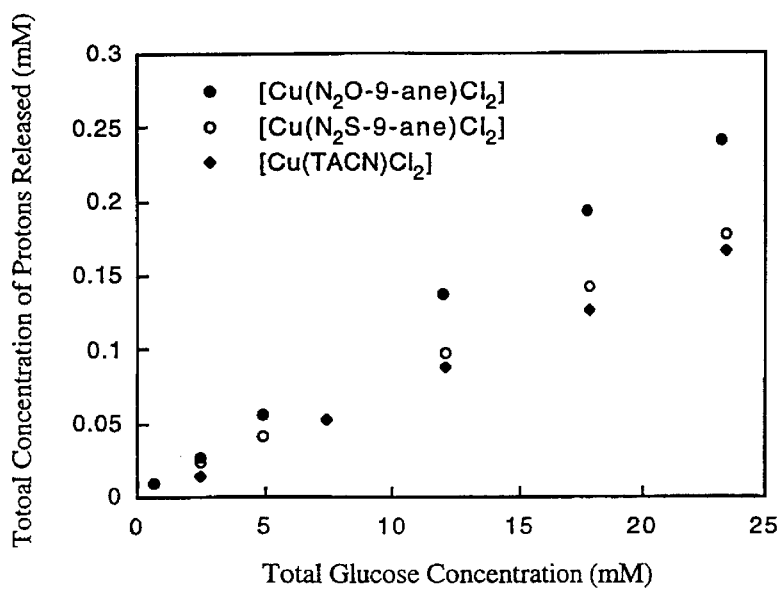

Solution of the three copper(II) complexes, [Cu(N$_2$O-9-ane)Cl$_2$], [Cu(N$_2$S-9-ane)Cl$_2$] and [Cu(TACN)Cl$_2$], at 10.0 mM concentration and NaCl concentration of 150 mM were prepared without pH adjustment. An aqueous solution of 0.500 M D-glucose with NaCl concentration of 150 mM and pH of 8.00 was prepared. 2.00 mL of each of the solutions containing the metal complexes (prepared according to literature procedures (Schwindinger, W. F. et al., "Molecular Structure of Dichloro(1,4,7-triazacyclononane)copper(II), a Macrocyclic Triamine Complex with an Unusually Small Formation Constant," *Inorg. Chem.* 19, 1379–1381, (1980)) were introduced into the titration vessel of a Brinkman pH titrator in separate experiments. The vessel was sealed, purged thoroughly with N$_2$, and equilibrated to 25° C. by a constant temperature water bath. The pH of the solutions were adjusted to 8.50 with the addition of 6.0 N and 0.10 N sodium hydroxide. Then the D-glucose solution was titrated into the Cu(II) solutions. After each injection of D-glucose the pH of the solution decreased, and the pH titrator automatically added 0.0100 N sodium hydroxide to bring the solution pH back to the original value. The volumes of the D-glucose solution injected and the volumes of the 0.0100 N sodium hydroxide added to maintain constant pH were recorded and are plotted in FIG. 17.

At pH 8.5, the [Cu(N$_2$O-9-ane)Cl$_2$] provides higher sensitivity for measuring the glucose concentration than [Cu(TACN)Cl$_2$]. [Cu(N$_2$S-9-ane)Cl$_2$] offers slightly better sensitivity than ICu(TACN)Cl$_2$].

The concentration of an unknown sample of D-glucose can be determined by adding a known quantity to any of these metal complex solutions, measuring the resulting depression in pH and comparing that value to these calibration curves prepared with known quantities.

Metal Complex/Target Molecule Ligand Exchange

Certain metal complexes, such as Cu(II) complexes, undergo rapid and reversible ligand exchange (ligand substitution) reactions with a variety of metal binding substrates, such as sugars, amino acids, amino alcohols, among many others. One or more ligands originally on the metal complex are replaced by the substrates in these exchange reactions, and the ligands are released into the solution. In aqueous or mixed aqueous/organic solvents, protons or hydroxide ions can be generated as a result of ligand exchange. Thus metal complexes which result in the net release of a ligand can be used with appropriate detectors as sensors for the metal binding substrates (target molecules). Thus, by monitoring the pH changes of the solution, or other properties of the system which are sensitive to pH, the concentration of the target molecules can thus be measured when binding of the target molecule results in release of protons or hydroxide ions. In aqueous and non-aqueous solutions, other detectable ligands can be released. The concentration of target molecule can be determined by measuring the detectable ligand released from the metal complex.

The sensor includes specific types of metal ion complexes that bind to sugars and other molecules in aqueous, mixed aqueous/organic, or organic solution. Metal ion complexes which may be used in accordance with the present invention can be any suitable metal complex, monomeric, dimeric or clustered, that is stable in the chosen solvent (or sample). These metal ion complexes are preferred to have the following characteristics: 1) one of the ligands, or one or more chelating groups of a ligand, can hold the metal ion tightly; and 2) there is at least one additional ligand, or one or more chelating groups of a ligand that binds to the metal ion loosely enough that it can be substituted and released from the metal ion by the target analyte. Preferred exemplary metal complexes are those of the following general composition

where M is a metal ion such as Cu$^{2+}$, Fe$^{2+}$, Fe$^{3+}$, Pb$^{2+}$, Co$^{3+}$, Ni$^{2+}$, Hg$^{2+}$, Al$^{3+}$, or the like. L$_1$ is one or more ligand(s) that binds to the metal very strongly (and is not displaced). L$_2$ is one or more ligand(s) that binds less strongly to the metal than L$_1$ does and therefore can be exchanged by the target molecule. The net result of the exchange reaction is a measurable species. A metal complex used in a sensor in accordance with the present invention does not necessarily have the above formula when first introduced into the sensor device. The metal complex may need pre-treatment before being used as a sensing element. Pre-treatment is a process in which other compound(s) are added to solution or suspension of the metal complex, such that the newly formed complex then undergoes the ligand-exchange reaction with the target analyte. In other words, the appropriate complex can be prepared and regenerated in situ. Measurable chemical species (L$_2$) are released as a result of the ligand exchange reaction. These species can be measured directly or indirectly. Exemplary ligand species (L$_2$) includes ionic species such as F$^-$, Cl$^-$, Br$^-$, I$^-$, SCN$^-$, OCN$^-$, NO$_3^{3-}$, ClO$^{3-}$, H$_2$PO$_4^-$, HPO$_4^{2-}$, PO$_4^{3-}$, HSO$_3^-$, SO$_3^{2-}$, HSO$_4^-$, SO4$^{2-}$, HS$_2$O$_3^-$, S$_2$O$_3^{2-}$, HCO$_3^-$, CO$_3^{2-}$, NH$_4^+$, C$_2$O$_4^{2-}$, IO$_3^-$, BH$_4^-$, SO$_3^-$NH$_2^-$, H$_2$A$_2$O$_4^-$, HAsO$_4^{2-}$, AsO$_4^{3-}$, CrO$_4^{2-}$, Cr$_2$O$_7^{2-}$, Fe(CN)$_6^{4-}$, PdCl$_4^{2-}$, PdCl$_6^{2-}$, PtCl$_4^{2-}$, PtCl$_4^{2-}$, PtCl$_6^{2-}$, Pt(CN)$_4^{2-}$, AlCl$_4^-$, AlF$_6^{3-}$, PF$_6^-$, SiF$_6^{2-}$, HS$^-$, IO$_3^-$, MnO$_4^-$, SeO$_4^{2-}$, TiO$_2^-$, WO$_4^{2-}$, ReO$_4^-$, TeO$_3^{2-}$, c TeO$_6^{6-}$, SnO$_3^{2-}$, MoO$_4^{2-}$, VO$_3^-$, BO$_2^-$, BO$_3^{3-}$, B$_4$O$_7^{2-}$, BF$_4^-$, BrO$^-$, and ClO$^-$. Exemplary released species (L$_2$) also include amines such as NH$_3$, amino acids, phenol, carboxylic acids such as acetic acid, amino alcohols such as glucosamine, diols such as 1,4-amhydroerythritol.

The above released ligand species can be detected using well-known conventional analytical methods. The released ligand could be electroactive and thereby detected electrochemically. Other exemplary methods include using ion selective electrodes; using spectrophotometric methods if the species are colored, fluorescent, phosphorescent, chemiluminescent or exhibit other useful optical properties. The released species can be detected by optical methods if they are bound to or otherwise have incorporated an optically detectable group or compound, such as fluorescent compounds, pyrene, rhodamine and naphthalene. Other reactive species can be added to convert the released species into optically detectable species. Alternatively, other optically detectable compounds whose optical properties can be quenched by the released species can be used in the sensor. Exemplary compounds that can be used to induce optical activities or whose optical activities could be reduced or quenched include fluorescent indicators, such as N-(3-sulfopropyl) acridinium and nigericin (fluorescent $Cl^-$ indicators); lucigenin (whose fluorescence can be quantitatively quenched by $Cl^-$); fluorescamine (which reacts in milliseconds with primary aliphatic amines to yield a fluorescent derivative); m-dansylaminophenylboronic acid (which reacts with vicinal diols and certain amino alcohols to form fluorescent derivative); 2,3-diaminoaphthalene (which reacts with $NO_2^-$ to form fluorescent product 1 H-naphthalene); 5,5'-dithiobis-(2-nitrobenzoic acid) (for colorimetric thiol quantitation); pH indicators such as fluorescein and its derivatives.

The sensors in accordance with the present invention may be used to detect and measure the presence of a wide variety of target molecules in solution. The sensors are suitable for detecting sugars such as glucose, mannose and other monosaccharides, lactic acid, sialic acid, aminosugars such as glucosamine, disaccharides, trisaccharides, oligosaccharides, polysaccharides (such as starch and glycogen), sugar-amino acids, sugar-peptides and glycoproteins. A wide variety of other target molecules that bind metal ions, such as certain adrenocortical steroids, certain drugs of abuse and important metabolites, can be measured using these sensor devices. Exemplary target molecules include deoxycortisol, cortisol, cortisone, aldosterone, glycerol, vanillylmandelic acid, serotonin, 5-hydroxyindoleacetic acid, 3-methoxytyramine, homovanillic acid, ascorbic acid, diols such as 1,4-anhydroerythritol, ethyleneglycol, amino acids such as phenylalanine and tryptophan, amino alcohols such as dopamine, catechol, ephedrine, pseudoephedrine, metanephrine, norephedrine, propanolol, 4-methylpropanolol, N-desisopropylpropanolol, amphetamines such as amphetamine and methamphetamine, barbiturates, benzodiazepines, cannabinoids such as tetrahydrocannabinol (THC) and its metabolite carboxy-THC, cocaine and its metabolites benzoylecgonine and ecgonine methyl ester, opiates and their metabolites such as morphine, codeine, fentanyl, hydromorphone, oxycodone, meperidine, naloxone, morphine glucuronide. The sensors are also suitable for detecting ionic species such as $F^-$, $Cl^-$, $Br^-$, $I^-$, $SCN^-$, $OCN^-$, $NO^{3-}$, $ClO_4^-$, $H_2PO_4^-$, $HPO_4^{2-}$, $PO_4^{3-}$, $HSO_3^-$, $SO_3^{2-}$, $HSO_3^-$, $SO_4^{2-}$, $HS_2O_3^-$, $S_2O_3^{2-}$, $HCO_3^-$, $CO_3^{2-}$, $NH_4^+$, $C_2O_4^{2-}$, $IO_3^-$, $BH_4^-$, $SO_3NH_2^-$, $H_2AsO_4^-$, $HAsO_4^{2-}$, $AsO_4^{3-}$, $CrO_4^{2-}$, $CrO_7^{2-}$, $Fe(CN)_6^{4-}$, $PdCl_4^{2-}$, $PdCl_6^{2-}$, $PtCl_4^{2-}$, $PtCl_4^{2-}$, $PtCl_6^{2-}$, $Pt(CN_4)_4^{2-}$, $AlCl_4^-$, $AlF_6^{3-}$, $PF_6^-$, $SiF_6^{2-}$, $HS^-$, $IO_3^-$, $MnO_4^-$, $SeO_4^{2-}$, $TiO_2^-$, $WO_4^{2-}$, $ReO_4^-$, $TeO_3^{2-}$, $TeO_6^{6-}$, $SnO_3^{2-}$, $MoO_4^{2-}$, $VO_3^-$, $BO_2^-$, $BO_3^{3-}$, $B_4O_7^{2-}$, $BF_4^-$, $BrO^-$, and $ClO^-$. The general characteristics of or requirement for a suitable target molecule is that it must be able to undergo ligand exchange with the sensor and release protons, hydroxide ions or other detectable species when used at an appropriate pH and sample environment. Sensors which are capable of measuring the concentration of glucose in biological samples are preferred because of the importance of glucose in the diagnosis and treatment of diabetes and other disorders. The concentration range which is typically of interest in biological samples is 0–25 mM.

In the same manner as discussed in the first part of this description, one or all of the chelating ligands ($L_1$) from which the metal complexes are formed may be chemically modified to 1) have a polymerizable functionality for copolymerization or 2) have functional groups appropriate for covalent attachment to a solid surface. The metal ion for a particular metal ion complex is chosen such that the target molecule binds the complex formed by the metal ion and chelating ligand rapidly and reversibly in the presence of the sample solution and that a measurable chemical species is released upon target analyte binding. The ligands of the metal complexes can be tailored so that only certain analytes with both the right metal binding functional groups and the right binding affinity can undergo the ligand exchange reaction with the sensor metal complex and release the species that is ultimately detected.

Two exemplary metal complexes are shown in FIG. 18(a). The $Cu^{II}$ complexes 1 and 2 can be formed in aqueous solution by mixing more than one equivalent of 1,4-anhydroerythritol (cis-diol) (3) or carbonate (4) with 1 equivalent of Cu-TACN (triazacyclononane) complex (5) at slightly alkaline conditions. As shown in FIG. 19, when solutions of metal binding substrates, such as amino alcohol (6), α-hydroxyl carboxylic acid (8), amino acid (10) and diol (12) are added to these complexes, protons or hydroxide ions are generated as a result of ligand exchange. The protons or hydroxides released are proportional to the concentration of the target analytes.

In the two exemplary sensor complexes shown in FIG. 18(a), the strong binding ligand ($L_1$) is 1,4,7-triazacyclononane and the exchangeable ligands ($L_2$) are cis-diol in 1 and carbonate in 2.

Additional exemplary strong binding ligands ($L_1$) are nitrogen-based multidentate ligands of the same type set forth in the first part of this description and are briefly summarized in FIG. 20. In FIG. 20, R is a polymerizable functional group, which is selected from styrene, methacrylate, acrylate, vinyl, vinyl ether, vinyl acetate, trialkoxysilane, dialkylchlorosilane, epoxy, and the like.

Referring to FIG. 19, upon binding of a target analyte to the metal complexes, either protons or hydroxides are released into solution. The release of protons or hydroxides provides a direct indication of the concentration of free sugar or other target analyte in the contacting solution. It is preferred that the released protons or hydroxides be measured by monitoring their effect on solution pH. This can be done, for example, using a pH electrode, field effect transistor (FET), light-addressable potentiometric sensor (LAPS), or other device which provides an electrical signal or, alternatively, using a chemical probe whose optical properties (fluorescence or absorption) or other properties (e.g. conductivity) are sensitive to pH. The probe then provides an optical or other signal which can be read to determine the sugar concentration. Alternatively, static pH titration techniques can be employed. Static titration involves addition or generation of a suitable base or acid, such as sodium hydroxide or hydrogen chloride, to maintain a constant pH. The amount of base or acid which must be added to maintain a constant pH provides a direct indication of the amount of protons or hydroxides released upon analyte binding.

The metal complexes are used in solution, or anchored to a support in the same manner as the metal complexes described in the first part of this description. It is preferred that the metal complex be attached to or physically entrapped in a support structure. Any number of methods may be used to attach the metal complexes, and any number of different support materials and physical forms may be utilized. Exemplary ligand support materials include silicon, glass, quartz, ceramics, organic or inorganic polymers, and zeolites and other inorganic materials. The ligand support structure can be almost any solid form which provides a surface to which the metal complex may be attached. Exemplary forms include metal electrodes, beads, porous polymer beads, particles or membranes, plates, threads, fibers and solid-state electronic devices such as FETs or LAPS devices and the like. The metal complexes may be attached to these materials and forms covalently or noncovalently, using methods well known to those practiced in the art.

In a preferred embodiment, the metal complexes include a polymerizable moiety which allows the complex to be copolymerized with monomers and crosslinking agents to form porous polymeric materials. Polymerizable metal complexes can be incorporated via co-polymerization directly into the support structure. The polymer can be formulated into appropriate forms or configurations (membrane, beads, coated or deposited on surfaces, etc.) using methods well known to those practiced in the art. In addition, appropriate pH-sensitive chromophores or fluorophores can be incorporated during polymerization for optical detection of target molecule binding. The resulting polymer, whether it be in the form of a powder, micro beads or a larger structure, can be used directly in a sensor in conjunction with a pH monitoring or other detection system. Exemplary functional groups which are attached to the metal complex to form polymerizable metal complexes are set forth in detail above.

Exemplary monomers and cross-linkers which may be co-polymerized with the polymerizable metal complex include styrene, methyl methacrylate, 2-hydroxyethyl methacrylate, 2-hydroxyethyl acrylate, methyl acrylate, acrylamide, vinyl ether, vinyl acetate, divinylbenzene, ethylene glycol dimethacrylate, ethylene glycol diacrylate, pentaerythritol dimethacrylate, pentaerythritol diacrylate, N,N'-methylenebisacrylamide, N,N'-ethylenebisacrylamide, N,N'-(1,2-dihydroxyethylene)bis-acrylamide, trimethylolpropane trimethacrylate, etc. The choice of co-monomer and cross-linker will be dictated by the chemical (hydrophilicity, local pH, chemical stability, degree of crosslinking, ability to graft to or be deposited on other surfaces, interactions with other molecules, etc.) and physical (porosity, morphology, mechanical stability, conductivity, etc.) properties desired for the sensor element.

Figure 18B:
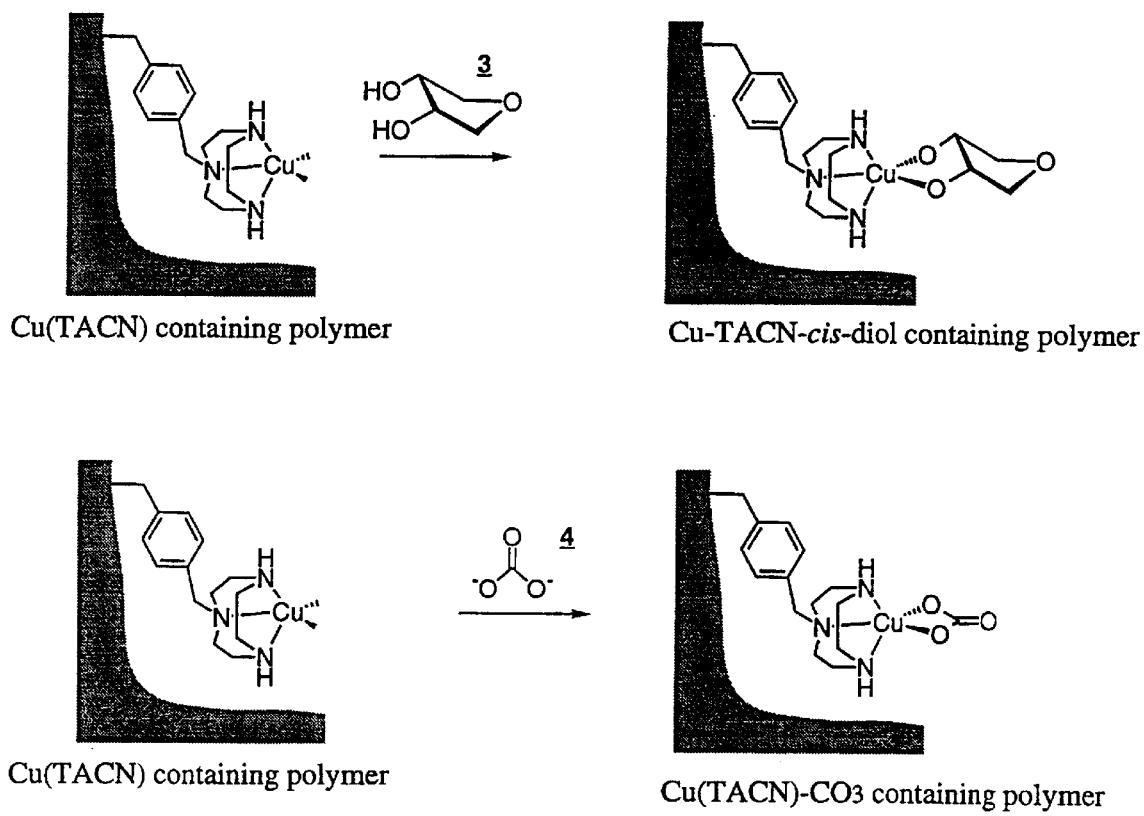
FIG. 18(b) depicts how compounds 1 and 2 can be incorporated into a polymer support by combining a Cu(TACN)-containing polymer with ligands 3 and 4, respectively, under appropriate conditions.

An exemplary incorporation of complex Cu-TACN-cis-diol (compound 1 of FIG. 18(a)) and Cu-TACN-CO$_3$ (compound 2 of FIG. 18(a)) into polymer support is illustrated in FIG. 18(b). A macroporous Cu(TACN)-containing polymer was synthesized first as described above. The two empty (solvent component occupied) coordinated sites of the Cu(II) in this polymer are then occupied by cis-diol (3) or carbonate (4) upon addition of more than one equivalent of 3 or 4 into the suspension at alkaline condition. Polymers incorporated with metal complexes Cu-TACN-cis-diol (1) and Cu-TACN-CO$_3$ (2) respectively are then formed. Suspensions of these two polymers can be used in a sensor to measure the concentration of metal binding substrates, as illustrated in Examples 13, 14 and 15.

The metal ion complexes with substitutable ligand ($L_2$) are especially suitable for measurement of sugars and related molecules, particularly near or slightly above physiological pH (pH 7–9) (FIG. 21). This feature is desirable for monitoring glucose concentration. The high buffer capacity of biological samples at physiological pH can pose a problem for potentiometric enzyme sensors (Meyerhoff et al. "Current status of the glucose sensor," *The Endocrinologist* 6, 51–58, (1996)). In human interstitial fluid, at approximately pH 8, the buffer capacity reaches a minimum. Thus the pH region from about 7.4 to 9 provides a good window for monitoring target analytes in human body fluids by the current invention, when pH-based detection is used.

For the complex to show high affinity for neutral sugars such as glucose, a preferred complex would have net positive charge(s), and the binding strength of the exchangeable ligand to the metal ion in the complex is preferred to be relatively weak, yet strong enough so the complex can still be formed in solution. The preferred metal cations are Cu(II) and Fe(III). The binding constant of a preferred ligand $L_1$ to the metal ion should be between $10^8$ to $10^{15}$ M$^{-1}$. FIG. 20 shows some exemplary ligands. They include linear heteronuclear ligands, cyclic heteronuclear ligands, 1,10-phenanthroline and phenanthroline analogs, and diaminophenanthrene and its analogs. Adding an electron withdrawing such as trifluoromethyl (CF$_3$), or pentafluorophenyl (C$_6$F$_5$) to a nitrogen in the ligand, or using oxygen or sulfur to substitute nitrogen in these ligands could improve their binding to target molecules such as glucose. Also, incorporating the complexes formed by these ligands into polymers increases their stability in aqueous conditions, should their corresponding complexes in solution be unstable or have poor solubility.

Ligand exchange on soluble and polymeric metal complexing materials enables the generation of the chemical signal (exchangeable ligand) which is the basis for the detection of the target molecule. However, to be useful in a continuous flow device, the local concentration of the ligand to be exchanged (such as cis-diol) must be maintained relatively constant. Co-immobilizing the exchangeable ligands ($L_2$) with the metal complex on a solid support keeps them in the vicinity of metal ions, thus maintaining their local concentration. Such co-immobilized ligands can enable the metal complexing polymers to be used as sensor materials in continuous flow devices. An exemplary preparation of ligand-co-immobilized metal complexing polymer is illustrated in FIG. 22. If cis-diol (3) is the exchangeable ligand, a polymerizable analog of it is first synthesized (33). This analog (an excess of which can be used) is then allowed to form a complex (34) with Cu-Styryl-TACN (32). This complex is then incorporated into polymers (35). Under slightly alkaline conditions, a substrate such as D-glucosamine (36) should be able to displace the cis-diol of the polymer and generate hydroxide. However, the cis-diol will remain close to the metal ion after being displaced, and it will rebind the metal ion (and generate protons), should the surrounding glucosamine concentration decrease.

Preferred exemplary metal complexes for continuous monitoring have the following formula:

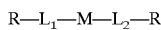

where M is a metal ion such as Cu$^{2+}$, Fe$^{2+}$, Fe$^{3+}$, Al$^{3+}$, Pb$^{2+}$, Co$^{3+}$, Ni$^{2+}$ or Hg$^{2+}$. $L_1$ is one or more ligand(s) that binds to the metal very strongly. $L_2$ is one or more ligand(s) that binds to the metal weaker than $L_1$, and which can be exchanged by the target molecule. The displacement generates a measurable chemical species. R is the polymer support to which $L_1$ and $L_2$ are anchored. $L_1$ and $L_2$ could also be different functional groups that belong to the same ligand. In this case, $L_1$ is (are) the chelation group(s) that binds (bind) to the metal very strongly. $L_2$ is (are) the chelation group(s) that binds (bind) to the metal weaker than $L_1$ does, and can be exchanged by target molecules. Examples of practice for sensors utilizing ligand exchange are as follows:

EXAMPLE 13

Preparation and Use of a Sensor Polymer for Measuring D-glucose And D-glucosamine This example shows the preparation of a ligand exchange sensor polymer and its use in accordance with the present invention. The example also demonstrates the ability of the sensor material to undergo a ligand exchange reaction with target molecules and produce protons. This example uses [Cu(II)(1-vinylbenzyl-1,4,7-triazacyclononane)$SO_4$] ([styryl-TACN-$Cu^{2+}$]$SO_4$) as the polymerizable metal complex and carbonate as the exchangeable ligand in the polymer supported Cu(II) complex.

Synthesis of Cu(TACN) Containing Polymer:

The synthesis of Cu(TACN) containing polymer was according to that described in the previous examples. [Styryl-TACN-$Cu^{2+}$]$SO_4^{2-}$ (0.1010 g, 0.25 mmol) and Me-β-glucopyranoside (0.0508 g, 0.25 mmol) were dissolved in a vial containing 2 mL of methanol and 0.5 mL of pH 11.50 aqueous NaOH. The pH was further adjusted to 11.50 with addition of 1 N NaOH, and the solution was allowed to sit at room temperature for 30 min. The solution was then filtered into a vial containing crosslinking monomer N,N'-methylenebisacrylamide (MBA, 99%, purchased from Aldrich Co., Milwaukee, Wis.) (0.385 g, 2.50 mmol) and free radical initiator AIBN (2,2'-azo-bisisobutyronitrile, 9 mg). After freeze-pump-thawing for 4 cycles to degas the solution, the vial was sealed and heated at 65° C. The solution was polymerized at 65° C. overnight and at 70° C. for 36 hours. The resulting solid was ground into a fine powder and washed with 50/50 waterlmethanol, pH 4, to remove Me-β-Glucopyranoside. The resulting polymer was found to be 2.31% copper by elemental analysis. The blue powder was washed extensively with 100 mM EDTA, pH 8.0 to strip $Cu^{2+}$ in order to further remove the templates. The white powder was then washed with water to remove residual EDTA (copper 0.16% by elemental analysis), reloaded with 20 mM $CuSO_4$ solution, washed again with water and pH=3 aqueous HCl solution to remove free $Cu^{2+}$, frozen and lyophilized.

Pre-treatment of Cu(TACN) Containing Polymer with Carbonate:

The polymer (0.100 g, 0.034 mmol $Cu^{2+}$) was suspended in 1.00 mL 30 mM $Na_2CO_3$ in a titration vessel of a Brinkman pH titrator. The vessel was sealed, purged thoroughly with $N_2$, and equilibrated to 25° C. by a constant temperature water bath. The pH of the suspension was adjusted to 10.25. The resulting suspension could be directly used as sensor material. The suspension could be filtered to remove the aqueous supernatant and used, or it could be freeze-dried, and then be used as sensor material.

Measurement of D-Glucose with Carbonate Pre-treated Polymer and pH Static Titration:

An aqueous solution of D-glucose with a concentration of 0.500 M and a pH of 10.25 was prepared. This solution was titrated into the carbonate pre-treated polymer suspension in 2.5 μL or larger increments. After each injection of D-glucose, the pH of the solution decreased, and the automatic pH titrator automatically added 0.100 N NaOH solution to bring the solution pH back to the original value. The amount of sodium hydroxide added during the titration is equal to the amount of protons released from the sugar binding reaction. The volumes of the D-glucose solution injected and the volumes of the 0.100 N sodium hydroxide added to maintain constant pH were recorded and used to calculate the protons released. The results are plotted in FIG. 23.

Figure 23:
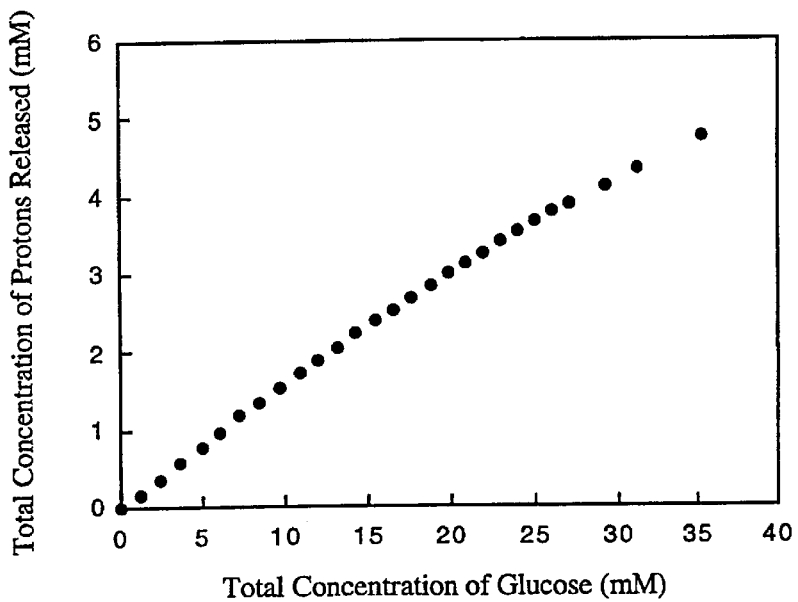

As can be seen from FIG. 23, the amount of sugar added to the solution is nearly linearly proportional to the total released proton concentration. A sensor incorporating the metal complexing polymer and a pH titration apparatus thus has provided a measure of the amount of glucose added to the solution. The concentration of sugar in an unknown sample can be determined by comparison of the protons released under comparable conditions to the protons released at the known glucose concentrations.

Measurement of D-Glucosamine Using the Carbonate Pretreated Polymer and pH Static Titration:

An aqueous solution of D-glucosamine with a concentration of 0.500 M and a pH of 10.25 was prepared. This solution was then titrated into the carbonate pre-treated polymer suspension in the titration vessel in 2.5 μL or larger increments. After each injection of D-glucose the pH of the solution decreased, and the pH titrator automatically added 0.100 N NaOH solution to bring the solution pH back to the original value. The volumes of the D-glucose solution injected and the volumes of the 0.100 N sodium hydroxide added to maintain constant pH were recorded and used to calculate the protons released. The results are plotted in FIG. 24.

Figure 24:
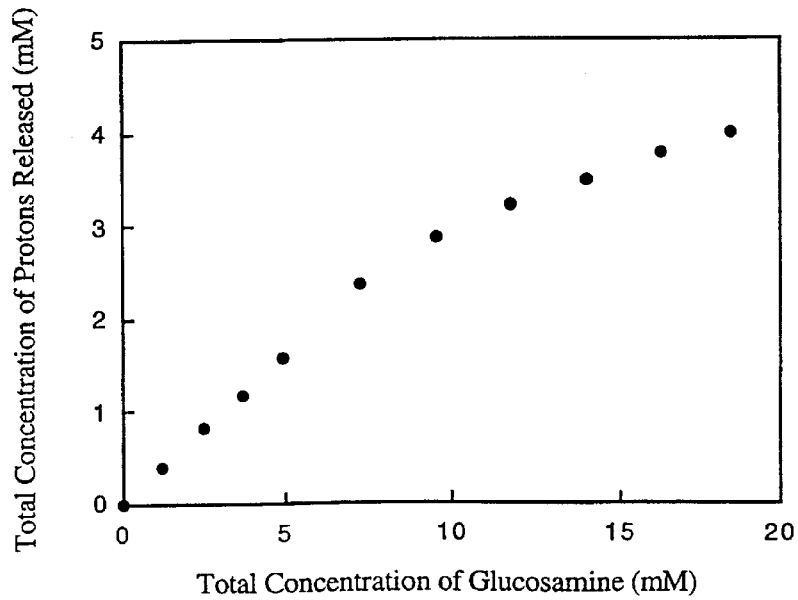

As can be seen from FIG. 24, the amount of protons released is proportional to the amount of glucosamine added to the solution. A sensor incorporating the metal complexing polymer and a pH titration apparatus thus has provided a measure of the amount of glucosamine added to the solution. The concentration of glucosamine in an unknown sample can be determined by comparison of the protons released under comparable conditions to the protons released at the known glucosamine concentrations.

Since glucosamine can release protons upon binding to the polymer, this method is useful for monitoring its concentration or the concentration of any other amino alcohols in solution, provided large concentrations of competing compounds such as glucose are not present.

EXAMPLE 14

Preparation and Use of a Sensor Polymer for Measuring D-glucose in Porcine Plasma This example shows the preparation of a sensor polymer and its use in accordance with the present invention to measure the concentrations of glucose in a complex biological fluid, porcine plasma. It also demonstrates the utility of the ligand exchange process in eliminating the background signal by pre-treating the polymer with carbonate in accordance with the present invention.

Figure 25:
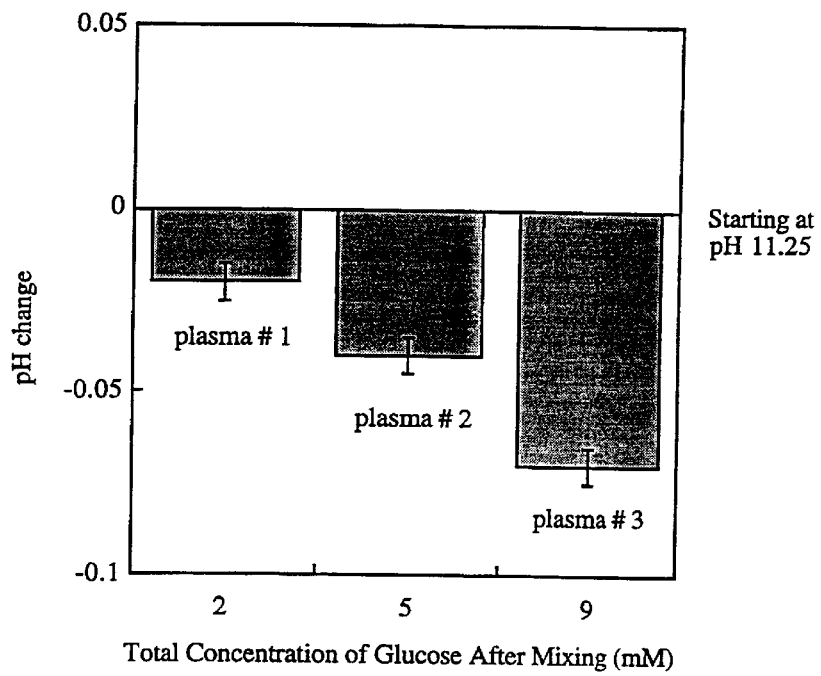

1) Measurement of Glucose in Porcine Plasma Using the Polymer Pre-treated with Carbonate:

a) Polymer Preparation: The Cu-TACN-containing polymer (same material as in example 13, 0.5 g) was suspended in 1.00 mL 80 mM $Na_2CO_3$ in a titration vessel (719 S Titrino, Brinkman Instruments, Westbury, N.Y.). The vessel was sealed, purged thoroughly with $N_2$, and equilibrated to 25° C. by a constant temperature water bath. The pH of the suspension was adjusted to 11.25. The resulting suspension was directly used in the next step.

b) Measurement of glucose in porcine plasma using polymer pre-treated with carbonate and measurement of pH change: A direct titration of porcine plasma into the polymer-water suspension was performed. Three plasma samples were prepared, each with a different glucose concentration. The glucose concentration in plasma #1 was 6.88±0.17 mM as measured on Beckman Glucose Analyzer II. Glucose concentrations of plasma #2 and #3 were adjusted to 22.6 mM and 44.8 mM respectively by adding D-glucose to plasma #1. The pH of the plasmas samples were adjusted to 11.25. The pH change of the polymer suspension was recorded after addition of the plasma sample (0.25 mL). The data are plotted in FIG. 25. As shown in FIG. 25, when the plasma samples were added to the polymer suspensions, the pH of the final mixture decreased. The higher the glucose concentration of the final mixture was, the more the pH decreases.

As can be seen from FIG. 25, the pH decrease is proportional to the amount of glucose added to the polymer suspension. A sensor incorporating the metal complexing polymer and a pH measurement apparatus thus has provided a measure of the amount of glucose added to the solution. The concentration of glucosamine in an unknown sample can be determined by comparison of the pH change under comparable conditions to the protons released at the known glucose concentrations.

EXAMPLE 15

Preparation and Use of a Sensor Polymer for Measuring Lactic Acid and D-glucosamine This example shows the preparation and use of a sensor material to measure analyte concentrations in accordance with the present invention. The example also demonstrates the ability of the sensor material to undergo the ligand exchange reaction with target molecules to produce hydroxide ions. This example uses [Cu(II)(1-vinylbenzyl-1,4,7-triazacyclononane)$SO_4$] ([Styryl-TACN-$Cu^{2+}$] $SO_4$) as the polymerizable metal complex, and 1,4-anhydroerythritol (cis-diol) as exchangeable ligand in the polymer supported Cu(II) complex.

Pre-treatment of Cu(TACN) Containing Polymer with cis-diol:

The synthesis of Cu(TACN) containing polymer has already been described in Example 13. The polymer (0.100 g, 0.034 mmol $Cu^{2+}$) was suspended in 1.00 mL 0.25M 1,4-anhydroerythritol (cis-diol) solution in a titration vessel (719 S Titrino, Brinkman Instruments, Westbury, N.Y.). The vessel was sealed, purged thoroughly with $N_2$, and equilibrated to 25° C. by a constant temperature water bath. The pH of the suspension was adjusted to 10.25. The resulting suspension could be directly used as sensor material. Alternatively, the suspension could be filtered to remove the aqueous supernatant. Furthermore, the suspension could be freeze-dried, and then be used as sensor material. In this example, the suspension was directly used as sensor material in conjunction with pH static titration to show a response to lactic acid and glucosamine.

Measurement of L-lactic Acid Using the Polymer Pre-treated with cis-diol and pH Static Titration:

An aqueous solution of L-Lactic acid with a concentration of 0.500 M and a pH of 10.25 was prepared. This solution was then titrated into the cis-diol pre-treated polymer suspension in the titration vessel in 2.5 µL or larger increments. After each injection of D-glucose the pH of the solution increased, and the automatic pH titrator automatically added 0.100 N HCl solution to bring the solution pH back to the original value. The volumes of the lactic acid solution injected and the volumes of the 0.100 N sodium hydroxide added to maintain constant pH were recorded and used to calculate the hydroxide ion release. The results are plotted in FIG. 26.

Figure 26:
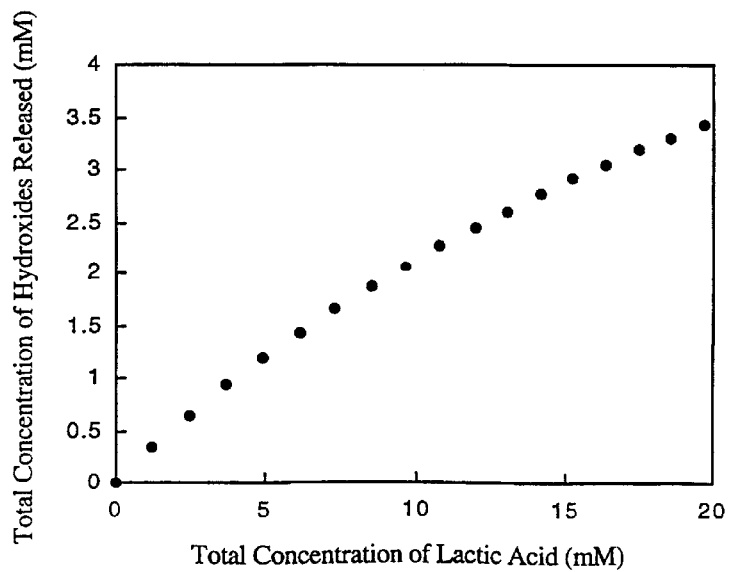

As can be seen from FIG. 26, the released hydroxide concentration is nearly linearly proportion to the concentration of lactic acid in the solution. A sensor incorporating the metal complexing polymer and a pH titration apparatus thus has provided a measure of the amount of lactic acid in solution. The concentration of lactic acid in an unknown sample can be determined by comparison of the hydroxide ions released under comparable conditions to the ions released at the known lactic acid concentrations. This method is useful for monitoring lactic acid concentrations, or the concentration of other α-hydroxyl carboxylic acids in solution, provided large concentrations of competing compounds such as amino alcohols or diols are not present.

Measurement of D-glucosamine Using the Polymer Pre-treated with cis-diol and pH Static Titration:

An aqueous solution of D-glucosamine with a concentration of 0.500 M and a pH of 10.25 was prepared. This glucosamine solution was then titrated into the cis-diol pre-treated polymer suspension in the titration vessel in 2.5 µL or larger increments. After each injection of D-glucosamine the pH of the solution increased, and the pH titrator automatically added 0.100 N HCl solution to bring the solution pH back to the original value. The volumes of the D-glucosamine solution injected and the volumes of the 0.100 N sodium hydroxide added to maintain constant pH were recorded for data processing and calculation of the hydroxide ion release. The results are plotted in FIG. 27.

As can be seen from FIG. 27, the released hydroxide concentration is nearly linearly proportional to the concentration of glucosamine in the solution. A sensor incorporating the metal complexing polymer and a pH titration apparatus thus has provided a measure of the amount of glucosamine in solution. The concentration of glucosamine in an unknown sample can be determined by comparison of the hydroxide ions released under comparable conditions to the ions released at the known glucosamine concentrations. This method is useful for monitoring glucosamine concentrations, or the concentration of other related molecules in solution, provided large concentrations of competing compounds such as other amino alcohols, amino acids or diols are not present.

EXAMPLE 16

Preparation and Use of a Sensor Polymer for Measuring L-Alanine

This example shows the preparation of a sensor polymer and its use in accordance with the present invention to measure the concentration of an amino acid. The example also demonstrates the ability of the sensor polymer to undergo ligand exchange reaction with L-alanine and produce hydroxide ions, which are measured through their effect on solution pH. This example uses [Cu(II)(1-vinylbenzyl- 1,4,7-triazacyclononane)$SO_4$] ([styryl-TACN-$Cu^{2+}$] $SO_4$) as the polymerizable metal complex and 1,4-anhydroerythritol (cis-diol) as exchangeable ligand in the polymer supported Cu(II) complex.

Measurement of D-glucose Using Polymer Pre-treated with cis-diol and pH Change:

Polymer is that from previous examples and pretreated as described before with cis-diol. An aqueous solution of 0.50 M L-alanine was prepared at pH=10.25. This solution was then titrated into the cis-diol pre-treated polymer suspension in the titration vessel in 2.5 µL or larger increments. After each injection of L-alanine, the pH of the solution was recorded. The pH changes of the solution at different L-alanine concentrations are plotted in FIG. 28.

Figure 28:
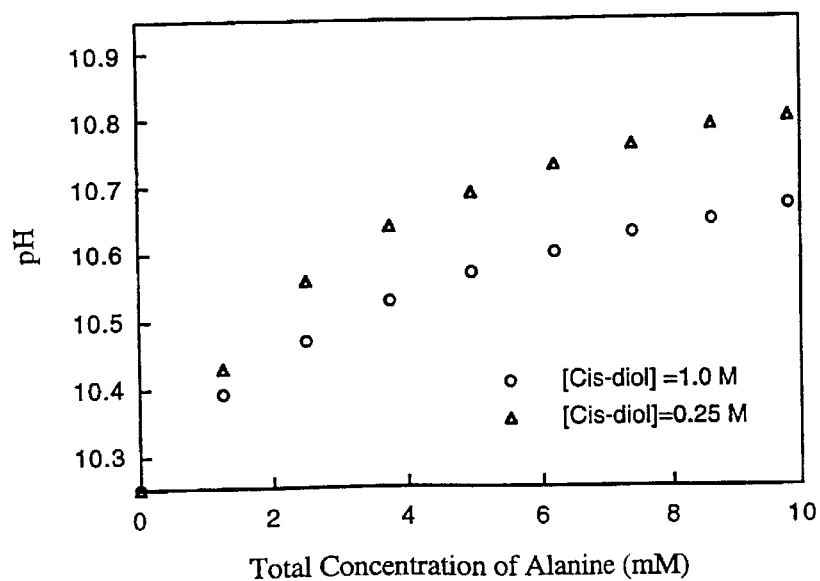

As can be seen from FIG. 28, the pH changes measured in the suspension are proportional to the concentration of L-alanine in solution. A sensor incorporating the metal complexing polymer and a pH measuring apparatus thus has provided a measure of the amount of amino acid in solution. The concentration of amino acid in an unknown sample can be determined by comparison of the hydroxide ions released under comparable conditions to the ions released at the known amino acid concentrations. This method is useful for monitoring amino acid concentrations, provided large concentrations of competing compounds such as amino alcohols or diols are not present.

FIG. 28 also shows that increasing the exchangeable ligand concentration (cis-diol) decreases the measured pH change at a given analyte concentration. This ability of the exchangeable ligand to suppress the binding of other compounds can be used advantageously, for example to allow only a strong binder, such as an amino acid, of a mixture in a solution to cause a measurable pH change. In this way, weaker binding compounds will not interfere with the measurement.

EXAMPLE 17

Preparation Of A Sensor For D-Glucose Using Detection Of Cl$^-$

This example shows the preparation of a sensor in accordance with the present invention. The example also demonstrates the ability of the sensor to undergo ligand exchange reaction with target molecules, and produce chloride anions. This example uses [Cu(TACN)Cl$_2$] as the sensing metal complex, and chloride anion as the exchangeable ligand.

A 2 mL solution of [Cu(TACN)Cl2] (52.6 mg, 0.200 mmol Cu$^{2+}$) and NaCl (46.8 mg, 0.400 mmol) was placed in a titration vessel (719 S Titrino, Brinkman Instruments, Westbury, N.Y.). The vessel was sealed, purged thoroughly with N$_2$, and equilibrated to 25° C. with a water bath. The pH of the suspension was adjusted to 10.00. The solution had a reading of −78.9 mV, as measured from a combination chloride electrode (VWR Scientific, San Francisco, Calif.).

A 0.500 M, pH 10.00 aqueous D-glucose solution was prepared. Saturated NaCl solution was titrated into this solution until it had a reading of −78.9 mV, as measured from the combination chloride electrode. This solution was then titrated into the Cu(TACN)Cl$_2$ solution in the titration vessel in 10 μL or larger increments. The volumes of the glucose solution injected and the chloride electrode potential of the Cu(TACN)Cl$_2$ solution after each injection of glucose was recorded, and the resulting electrode potential changes are plotted in FIG. 29.

Figure 29:
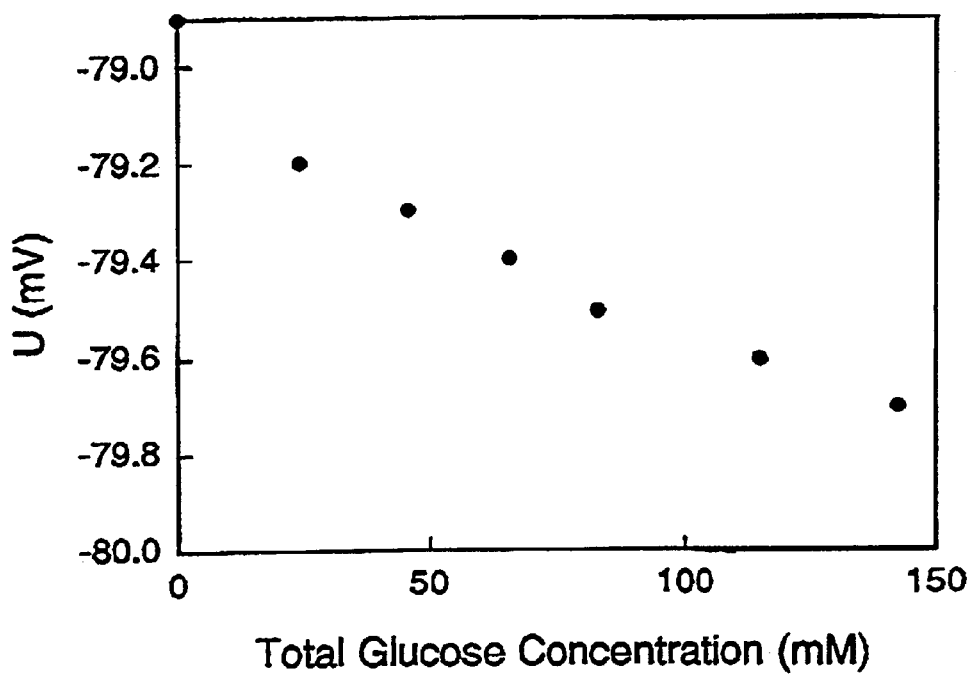

As can be seen from FIG. 29, the electrode potential is approximately linearly proportional to the solution glucose concentration. This sensor configuration can be used to determine glucose concentrations in an aqueous sample.

Having thus described exemplary embodiments of the present invention, it should be noted by those skilled in the art that the disclosures herein are exemplary only and that various other alternations, adaptations and modifications may be made within the scope of the present invention. Accordingly, the present invention is not limited to the specific embodiments as illustrated herein.

The following list of references provides additional background information relating to the present invention. The references cited in the following list and other references and patents referred to in this specification are hereby incorporated by reference.

REFERENCES

1. Pickup, J. C. and Williams, G. (eds) *Textbook of Diabetes*, Blackwell Scientific Publications, 1991.
2. Jannson, P. A., Fowelin, J., Smith, U. and Lonnroth, P., "Characterization by microdialysis of intercellular glucose level in subcutaneous tissue in humans," *Am. J. Physiol.*, 255, 218–220,1988.
3. Tamada, J. A., Bohannon, N. J. V., Potts, R. O., "Measurement of glucose in diabetic subjects using noninvasive transdermal extraction," *Nature Medicine*, 1, 1198–1201,1995.
4. Turner, A. D. F.; Kraube, I. and Wilson, G. S. (eds) *Biosensors: Fundamental and Applications*, Oxford University Press, 1987.
5. Wilkins, E. and Wilkins, M. G., "Implantable Glucose Sensor," *J. Biomed. Eng.* 5, 309–315,1983.
6. Shaw, G. W., Claremont, D. J. and Pickup, J. C., "In vitro testing of a simply constructed, highly stable glucose sensor suitable for implantation in diabetic patients," *Biosensors & Bioelectronics*, 6, 401–406,1991.
7. Pickup, J., "Developing glucose sensors for in vivo use," *TIBTECH*, 11, 285–291,1993.
8. Pfeiffer, E., "Artificial pancreas, glucose sensors and the impact upon diabetology," *Int'l J. Artifi. Org.* 16, 636–644,1993.
9. Kawagoe, J. L., Niehaus, D. E. and Wrightman, R. M., "Enzyme-modified organic conducting salt microelectrode," *Anal. Chem.*, 63, 2961–2965, 1991.
10. Meyerhoff, C., Bischol, F., Mennel, F. J., Sternberg, F., Pfeiffer, E. F., "Use of the microdialysis technique in the monitoring of subcutaneous tissue glucose concentration," *Int'l J. Artif. Org.*, 16, 268–275,1993.
11. Moussy, F., Harrison, D. J., O'Brien, D. W., Rajotte, R. V., "Performance of subcutaneously implanted needle-type glucose sensors employing a novel trilayer coating," *Anal. Chem.*, 65, 2072–2077,1993.
12. Bambot, S. B. et al., *Biosensors & Bioelectronics*, 10, 643–652 (1995).
13. Kullick, T. et al., *Analyt. Chim. Acta.*, 1994, 296, 263–26.
14. Vering, T. et al., Electroanalusis, 1994, 6, 953–956.
15. Bambot, S. B., Lakowicz, J. R. and Rao, G., "Potential applications of lifetime-based, phase-modulation fluorimetry in bioprocess and clinical monitoring," *TIBTECH*, 13, 106–115,1995.
16. Wolfbeis, O. S., "Optical sensing based on analyte recognition by enzymes, carriers and molecular interactions, *Analytica Chimica Acta*, 250, 181–210, 1991.
17. Trettnak, W., Leiner, M. J. P. and Wolfbeis, O. S., "Fibre-optic glucose sensor with a pH optrode as the transducer," *Biosensors*, 4, 15–26 (1988).
18. Bambot, S. B., Sipior, J., Lakowicz, J. R. and Rao, G., "Lifetime-based optical sensing of pH using resonance energy transfer in sol-gel films," Sensors and Actuators B, 22, 181–188,1994.
19. Szmacinski, H. and Lakowicz, J. R., "Optical measurements of pH using fluorescence lifetimesand phase-modulationfluorometry," *Anal. Chem.*, 65, 1668–1674, 1993.
20. Lakowicz, J. R., Szmacinski, H. and Karakelle, M., "Optical sensing of pH and PCO$_2$ phase-modulation fluorimetry and resonance energy transfer," *Analytica Chimica Acta*, 272,179–186,1993.
21. Bambot, S. B., Rao, G., Romauld, M., Carter, M., Carter, G. M., Sipior, J., Terpetchnig, E. and Lakowicz, J. R., "Sensing oxygen through skin using a red diode laser and fluorescence lifetimes," *Biosensors and Bioelectronics*, 10, 643–652,1995.
22. Werner, T. and Wolfbeis, O. S., "Optical sensor for the pH 10–13 range using a new support material," *Fresenius J. Anal. Chem.*, 346, 564–568, 1993.

23. Lippitsch, M. E., Pusterhofer, J., Leiner, M. J. P. and Wolfbeis, O. S., *Analytica Chimica Acta*, 205,1–6, 1988.
24. Weigl, B. H. and Holobar, A., Rodriguez, N. V. and Wolfbeis, O. S., "Chemically and mechanically resistant carbon dioxide optrode based on a covalently immobilized pH indicator," *Analytica Chimica Acta*, 282, 335–343,1993.
25. Hitzmann, B. and Kullick, T., "Evaluation of pH field effect transistor measurement signals by neural networks," *Analytica Chimica Acta*, 294, 243–249, 1994.
26. Saito, A., Ito, N., Kumura, J. and Kuriyama, T., *Sensors and Actuators B*, 20,125–129,1994.
27. Bergveld, P., van Hal, R. E. G. and Eijkel, J. C. T., "The remarkable similarity between the acid-base properties of ISFETs and proteins and the consequences for the design of ISFET biosensors," *Biosensors and Bioelectronics*, 10, 405–414, 1995.
28. Wilkinson, S. G. (ed) *Comprehensive Coordination Chemistry*, Vol. 2, Pergamon Press, 1987, pp. 47.
29. a) Dung, N-H., Viossat, B., Busnot, A et al., *Inorganica Chimica Acta*, 1990, 169, 9–12; b) ibid, 1990, 174, 145–148.
30. Bereman, R. D., Churchill, M. R., Schaber, P. M. and Winkler, M. E., *Inorg. Chem.*, 1979, 18, 3122.

What is claimed is:

1. A system for measuring the concentration of target molecules in solution, comprising:
   (a) a sensing material comprising metal complexes having at least two coordination sites available for binding at least one of the target molecules selected from the group consisting of a sugar, a monosaccharide, a disaccharide, a trisaccharide, an oligosaccharide, an amino sugar, a sugar-amino acid, an amino acid, an amino alcohol, an α-hydroxycarboxylic acid, a sugar-peptide, a glycoprotein, glycerol, dopamine, a catechol, ascorbic acid, a polyol, a diol, ethyleneglycol, sialic acid, carbonate, phosphate, sulfate, CO, NO, 3-hydroxy-L-tyrosine, and a molecule having multiple hydroxyl groups, the metal complexes releasing protons or hydroxide ions upon binding of the target molecules; and
   (b) a detector for measuring the protons or hydroxide ions released from the sensing material and for providing a measurement of the concentration of the target molecules in the solution,
      wherein the detector is selected from the group consisting of a pH electrode, a field effect transistor, a light addressable potentiometric sensor, and a solution conductivity measuring device, or
      wherein the detector measures optical or electrical characteristics of the sample and the system further comprises a chemical probe whose optical or electrical properties are sensitive to pH.

2. A system for measuring the concentration of target molecules in solution, comprising:
   (a) a sensing material comprising metal complexes having the formula

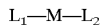

wherein M is a metal ion; $L_1$ is a nitrogen based polydentate ligand; and $L_2$ is an exchangeable ligand; the metal complexes having at least two coordination sites available for binding at least one of the target molecules selected from the group consisting of a sugar, a monosaccharide, a disaccharide, a trisaccharide, an oligosaccharide, an amino sugar, a sugar-amino acid, an amino acid, an amino alcohol, an α-hydroxycarboxylic acid, a sugar-peptide, a glycoprotein, glycerol, dopamine, a catechol, ascorbic acid, a polyol, a diol, ethyleneglycol, sialic acid, carbonate, phosphate, sulfate, CO, NO, 3-hydroxy-L-tyrosine, and a molecule having multiple hydroxyl groups, the metal complexes releasing exchangeable ligands upon binding of the target molecules; and
   (b) a detector for measuring the exchangeable ligands released from the sensing material and for providing a measurement of the concentration of the target molecules in the solution.

3. The system according to claim 1 or claim 2 wherein the metal complexes are attached to a support structure.

4. The system according to claim 3 wherein the support structure comprises an organic or inorganic polymer.

5. The system according to claim 3 wherein the support structure is an optically transparent surface selected from the group consisting of quartz, glass and a fiber optic cable.

6. The system according to claim 3 wherein the metal complex comprises a monomer, wherein the monomer is co-polymerized or grafted to the support structure.

7. The system according to claim 1 or claim 2 wherein the metal complexes contain a polymerizable moiety and embedded by copolymerization with at least one other monomer, crosslinking agent or combination thereof into a polymeric matrix.

8. The system according to claim 1 or claim 2 wherein the metal complexes contain metal ions selected from the group consisting of copper ions, iron ions, lead ions, cobalt ions, nickel ions, mercury ions and aluminum ions.

9. The system according to claim 1 or claim 2 wherein the target molecule is glucose.

10. The system according to claim 1 or claim 2 wherein each of the metal complexes contains a polymerizable moiety, is preorganized with a template molecule, and is embedded by copolymerization with a monomer and a cross linking agent into an imprinted polymeric matrix, wherein the template molecule is the target molecule or an analog of the target molecule.

11. The system according to claim 2 wherein M is a metal ion selected from the group consisting of copper ion, iron ion, lead ion, cobalt ion, nickel ion, mercury ion and aluminum ion; $L_1$ is a nitrogen-based bidentate ligand, nitrogen-based linear tridentate ligand, nitrogen-based linear tetradentate ligand, nitrogen-based tridentate macrocycle ligand, nitrogen-based tridentate ligand with pendant arms, nitrogen-based tetradentate macrocyclic ring ligand or tridentate ligand comprising pyridine, pyrazole or imidazole rings.

12. The system according to claim 11 wherein $L_1$ is a ligand selected from the group consisting of triazacyclononane (TACN), 1,4-dialkyl triazacyclononane, 1,4-dimethyl-triazacyclononane(1,4-dimethyl-TACN), ethylene-diamine (En), propylenediamine (II)-PDN), imino-diacetate (IDA), diethylenetriamine (Dien), 1-oxa-4,7-diazacyclononane, 1-thia-4,7-diazacyclononane and derivatives thereof.

13. The system according to claim 11 wherein the $L_1$-M portion of said metal complex is selected from the group consisting of copper(II)-triazacyclononane(Cu(TACN)), copper(II)-1,4-dialkyltriazaclononane, copper(II)-1,4-dimethyl triazacyclononane (Cu(1,4-dimethyl-TACN)), copper(II)-ethylenediamine (Cu(En)), copper(II)-propylenediamine (Cu(II)-PDN)), copper(II)-iminodiacetate (Cu(IDA)), copper(II)-diethylenetriamine(Cu(Dien), copper (II) 1-oxa-4,7-diazacyclononane, copper(II) 1-thia-4,7-diazacyclononane and derivatives thereof.

14. The system according to claim 11 wherein $L_2$ is selected from the group consisting of ionic species, amines, amino acids, phenol, carboxylic acids, amino alcohols, diols, and derivatives thereof.

15. The system according to claim 14 wherein the $L_1$-M portion of said metal complex is copper(II)-triazacyclononane (Cu(TACN)) and derivatives thereof.

16. The system according to claim 14 wherein $L_2$ is measured by fluorescence, chemiluminescence, phosphorescence, colorimetrically or electrochemically.

17. A method for measuring the concentration of target molecules in a solution, comprising the steps of:
(a) placing the solution in contact with a sensing material comprising metal complexes wherein each metal complex has the property of:
 (i) holding a metal ion tightly in the complex;
 (ii) allowing at least two coordination sites to be or become available for binding to one of the target molecules;
 (iii) binding the target molecule in solution, wherein the target molecule is selected from the group consisting of a sugar, a monosaccharide, a disaccharide, a trisaccharide, an oligosaccharide, an amino sugar, a sugar-amino acid, an amino acid, an amino alcohol, an α-hydroxycarboxlic acid, a sugar-peptide, a glycoprotein, glycerol, dopamine, a catechol, ascorbic acid, a polyol, a diol, ethyleneglycol, sialic acid, carbonate, phosphate, sulfate, CO, NO, 3-hydroxy-L-tyrosine, and a molecule with multiple hydroxyl groups; and
 (iv) upon binding of the metal complex with the target molecules, releasing a detectable entity or entities selected from the group consisting of protons, hydroxide ions and exchangeable ligands wherein the number of released detectable entities is proportional to the concentration of the target molecules in the solution;
(b) binding the target molecules in the solution to the metal complexes;
(c) releasing the detectable entities into the solution; and
(d) measuring the amount of detectable entities released from the sensing material to provide a measurement of the concentration of target molecules in the solution.

18. The method according to claim 17 wherein the exchangeable ligands are included on the metal complexes and are exchanged for the target molecules during binding to the metal complexes.

19. The method according to claim 17 wherein the solution is a mammalian bodily fluid and the target molecule is sugar or a sugar derivative.

20. The method according to claim 17 wherein the metal complexes contain a polymerizable moiety and are embedded by copolymerization with at least one monorner, crosslinking agent, or combination thereof into a polymeric matrix.

21. The method according to claim 17 wherein each of the metal complexes contains a polymerizable moiety, is preorganized with a template molecule, and is embedded by copolymerization with a monomer and a crosslinking agent into an imprinted polymeric matrix, wherein the template molecule is the target molecule or an analog of the target molecule.

22. The method according to claim 17 wherein the metal complexes contain metal ions selected from the group consisting of copper ions, iron ions, lead ions, cobalt ions, nickel ions, mercury ions and aluminum ions.

23. A method according to claim 17 wherein each of the metal complexes has the formula

wherein M is a metal ion selected from the group consisting of copper ion, iron ion, lead ion, cobalt ion, nickel ion, mercury ion and aluminum ion; $L_1$ is a nitrogen-based bidentate ligand, nitrogen-based linear tridentate ligand, nitrogen-based linear tetradentate ligand, nitrogen-based tridentate macrocycle ligand, nitrogen-based tridentate ligand with pendant arms, nitrogen-based tetradentate macrocyclic ring, ligand or tridentate ligand comprising pyridine, pyrazole or imidazole rings, or any of the preceding nitrogen-based $L_1$ compounds wherein at least one nitrogen atom is replaced by either an oxygen or a sulfur atom; and $L_2$ is an exchangeable ligand.

24. The method according to claim 23 wherein the $L_1$-M portion of said metal complex is selected from the group consisting of copper(II)-triazacyclononane(Cu(TACN)), copper(II)-1,4-dialkyltriazaclononane, copper(II)-1,4-dimethyl triazacyclononane (Cu(1,4-dimethyl-TACN)), copper(II)-ethylenediamine (Cu(En)), copper(II)-propylenediamine (Cu(II)-PDN)), copper(II)-iminodiacetate (Cu(IDA)), copper(II)-diethylenetriamine(Cu(Dien), copper (II) 1-oxa-4,7-diazacyclononane, copper(II) 1-thia-4,7-diazacyclononane and derivatives thereof.

25. The method according to claim 23 wherein the $L_1$-M portion of said metal complex is copper(II)-triazacyclononane (Cu(TACN)) and derivatives thereof.

26. The method according to claim 23 wherein $L_2$ is selected from the group consisting of ionic species, amines, amino acids, phenol, carboxylic acids, amino alcohols, diols, and derivatives thereof.

27. The method according to claim 26 wherein $L_2$ is measured by fluorescence, chemiluminescence, phosphorescence, colorimetrically or electrochemically.

28. The method according to claim 17 wherein the target molecule is glucose.

29. The method according to claim 17 wherein the metal complexes are attached to a support structure.

30. The method according to claim 29 wherein the support structure comprises an organic or inorganic polymer.

31. The method according to claim 24 wherein the support structure is an optically transparent surface selected from the group consisting of quartz, glass or a fiber optic cable.

32. The method according to claim 17 wherein each of the metal complexes contains a polymerizable moiety preorganized with a template molecule to form a templated metal complex, the tenplated metal complex being embedded by copolymerization with at least one monomer, crosslinking agent or a combination thereof into an imprinted polymeric matrix, wherein the template molecule is the target molecule or an analog of the target molecule.

* * * * *